United States Patent
Dodey et al.

(10) Patent No.: US 6,479,515 B1
(45) Date of Patent: Nov. 12, 2002

(54) HETEROCYCLIC BENZENESULPHONAMIDE COMPOUNDS AS BRADYKININE ANTAGONISTS

(75) Inventors: Pierre Dodey, Fontaine lès Dijon (FR); Martine Barth, Asnières les Dijon (FR); Michel Bondoux, Fontaine lès Dijon (FR)

(73) Assignee: Fournier Industrie et Sante, Chenove (FR)

( * ) Notice: Subject to any disclaimer, the term of this patent is extended or adjusted under 35 U.S.C. 154(b) by 0 days.

(21) Appl. No.: 09/889,965

(22) PCT Filed: Feb. 17, 2000

(86) PCT No.: PCT/FR00/00396
§ 371 (c)(1),
(2), (4) Date: Jul. 24, 2001

(87) PCT Pub. No.: WO00/50418
PCT Pub. Date: Aug. 31, 2000

(30) Foreign Application Priority Data

Feb. 26, 1999 (FR) .............................................. 99 02412

(51) Int. Cl.[7] .................. A61K 31/4709; C07D 401/14
(52) U.S. Cl. ........................ 514/314; 546/172; 546/159; 544/128; 544/363; 514/235.5; 514/253
(58) Field of Search .............................. 514/314, 235.5, 514/253; 546/172, 159; 544/128, 363

(56) References Cited

U.S. PATENT DOCUMENTS

| | | |
|---|---|---|
| 5,006,534 A | 4/1991 | Mohrs et al. |
| 5,070,096 A | 12/1991 | Mohrs et al. |
| 5,093,340 A | 3/1992 | Mohrs et al. |
| 5,202,336 A | 4/1993 | Mohrs et al. |
| 5,510,380 A | 4/1996 | Seoane et al. |
| 5,578,601 A | 11/1996 | Seoane et al. |
| 5,597,803 A | 1/1997 | Breipohl et al. |
| 5,610,140 A | 3/1997 | Goodfellow et al. |
| 5,610,142 A | 3/1997 | Mavunkel et al. |
| 5,620,958 A | 4/1997 | Cheronis et al. |
| 5,968,951 A | 10/1999 | Dodey et al. |
| 5,994,368 A | 11/1999 | Oku et al. |
| 6,008,229 A | 12/1999 | Oku et al. |
| 6,080,758 A | 6/2000 | Dodey et al. |
| 6,083,959 A | 7/2000 | Oku et al. |
| 6,100,284 A | 8/2000 | Oku et al. |

FOREIGN PATENT DOCUMENTS

| | | |
|---|---|---|
| DE | 36 17 183 | 5/1987 |
| EP | 0 261 539 | 9/1987 |
| EP | 0 596 406 A1 | 5/1994 |
| EP | 0 622 361 A1 | 11/1994 |
| FR | 2 735 128 | 12/1996 |
| FR | 2 737 892 | 2/1997 |
| FR | 2 743 073 | 7/1997 |
| FR | 2 756 562 | 6/1998 |
| FR | 2 765 222 | 12/1998 |
| JP | 09-40662 | 2/1997 |
| WO | WO 96/13485 | 5/1996 |
| WO | WO 97/09346 | 3/1997 |
| WO | WO 97/09347 | 3/1997 |
| WO | WO 97/11069 | 3/1997 |
| WO | WO 97/41104 | 11/1997 |

OTHER PUBLICATIONS

Bhoola et al. "Bioregulation of Kinins: Kallikreins, Kinonogens, and Kininases." Pharmalogical Review, vol. 44, No. 1, pp. (1992).

Stewart. "Bradykinin Antagonists: Development and Applications." Biopolymers (Peptide Science), vol. 37, pp. 143–155. (1995).

*Primary Examiner*—C. S. Aulakh
(74) *Attorney, Agent, or Firm*—Merchant & Gould P.C.

(57) ABSTRACT

The invention concerns compounds selected among the group consisting of (i) compounds of formula (I) wherein: Het1 represents a nitrogenous heterocycle with 5 apices, in particular imidazole, pyrazole, or triazole; Het2 represents a nitrogenous heterocycle with 4, 5 or 6 apices, selected among the heterocycles: (II) wherein $R_1$ and $R_2$ are defined as mentioned in the description; and (ii) their additive salts. The invention also concerns the method for preparing said compounds and their use in therapy, in particular for treating pathologies involving bradykinine.

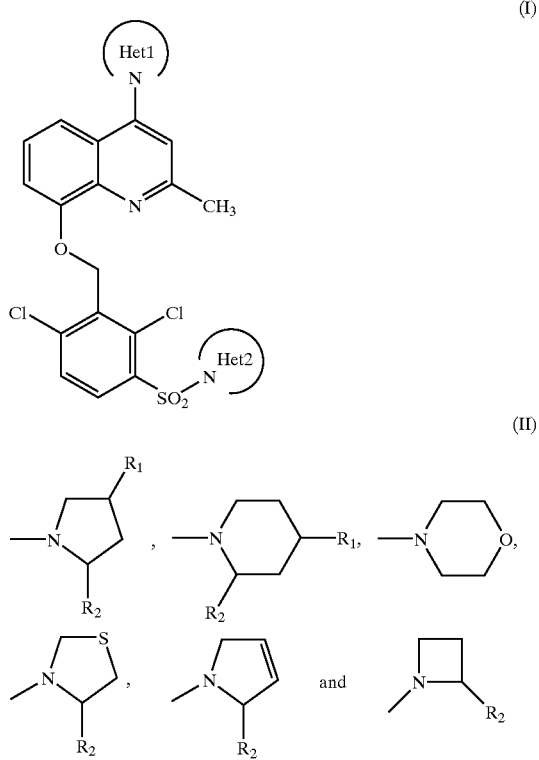

20 Claims, No Drawings

HETEROCYCLIC BENZENESULPHONAMIDE COMPOUNDS AS BRADYKININE ANTAGONISTS

This application is a 371 of PCT/FR00/00398 filed Feb. 17, 2000, now WO 00/50418.

FIELD OF THE INVENTION

The present invention relates to novel benzenesulphonamide compounds, their method of preparation and their therapeutic use.

These novel compounds have an antagonist action towards bradykinin and are useful in therapeutics, particularly for the treatment of pain and inflammation, and especially in the treatment of asthma, cerebral traumatic shock and allergic rhinitis.

PRIOR ART

It is known that one of the possibilities for treatment of certain pathologies of painful and/or inflammatory character (such as asthma, rhinitis, septic shock, dental pain, etc.) is to inhibit the action of certain hormones such as bradykinin or kallidin. In reality, these peptide hormones are involved in a large number of physiological processes, some of which are closely associated with these pathologies.

Although at present no product having this mode of action is commercially available yet, many studies have been undertaken in order to understand the mode of action of kinins and in particular of bradykinin and its homologues, then to create compounds capable of being bradykinin-receptor antagonists. Among the numerous publications relating to these studies, mention may be made of Pharmacological Reviews Vol. 44 no. 1, pages 1–80 (1992) and Biopolymers (Peptide Science) vol. 37 pages 143–155 (1995).

Bradykinin is a peptide hormone formed of 9 amino acids (Arg-Pro-Pro-Gly-Phe-Ser-Pro-Phe-Arg) and kallidin is a peptide hormone (Lys-Arg-Pro-Pro-Gly-Phe-Ser-Pro-Phe-Arg) which contains a supplementary amino acid (Lys) with respect to bradykinin. It is known that prior studies have made it possible to obtain peptides which interact with the bradykinin receptors: some such as bradycor (CP.0127 from the company Cortech), icatibant (HOE 140 from the company Hoechst) ["bradycor" and "icatibant" are international non-proprietary names (INN)] or alternatively NPC 17761 (from the company Scios-Nova) have an inhibitory action on the binding of bradykinin to its $B_2$ receptor. Recent publications cite other peptides capable of having a bradykinin-antagonist action towards its $B_2$ receptor; among these it is possible to mention, for example, WO-A-97/09347, WO-A-97/09346, U.S. Pat. Nos. 5,610,140, 5,620,958, 5,610,142 and 5,597,803. In addition, non-peptide compounds have been proposed as antagonists towards the binding of bradykinin to its $B_2$ receptor, especially in EP-A-0596406, EP-A-0622361, U.S. Pat. Nos. 5,578,601, 5,510,380, FR-A-2735128, JP-A-09/040662, FR-A-2737892, WO-A-97/11069, WO-A-97/41104, WO-A-96/13485 and FR-A-2765222. It is additionally known that certain compounds of structure which is more or less related to those of the compounds aimed at in the present application have already been described, especially in DE-A-3617183 and EP-A-0261539, with regard to their possible antithrombotic properties.

AIM OF THE INVENTION

There is a need to attenuate or to suppress pain and inflammation in mammals and especially in man.

To satisfy this need, a novel technical solution has been sought which is effective in the treatment of pain irrespective of its origin, especially in the treatment of pain associated with inflammatory or traumatic phenomena.

According to the invention, it is proposed to provide a novel technical solution, which employs, at the level of the bradykinin $B_2$ receptor, competitive binding between (i) bradykinin and related or analogous hormones, and (ii) an antagonist substance, and which requires compounds of benzenesulphonamide type, which are structurally different from the abovementioned known products, and are capable of limiting or substantially inhibiting the binding of bradykinin and analogous hormones to the said bradykinin $B_2$ receptor.

According to this technical solution, the novel compounds bind competitively to the bradykinin $B_2$ receptor without causing the effects of bradykinin on this receptor (these novel compounds are so-called antagonist substances). This results in the appearance of a state analogous to that observed in the absence of bradykinin, namely a decrease in pain, inflammatory reactions and other harmful effects caused by the receptors activated by bradykinin.

In accordance with this novel technical solution, according to a first aspect of the invention, compounds derived from benzenesulphonamide are proposed as novel industrial products; according to a second aspect of the invention, a method of preparation of these compounds is proposed; and according to a third aspect of the invention, a use of these compounds, especially a therapeutic use, as active principles of specialities or medicinal compositions is proposed.

SUBJECT OF THE INVENTION

According to the novel technical solution of the invention, a benzenesulphonamide compound is recommended as novel industrial product, which is characterized in that it is chosen from the group formed by:

(i) the compounds of formula I:

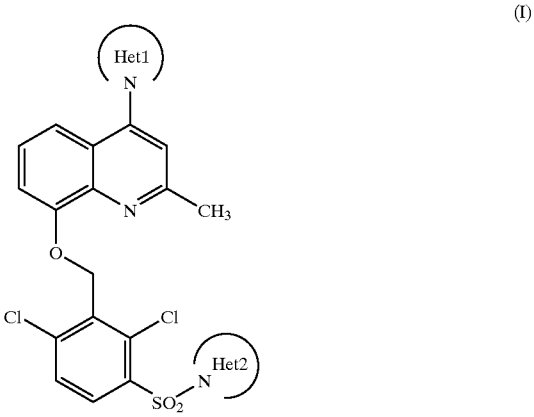

in which:
Het1 represents a 5-membered nitrogen-containing heterocycle, especially imidazole, pyrazole or triazole,
Het2 represents a 4-, 5- or 6-membered nitrogen-containing heterocycle of structure:

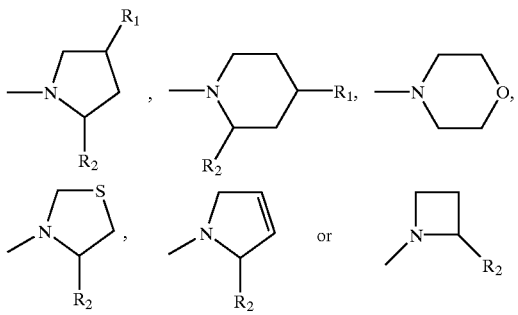

in which $R_1$ represents a hydrogen atom or a hydroxyl, $C_1$–$C_4$ alkoxy, phenoxy, phenylmethoxy, —$CH_2OH$, cycloalkyloxy, cycloalkylalkoxy (where each cycloalkyl fragment is $C_3$–$C_8$ and the alkoxy fragment is $C_1$–$C_4$), —NH—CO—$CH_3$, —CO—$NH_2$ or —CO—NH—$CH_3$ group, $R_2$ represents a hydrogen atom or a —$CH_2OH$, —$CH_2$—O—$CH_3$, —$CONR_3R_4$,

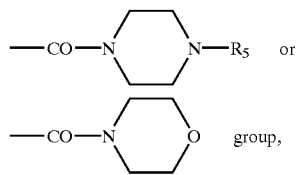

group, $R_3$ represents a hydrogen atom, a $C_1$–$C_3$ alkyl group, a $C_3$–$C_8$ cycloalkyl group, a ($C_3$–$C_8$) cycloalkyl ($C_1$–$C_3$) alkyl group, a phenyl group, or a phenylmethyl group, $R_4$ represents a hydrogen atom, a $C_1$–$C_3$ alkyl, —($CH_2$)n—$CH_2OH$, —($CH_2$)n—COOH, —($CH_2$)n—$CH_2$—$NR_5R_6$,

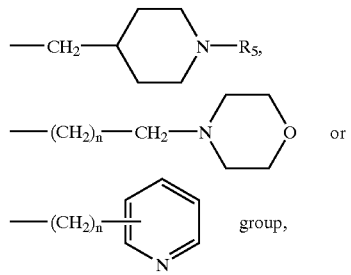

group, $R_5$ represents a hydrogen atom, a $C_1$–$C_3$ alkyl, phenyl, phenylmethyl, pyridinyl, pyridinylmethyl, pyridinylethyl, benzoyl, 4-(amino-iminomethyl)benzoyl, —($CH_2$)$_m$—$CH_2OH$, —($CH_2$)$_m$—COOH, —($CH_2$)$_m$$CH_2$—O—($CH_2$)$_m$—$CH_2OH$, —CO—($CH_2$)$_m$—COOH, or

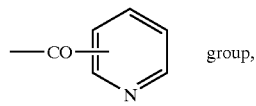

group, $R_6$ represents a hydrogen atom or a $C_1$–$C_3$ alkyl group, or, $R_5$ and $R_6$ considered together form, with the nitrogen atom to which they are attached, a 5- to 6-membered N heterocycle, n=1, 2, 3 or 4,
m=1, 2 or 3; and (ii) their addition salts.

According to the invention, a method of preparation of the compounds of formula I and their addition salts is also recommended.

The use of a bradykinin $B_2$ receptor antagonist substance, chosen from the compounds of formula I of the present invention and their non-toxic addition salts, is likewise recommended for obtaining a medicament intended for human or animal therapeutic use, against pathologies involving bradykinin or its homologues, in particular against pain, especially in the treatment or prevention of pathologies associated with inflammatory or painful states, and against severe traumatic shock, in particular cerebral traumatic shock.

DETAILED DESCRIPTION OF THE INVENTION

In the general formula I of the compounds of the invention, $C_1$–$C_3$ alkyl group is understood as meaning a methyl, ethyl, propyl or 1-methylethyl group.

$C_1$–$C_4$ alkoxy group is preferentially understood here as meaning the methoxy, ethoxy, propoxy, butoxy, 1-methylethoxy and 1,1-dimethylethoxy groups. $C_3$–$C_8$ cycloalkyl group is understood as meaning the cyclopropyl, cyclobutyl, cyclopentyl, cyclohexyl groups, and (cycloalkyl)alkyl groups are understood as meaning especially the cyclopropylmethyl, cyclopropylethyl, cyclohexylmethyl and cyclohexylethyl groups.

When a group such as $R_5$ comprises a heterocycle, for example pyridine, and the position of substitution is not specified, it must be understood that the bond with the heterocycle can be made with any of the substitutable members.

5- to 6-membered $NR_5R_6$ heterocycle is understood as meaning a pyrrolidine, piperidine, piperazine or morpholine ring, and more particularly a 1-pyrrolidinyl, 1-piperidinyl, 1-piperazinyl or 1-morpholinyl group.

The heterocycle Het1, which has five members, comprises one or more heteroatoms. Advantageously, it comprises 1 to 4 nitrogen members. As represented by the formula I above, Het1 is linked by its nitrogen member or one of its nitrogen members to position 4 of the quinoline.

The heterocycle Het2 is linked by its nitrogen member to the sulphur atom of the group $SO_2$ to form the sulphonamide function.

When, on the heterocycle Het2, the substituent $R_2$ is not a hydrogen atom, the carbon of the ring which carries the substituent $R_2$ can have an S or R configuration. In this case, the compounds according to the invention can be of indeterminate configuration (that is to say a mixture of the R and S isomers) or, preferably, one of the R or S isomers, or, preferentially, the S isomer. In the same way, the substituent $R_1$, when it is not hydrogen, introduces an asymmetric centre and can be found in an indeterminate configuration, or determined R or S configuration, the "trans" configuration with respect to the $R_2$ group being preferred.

"Addition salts" are understood as meaning the acid addition salts obtained by reaction of a compound of formula I in its non-salified form with an inorganic acid or an organic acid. The inorganic acids preferred for salifying a basic compound of formula I are hydrochloric, hydrobromic, phosphoric and sulphuric acids. The organic acids preferred for salifying a basic compound of formula I are methanesulphonic, benzenesulphonic, maleic, fumaric, oxalic, citric, lactic, tartaric and trifluoroacetic acids.

Among the compounds according to the present invention, those are preferred in which the heterocycle Het1 is a 1-(1H)-imidazolyl group. The compounds are likewise preferred in which the heterocycle Het2 comprises a 2(S)-pyrrolidinecarboxamide group,

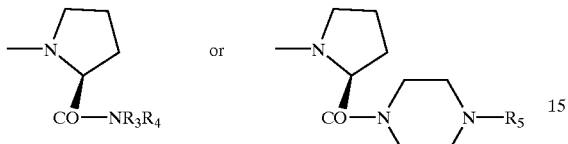

and more particularly when
$R_3$ represents a hydrogen atom or a $C_1$–$C_3$ alkyl group, and
$R_4$ represents a $C_1$–$C_3$ alkyl group, a —$(CH_2)_n$—$CH_2$—$NR_5R_6$ group, a pyridinylmethyl group or a

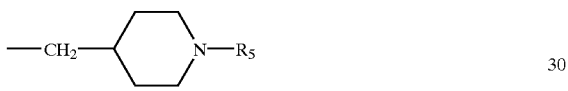

group, and
$R_5$ represents a $C_1$–$C_3$ alkyl group, a —$(CH_2)_m$—$CH_2OH$ group, a (2-pyridinyl)methyl group or a 4-(aminoiminomethyl)benzoyl group,
$R_6$ represents a methyl group or forms, with $R_5$ and the nitrogen to which they are bonded, a 5- or 6-membered saturated heterocycle.

"Ambient temperature" is understood as meaning a temperature of the order of 15 to 25° C., and "temperature close to ambient temperature" as meaning a temperature of approximately 0 to 40° C.

A general method of preparation of the compounds of the formula I, which is recommended according to the invention, comprises: according to a first variant A, the steps consisting of:

(1) reacting an 8-hydroxyquinoline derivative of formula II:

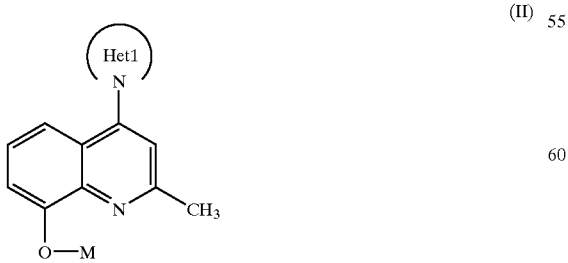

in which:
Het1 represents a five-membered nitrogen-containing heterocycle comprising in total 1, 2, 3 or 4 nitrogen atoms and M represents an alkali metal, especially sodium or potassium,
with a compound of formula III:

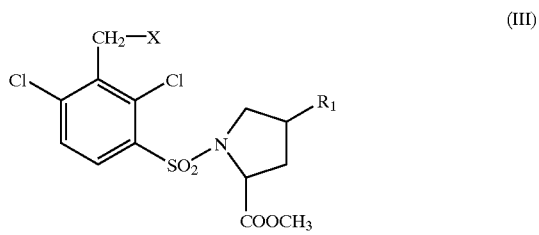

in which:
X represents a halogen atom, preferably a bromine atom, and
$R_1$ represents a hydrogen atom or an OH group, an alkoxy group or a phenoxy group,
in an anhydrous solvent such as, for example, dimethylformamide, at a temperature of between 0 and 50° C., for 0.5 to 10 hours, in order to obtain a compound of formula IV:

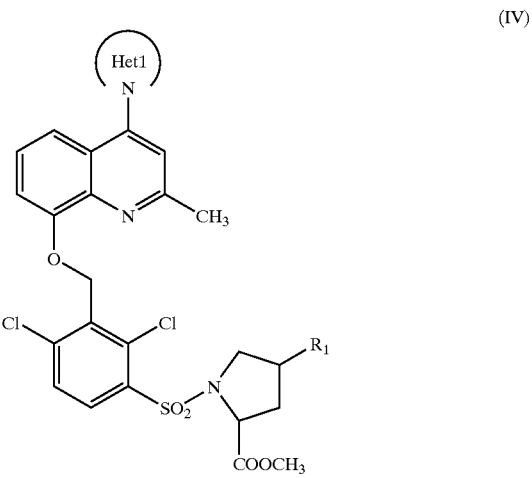

in which:
Het1 and $R_1$ retain the same meaning as previously;
(2) hydrolysing the ester function of the compound of formula IV thus obtained according to step (1) above, especially by reaction with an aqueous solution of sodium hydroxide, in a miscible solvent such as, for example, dioxane, at a temperature of the order of 20 to 60° C. and for 1 to 5 hours, in order to obtain, after acidification, a compound of formula V:

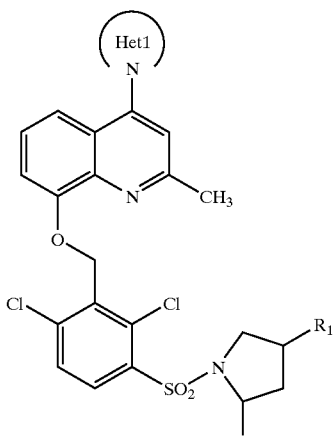

(V)

in which:
Het1 and R₁ retain the same meaning as above;
(3) reacting the compound of formula V thus obtained with an amine of formula:

HNR₃R₄     (VI)

in which:
$R_3$ represents a hydrogen atom or a $C_1$-$C_3$ alkyl group,
$R_4$ represents a hydrogen atom, a $C_1$-$C_3$ alkyl, —(CH₂)$_n$—CH₂OH, —(CH₂)$_n$—COOR₁₁, —(CH₂)$_n$—CH₂—NR₅R₆,

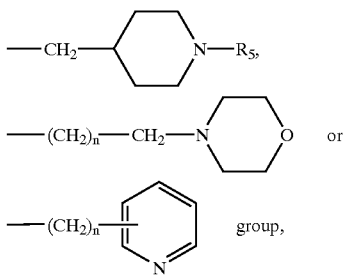

group, $R_5$ represents a $C_1$-$C_3$ alkyl, —(CH₂)$_m$—CH₂OH, —(CH₂)$_m$—COOR₁₁, —(CH₂)$_m$—CH₂—O—(CH₂)$_m$—CH₂OH group, or an amino-protecting group such as, for example, a 1,1-dimethylethoxycarbonyl (BOC) group, ($R_5$ and $R_6$ not simultaneously being amino-protecting groups),
$R_6$ represents a $C_1$-$C_3$ alkyl group or an amino-protecting group, for example of the BOC type,
$R_{11}$ represents a protecting group of the acid function, which is easily hydrolysable such as, for example, the t-butyl (or 1,1-dimethylethyl) group,
n=1, 2, 3 or 4,
m=1, 2 or 3,
in an appropriate solvent, in particular dichloromethane, in the presence of activators such as, in particular, 1-hydroxy-7-azabenzotriazole (HOAT) and 1-[3-(dimethylaminopropyl)-3-ethy]carbodiimide hydrochloride (EDCI), at a temperature close to ambient temperature (0–40° C., preferably 10–35° C.), for 2 to 50 hours, in order to obtain a compound of formula:

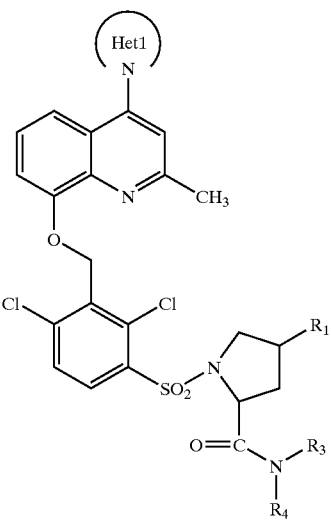

(VII)

in which
Het1, R₁, R₃, R₄ keep the same meaning as previously; and
(4) if necessary, reacting the compound of formula VII thus obtained in order to remove the amino- or acido-protecting groups in such a way as to replace these groups by a hydrogen atom, for example by reaction of the said compound VII with trifluoroacetic acid in order to remove an amino-protecting group of the BOC type or in order to remove an acido-protecting group of the t-butyl type, in such a way as to obtain the compound of formula I:

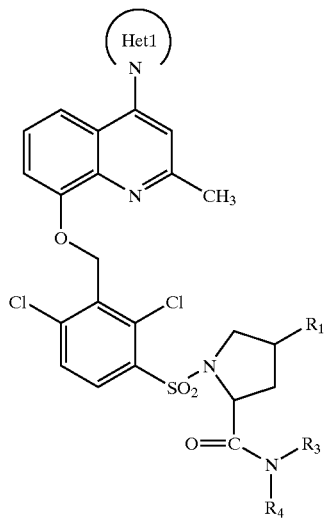

(I)

in which:
Het1, R₁, R₃ and R₄ keep the same meaning as above, with the exception of the protecting groups replaced by hydrogen atoms; then,
(5) if necessary, reacting the compound of formula I thus obtained with an acid in order to obtain the corresponding acid addition salt;
according to a second variant B consisting of:
(1) reacting a compound of formula I such as obtained in step (4) of variant A above,

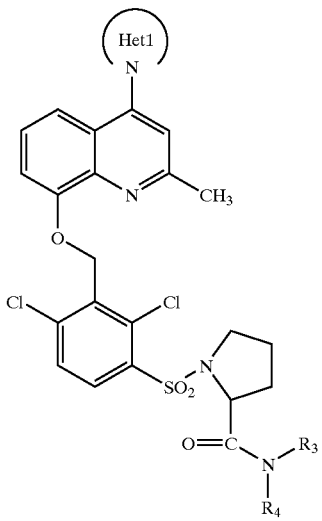

in which:
Het1 represents a 1-imidazolyl group, a 1-pyrazolyl group or a 1-(1,2,4-triazolyl) group,
$R_3$ represents H, or a $C_1-C_3$ alkyl group,
$R_4$ represents a group which carries a primary or secondary amine function chosen from: $-(CH_2)_n-CH_2-NHR_6$ or

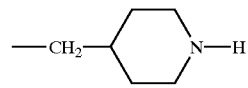

where $R_6$ represents H or an alkyl group and n represents 1, 2, 3 or 4, with a halogenated compound of formula: $Y-(CH_2)_m-CH_2OR_{13}$, $Y-(CH_2)_m-COOR_{11}$, or $Y-(CH_2)_m-CH_2-O-(CH_2)_m-CH_2OR_{13}$, where
Y is a halogen, preferentially Br or I,
m represents 1, 2 or 3
$R_{11}$ is an acido-protecting group, such as, for example, t-butyl, and
$R_{13}$ is a protecting group of the alcohol function, in particular the acetyl group, in a solvent such as, for example, dimethylformamide or acetonitrile, in the presence of an agent with alkaline character, such as, for example, potassium carbonate, at a temperature close to ambient temperature and for 5 to 20 hours, in order to obtain the compound of formula VII:

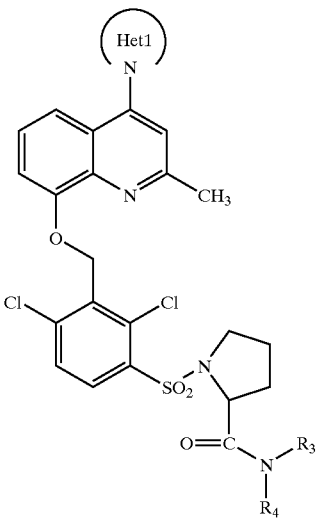

in which:
$R_3$ represents H or a $C_1-C_3$ alkyl group,
$R_4$ represents a $-(CH_2)_n-CH_2-NR_5R_6$ or

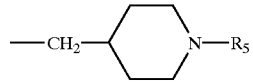

group where
$R_5$ represents group: $-(CH_2)_m-CH_2OR_{13}$, $-(CH_2)_m-COOR_{11}$, or $-(CH_2)_m-CH_2-O-(CH_2)_m-CH_2OR_{13}$,
Het1, $R_6$, $R_{11}$ and $R_{13}$ keep the same meaning as above;

(2) carrying out a deprotection reaction of each alcohol or acid group in order to replace the $R_{13}$ and $R_{11}$ groups by a hydrogen atom, and to thus obtain the corresponding compounds of formula I;

(3) if necessary, reacting the compound of formula I thus obtained with an inorganic or organic acid in order to obtain the corresponding salt;

according to a third variant C, the steps consisting of:
(1) reacting the acid chloride of formula VIII:

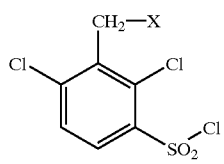

in which:
X represents a halogen, preferentially bromine,
with a heterocyclic derivative corresponding to the formula:

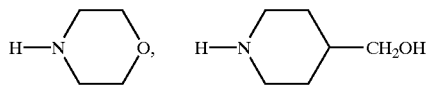

-continued or 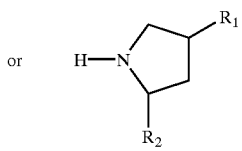

where:

$R_1$ represents H, OH, alkoxy, phenoxy, phenylmethoxy, $CH_2OH$, $C_3$–$C_8$ cycloalkyloxy or cycloalkylalkoxy where the cycloalkyl fragment is $C_3$–$C_8$ and the alkoxy fragment $C_1$–$C_4$, $R_2$ represents H, or a —$CH_2OH$, —$CH_2OCH_3$, —$CONH(CH_2)_nCH_2NR_5R_{12}$, —$CONH(CH_2)_nCH_2OH$, —$CONH(CH_2)_nCOOR_{11}$ or

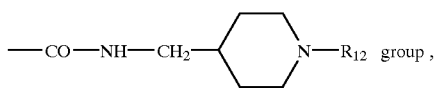

n=1, 2, 3 or 4, $R_5$ represents H or an alkyl group, $R_{11}$ represents an acido-protecting group, and $R_{12}$ represents an amino-protecting group, in a solvent such as, for example, acetonitrile, in the presence of a base such as, for example, potassium carbonate or triethylamine, at a temperature close to ambient temperature, for 10 to 30 hours, in order to obtain a compound of formula IX:

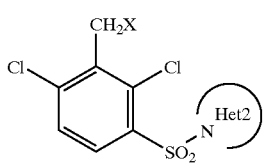
(IX)

in which:

Het2 represents a

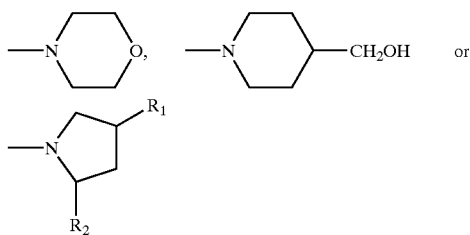

group, and X, $R_1$, $R_2$, $R_{11}$, $R_{12}$ and n keep the same meaning as above;

(2) reacting the compound of formula IX thus obtained with an 8-hydroxy-quinoline derivative of formula II:

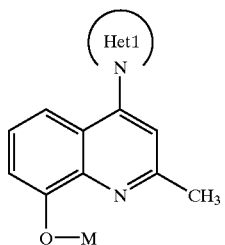
(II)

in which:

Het1 represents a 5-membered nitrogen-containing heterocycle comprising 1, 2, 3 or 4 nitrogen atoms and M represents an alkali metal, in particular sodium or potassium, under conditions analogous to those employed in step (1) of the preceding variant A, in order to obtain a compound of formula X:

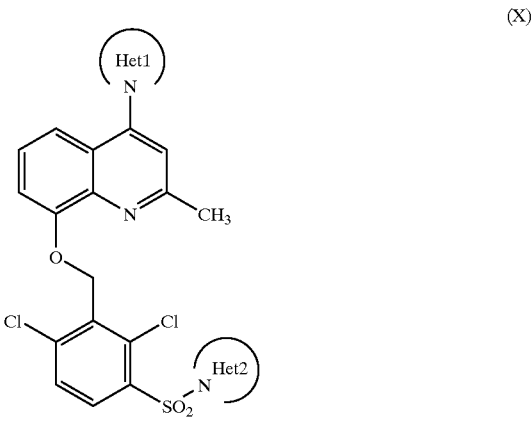
(X)

in which:

Het1 and Het2 retain the same meaning as above;

(3) if necessary, carrying out a deprotection reaction, for example by the action of trifluoroacetic acid, in order to replace each $R_{11}$, or $R_{12}$ protecting group of the acid or amine functions by a hydrogen atom, in order to obtain a compound of formula I:

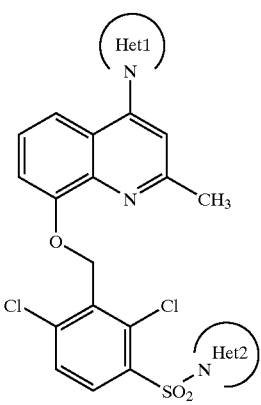

in which:

Het1 retains the same meaning as above, and

Het2 represents a

—N(morpholine)O, —N(piperidine)CH₂OH or

—N(pyrrolidine with R₁, R₂) group,

R₁ has the same meaning as above,
R₂ represents a —CH₂OH, —CH₂OCH₃, —CONH(CH₂)$_n$CH₂NHR₅, CONH(CH₂)$_n$CH₂OH, —CONH(CH₂)$_n$COOH or —CO—NH—CH₂—(piperidine)N—H group n=1, 2, 3 or 4, and
R₅ represents H or an alkyl group; and (4) if necessary, reacting the compound of formula I thus obtained with an acid in order to obtain the corresponding salt.

The invention will be better understood on reading (i) examples of preparation and (ii) results of pharmacological tests carried out with the compounds according to the invention, which will follow. Of course, both these elements together are not limiting but are given by way of illustration.

In the case of compounds having an asymmetric carbon in their structure, the absence of particular indication or the comment (R,S) signifies that racemic compounds are concerned; in the case of compounds having chirality, this is indicated immediately following the indexation of the substituent carried by the said asymmetric carbon; the (R) or (S) signs are then used, in accordance with the Cahn, Ingold and Prelog rules. The nomenclature used in the examples is that recommended by Chemical Abstracts: thus certain derivatives of L-proline can become, after reaction of the acid function with an amine, derivatives of 2(S)-pyrrolidinecarboxamide.

Preparation I

1-[[2,4-Dichloro-3-[[[4-(1H-imidazol-1-yl)-2-methyl-8-quinolinyl]oxy]methyl]-phenyl]sulphonyl]-L-proline, methyl ester A solution of 0.7 g (3.11×10⁻³ mol) of 8-hydroxy-4-[1H-imidazol-1-yl]-2-methylquinoline is prepared in 20 ml of dimethylformamide (DMF) and 0.11 g (3.42×10⁻³ mol) of 75% sodium hydride in oil is added. After 10 minutes with stirring at ambient temperature, 1.47 g (3.42×10⁻³ mol) of the methyl ester of N-[3-(bromomethyl)-2,4-dichlorophenylsulphonyl]-L-proline are added. After 15 hours with stirring at ambient temperature, the reaction mixture is hydrolysed on iced water and extracted with ethyl acetate. The organic phase is washed with water, dried over magnesium sulphate and then concentrated under reduced pressure. The residue obtained is purified by chromatography on silica gel eluting with the aid of a toluene/propanol mixture (95/5; v/v). 1.07 g of the expected product are thus obtained in the form of a beige solid (yield=68%).

M.p.=100° C.
$[\alpha]^{27}_D$=−14.4° (c=0.33; CH₃OH)

Preparation II

1-[[2,4-Dichloro-3-[[[4-(1H-imidazol-1-yl)-2-methyl-8-quinolinyl]oxy]methyl]-phenyl]sulphonyl]-L-proline 1.6 ml (1.6×10⁻³ mol) of a normal solution of sodium hydroxide in water are added to a solution of 0.44 g (0.763×10⁻³ mol) of the compound obtained according to Preparation I in 30 ml of dioxane. The reaction mixture is heated to gentle reflux for 8 hours and the solvent is then driven off under reduced pressure. The residue is taken up again in water and the solution is gently acidified to pH 4.5 with the aid of a solution of hydrochloric acid. The expected acid precipitates. The precipitate is filtered, washed with water on the filter and dried at 40° C. under reduced pressure. 0.36 g of the expected product is thus obtained in the form of white powder (Yield=89%).

M.p.=172° C.

EXAMPLE 1

1-[[2,4-Dichloro-3-[[[4-(1H-imidazol-1-yl)-2-methyl-8-quinolyl]oxy]methyl]-phenyl]sulphonyl]-N-methyl-2-(S)-pyrrolidinecarboxamide A solution of 0.35 g (0.633×10⁻³ mol) of acid obtained according to Preparation II is prepared in 25 ml of dichloromethane and 0.13 g (0.686×10⁻³ mol) of 1-(3-dimethylaminopropyl)-3-ethylcarbodiimide hydrochloride (EDCl), 0.1 g (0.686×10⁻³ mol) of 1-hydroxy-7-azabenzotriazole (HOAT), 0.138 g (1.37×10⁻³ mol) of triethylamine, then 0.05 g (0.748×10⁻³ mol) of methylamine hydrochloride are added. The reaction mixture is stirred at ambient temperature for 20 hours. It is then hydrolysed in cold water and extracted with dichloromethane. The organic phase is dried over magnesium sulphate and then concentrated under reduced pressure. The residue is purified by chromatography on silica gel eluting with the aid of a dichloromethane/methanol (98/2; v/v) mixture. 0.29 g of the expected product is thus obtained in the form of an ecru solid (yield=81%).

M.p.=90° C.
$[\alpha]^{27}_D$=−28° (c=0.46; CH₃OH)

EXAMPLE 2

1-[[2,4-Dichloro-3-[[[4-(1H-imidazol-1-yl)-2-methyl-8-quinolyl]oxy]methyl]-phenyl]sulphonyl]-N-methyl-2-(S)-pyrrolidinecarboxamide, tartrate A solution of 0.28 g (0.487×10⁻³ mol) of the compound obtained according to Example 1 is prepared in 3 ml of methanol and 0.073 g (0.487×10⁻³ mol) of L-tartaric acid is added. The reaction mixture is kept with stirring at ambient temperature for 10 minutes and then concentrated under reduced pressure. The residue is redissolved in 10 ml of distilled water and the solution obtained is lyophilized. 0.34 g of the expected salt is thus obtained in the form of a fine and light white solid (Yield=96%).

M.p.=119° C.
$[\alpha]^{27}_D$=−19° (c=0.45; CH₃OH)

Preparation III

N-(3-Aminopropyl)-4-cyanobenzamide, trifluoroacetate

A solution of 51 g (0.168 mol) of [3-[(4-cyanobenzoyl)amino]-propyl]carbamic acid, 1,1-dimethylethyl ester is prepared in 300 ml of dichloromethane and 25 ml of trifluoroacetic acid are added, at 0° C., with stirring. The reaction mixture is brought back to ambient temperature and kept for 4 hours with stirring. The mixture is concentrated under reduced pressure and the residue is taken up in ethyl ether. The expected product crystallizes. It is filtered, washed with a little ethyl ether on the filter and dried under reduced pressure. 52 g of the product are thus obtained in the form of white crystals (Yield=97%).

M.p.=160° C.

Preparation IV

N-[3-[(4-Cyanobenzoyl)amino]propyl]-1-[[2,4-dichloro-3-[[[4-(1H-imidazol-1-yl)-2-methyl-8-quinolinyl]oxy]methyl]phenyl]sulphonyl]-2(S)-pyrrolidine-carboxamide Working analogously to Example 1, starting from the compounds obtained according to Preparations II and III, the expected product is obtained in the form of a beige solid (Yield=81%).

M.p.=118° C.

$[\alpha]^{27}_D=-33.2°$ (c=0.32; $CH_3OH$)

Preparation V

N-[3-[[4-[Amino(hydroxyimino)methyl]benzoyl]amino]propyl]-1-[[2,4-dichloro-3-[[[4-(1H-imidazol-1-yl)-2-methyl-8-quinolinyl]oxy]methyl-phenyl]sulphonyl]-2(S)-pyrrolidinecarboxamide A solution of 0.058 g ($0.843 \times 10^{-3}$ mol) of hydroxylamine hydrochloride is prepared in 2 ml of DMSO and 0.170 g ($1.69 \times 10^{-3}$ mol) of triethylamine, then 0.36 g ($0.48 \times 10^{-3}$ mol) of the compound obtained according to Preparation IV, are added. The reaction mixture is kept with stirring at ambient temperature for 1 hour, and then the same quantity of hydroxylamine hydrochloride and triethylamine is added again. After 15 hours with stirring at ambient temperature, the reaction mixture is poured onto water. The precipitate formed is separated by filtration, and then washed with water and dried under reduced pressure at 30° C. 0.37 g of the expected product is thus obtained in the form of a white powder (Yield=98%).

M.p.=160° C.

$[\alpha]^{27}_D=-22.5°$ (c=0.35; $CH_3OH$)

Preparation VI

N-[3-[[4-[[(Acetyloxy)imino]aminomethyl]benzoyl]amino]propyl]-1-[[2,4-dichloro-3-[[[4-(1H-imidazol-1-yl)-2-methyl-8-quinolinyl]oxy]methyl]-phenyl]sulphonyl]-2(S)-pyrrolidinecarboxamide A suspension of 0.32 g ($0.41 \times 10^{-3}$ mol) of the compound obtained according to Preparation V is prepared in 10 ml of dichloromethane and 0.134 g ($1.23 \times 10^{-3}$ mol) of acetic anhydride is added. The mixture is stirred for 3 hours at ambient temperature and then 0.134 g of acetic anhydride is added again and the mixture is stirred for 15 hours. The reaction mixture is hydrolysed and extracted with dichloromethane. The organic phase is washed with water and then dried over magnesium sulphate and concentrated under reduced pressure. 0.32 g of the expected product is thus obtained in the form of a white solid (Yield=95%).

M.p.=96° C.

$[\alpha]^{27}_D=-20.3°$ (c=0.32; $CH_3OH$)

EXAMPLE 3

N-[3-[[4-(Aminoiminomethyl)benzoyl]amino]propyl]-1-[[2,4-dichloro-3-[[[4-(1H-imidazol-1-yl)-2-methyl-8-quinolinyl]oxy]methyl]phenyl]sulphonyl]-2(S)-pyrrolidinecarboxamide A solution of 0.31 g ($0.377 \times 10^{-3}$ mol) of the compound obtained according to Preparation VI is prepared in 20 ml of methanol and 0.12 g of Lindlar catalyst (with 5% of palladium) is added. The mixture is stirred under a hydrogen atmosphere at atmospheric pressure and ambient temperature for 6 hours. The catalyst is removed by filtration and then the filtrate is concentrated under reduced pressure. The residue is taken up with water and the solution obtained is brought to a slightly alkaline pH with the aid of 1N sodium hydroxide. The white precipitate formed is filtered, washed with water and then dried under reduced pressure. Purification of this product is then carried out by chromatography on $NH_2$ grafted silica gel (Lichroprep® $NH_2$), eluting with the aid of a dichloromethane/methanol (98/2; v/v) mixture. 0.19 g of the expected product is thus obtained in the form of a yellow solid (Yield=66%).

M.p.=148° C.

$[\alpha]^{27}_D=-28.3°$ (c=0.36; $CH_3OH$)

EXAMPLE 4

N-[3-[[4-(Aminoiminomethyl)benzoyl]amino]propyl]-1-[[2,4-dichloro-3-[[[4-(1H-imidazol-1-yl)-2-methyl-8-quinolinyl]oxy]methyl]phenyl]sulphonyl]-2(S)-pyrrolidinecarboxamide, bis methanesulphonate A solution of 0.17 g ($0.22 \times 10^{-3}$ mol) of the compound obtained according to Example 3 is prepared in 4 ml of methanol and 0.0428 g ($0.44 \times 10^{-3}$ mol) of methanesulphonic acid is added. The reaction mixture is stirred for 10 min at ambient temperature and then concentrated under reduced pressure. The residue is redissolved in distilled water; the solution obtained is filtered and then lyophilized. 0.16 g of the expected product is thus obtained in the form of a white fluffy solid (Yield=75%).

M.p.=176° C.

$[\alpha]^{28}_D=-28.3°$ (c=0.32; $CH_3OH$)

Preparation VII

1-[[3-(Bromomethyl)-2,4-dichlorophenyl]sulphonyl]-2(S)-pyrrolidinemethanol

A solution of 1 g ($2.95 \times 10^{-3}$ mol) of 3-bromomethyl-2,4-dichlorobenzenesulphonyl chloride is prepared in 10 ml of acetonitrile and 4 ml of water. 292 $\mu l$ ($2.95 \times 10^{-3}$ mol) of L-(+)-prolinol and a solution of 886 mg of potassium carbonate in 4 ml of water are added. After 20 hours with stirring at ambient temperature, the reaction mixture is poured onto water and extracted with ethyl acetate. The organic phase is washed with water, dried over magnesium sulphate and concentrated under reduced pressure. 1.2 g of crude product are obtained which are purified by chromatography on silica gel eluting with a toluene/ethyl acetate (80/20; v/v). mixture. 0.92 g of the expected product is thus obtained in the form of a colourless oil (Yield=77%).

$[\alpha]^{26}_D=-16.5°$ (c=0.5; $CH_3OH$)

EXAMPLE 5

1-[[2,4-Dichloro-3-[[[4-(1H-imidazol-1-yl)-2-methyl-8-quinolinyl]oxy]methyl]-phenyl]sulphonyl]-2(S)-pyrrolidinemethanol Working analogously to Preparation I, starting from 8-hydroxy-4-(1H-imidazol-1-yl)-2-methylquinoline and the compound obtained according to Preparation VII, the expected product is obtained in the form of white crystals (Yield=35%).

M.p.=76° C.

$[\alpha]^{26}_D=-14.9°$ (c=0.8; CH$_3$OH)

EXAMPLE 6

1-[[2,4-Dichloro-3-[[[4-(1H-imidazol-1-yl)-2-methyl-8-quinolinyl]oxy]methyl]phenyl]sulphonyl]-2(S)-pyrrolidinemethanol, methanesulphonate Working analogously to Example 4, starting from the compound obtained according to Example 5 and from one molar equivalent of methanesulphonic acid, the expected product is obtained in the form of pale yellow crystals (Yield=90%).

M.p.=134° C.

$[\alpha]^{26}_D=+3.1°$ (c=0.84; CH$_3$OH)

EXAMPLE 7

1-[[2,4-Dichloro-3-[[[2-methyl-4-(1H-pyrazol-1-yl)-8-quinolinyl]oxy]methyl]-phenyl]sulphonyl]-2(S)-pyrrolidinemethanol Working analogously to Example 5, starting from 8-hydroxy-2-methyl-4-(1H-pyrazol-1-yl)quinoline, the expected product is obtained in the form of white crystals (Yield=77%).

M.p.=65° C.

$[\alpha]^{26}_D=-14.9°$ (c=0.7; CH$_3$OH)

EXAMPLE 8

1-[[2,4-Dichloro-3-[[[2-methyl-4-(1H-pyrazol-1-yl)-8-quinolinyl]oxy]methyl]-phenyl]sulphonyl]-2(S)-pyrrolidinemethanol, methanesulphonate Working analogously to Example 6, starting from the compound obtained according to Example 7, the expected salt is obtained in the form of yellow crystals (Yield=99%).

M.p.=120° C.

$[\alpha]^{26}_D=+11.2°$ (c=0.75; CH$_3$OH)

Preparation VIII

4-[[[[1-[(Phenylmethoxy)carbonyl]-2(S)-pyrrolidinyl]carbonyl]amino]methyl]-1-piperidinecarboxylic acid, 1,1-dimethylethyl ester Working analogously to Example 1, starting from N-[(phenyl-methoxy)carbonyl]-L-proline and 4-(aminomethyl)-1-piperidinecarboxylic acid, 1,1-dimethylethyl ester, the expected product is obtained in the form of a creamy white solid (Yield=99%).

M.p.=50° C.

$[\alpha]^{26}_D=-31°$ (c=0.80; CH$_3$OH)

Preparation IX

4-[[[(2(S)-Pyrrolidinyl)carbonyl]amino]methyl]-1-piperidinecarboxylic acid, 1,1-dimethylethyl ester (acetate)

A solution of 100.9 g (0.23 mol) of the compound obtained according to Preparation VIII is prepared in acetic acid. Under a nitrogen atmosphere, 96.4 ml (1.02 mol) of cyclohexadiene, and then 2 g of 10% palladium on carbon are added. The reaction mixture is heated at reflux for 5 hours. After cooling to 10–15° C., the reaction mixture is filtered and concentrated under reduced pressure. The residue is purified by chromatography on silica gel eluting with a dichloromethane/ethanol (6/4; v/v) mixture. 60 g of the expected product are thus obtained in the form of an orange oil (Yield=72%, expressed as salt with acetic acid).

$[\alpha]^{22}_D=-36,8°$ (c=0.63; CH$_3$OH)

Preparation X

4-[[[[1-[[3-(Bromomethyl)-2,4-dichlorophenyl]sulphonyl]-2(S)-pyrrolidinyl]-carbonyl]amino]methyl]-1-piperidinecarboxylic acid, 1,1-dimethylethyl ester Working analogously to Preparation VII, starting from 3-(bromomethyl)-2,4-dichlorobenzenesulphonyl chloride and the compound obtained according to Preparation IX, the expected product is obtained in the form of a white powder (Yield=97%).

M.p.=80° C.

$[\alpha]^{22}_D=-31°$ (c=0.92; CH$_3$OH)

Preparation XI

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidinecarboxylic acid, 1,1-dimethylethyl ester Working analogously to Preparation I, starting from the compound obtained according to Preparation X, the expected product is obtained in the form of a creamy white solid (Yield=44%).

M.p.=100° C.

$[\alpha]^{27}_D=-28.8°$ (c=0.36; CH$_3$OH)

EXAMPLE 9

1-[[2,4-Dichloro-3-[[[4-(1H-imidazol-1-yl)-2-methyl-8-quinolinyl]oxy]methyl]-phenyl]sulphonyl]-N-(4-piperidinylmethyl)-2(S)-pyrrolidinecarboxamide A solution of 6 g (7.92×10$^{-3}$ mol) of the compound obtained according to Preparation XI is prepared in 100 ml of dichloromethane and 0.856 g (7.92×10$^{-3}$ mol) of anisole is added. The mixture is cooled to 0° C. and 5 ml of trifluoroacetic acid are added. The solution is then stirred for 15 hours at ambient temperature, and then concentrated under reduced pressure. The residue is taken up with water and the solution obtained is brought to basic pH with a solution of normal sodium hydroxide. The mixture is extracted with ethyl acetate, and then the organic phase is dried over magnesium sulphate and concentrated. The crude product is purified by chromatography on silica gel eluting with the aid of a dichloromethane/methanol/ammonia (95/5/0.02; v/v/v) mixture. 4.4 g of the expected product are thus obtained in the form of a yellow solid (Yield=84%).

M.p.=150° C.

$[\alpha]^{22}_D=-47°$ (c=0.35; CH$_3$OH)

EXAMPLE 10

1-[[2,4-Dichloro-3-[[[4-(1H-imidazol-1-yl)-2-methyl-8-quinolinyl]oxy]methyl]-phenyl]sulphonyl]-N-(4-piperidinylmethyl)-2(S)-pyrrolidinecarboxamide, ditartrate Working analogously to Example 2, starting from the compound obtained according to Example 9 and using 2 mol of tartaric acid per mole of the said compound, the expected product is obtained in the form of a white fluffy solid (Yield=81%).

M.p.=145° C.

$[\alpha]^{27}_D$=−23.7° (c=0.31; $CH_3OH$)

Preparation XII

Acetic acid, 2-(2-iodoethoxy)ethyl ester

A solution of 2.4 g (14×10$^{-3}$ mol) of 2-(2-chloroethoxy) ethyl acetate is prepared in 60 ml of acetone and 22 g (0.144 mol) of sodium iodide are added. The reaction mixture is heated at reflux for 6 hours, and then concentrated under reduced pressure. The residue is taken up with water and ethyl acetate. The organic phase is dried over magnesium sulphate and concentrated under reduced pressure. 2.81 g of the expected product are thus obtained, which is used without other purification, in the form of an orangey oil (Yield=78%).

$n_D$=1.468

Preparation XIII

1-[[2,4-Dichloro-3-[[[4-(1H-imidazol-1-yl)-2-methyl-8-quinolinyl]oxy]methyl]-phenyl]sulphonyl]-N-[[1-[2-[2-(acetoxy)ethoxy]ethyl]-4-piperidinyl] methyl]-2(S)-pyrrolidinecarboxamide A mixture of 0.3 g (0.456×10$^{-3}$ mol) of the compound obtained according to Example 9 is prepared in 10 ml of acetonitrile and 4 ml of dimethylformamide. 95 mg (0.68× 10$^{-3}$ mol) of potassium carbonate and then 130 mg (0.5× 10$^{-3}$ mol) of the compound obtained according to Preparation XII are added dissolved in 2 ml of acetonitrile. The reaction mixture is kept with stirring at ambient temperature for 15 hours and then concentrated under reduced pressure. The residue is taken up with dichloromethane and the organic phase thus obtained is washed with water, dried over magnesium sulphate and concentrated under reduced pressure. The crude product is purified by chromatography on silica gel eluting with the aid of a dichloromethane/methanol/ammonia (9/1/0.02; v/v/v) mixture. 0.18 g of the expected product is thus obtained in the form of an ecru solid (Yield=50%).

M.p.=90° C.

$[\alpha]^{25}_D$=−35.8° (c=0.31; $CH_3OH$)

EXAMPLE 11

1-[[2,4-Dichloro-3-[[[4-(1H-imidazol-1-yl)-2-methyl-8-quinolinyl]oxy]methyl]-phenyl]sulphonyl]-N-[[1-[2-(2-hydroxyethoxy)ethyl]-4-piperidinyl] methyl]-2(S)-pyrrolidinecarboxamide A solution of 0.17 g (0.216×10$^{-3}$ mol) of the compound obtained according to Preparation XIII is prepared in 7 ml of methanol and 1 g of Amberlite® IRA 400 resin (in OH$^-$ form) is added. The reaction mixture is stirred at ambient temperature for 15 hours, and then filtered so as to remove the resin. After concentration of the filtrate under reduced pressure, 0.14 g of the expected product is obtained in the form of a white powdery solid (Yield=88%).

M.p.=96° C.

$[\alpha]^{25}_D$=−38.5° (c=0.32; $CH_3OH$)

EXAMPLE 12

1-[[2,4-Dichloro-3-[[[4-(1H-imidazol-1-yl)-2-methyl-8-quinolinyl]oxy]methyl]-phenyl]sulphonyl]-N-[[1-[2-(2-hydroxyethoxy)ethyl]-4-piperidinyl] methyl]-2(S)-pyrrolidinecarboxamide, tartrate Working analogously to Example 2, starting from the compound obtained according to Example 11, the expected salt is obtained in the form of a fluffy white product (Yield=99%).

M.p.=135° C.

$[\alpha]^{25}_D$=−38° (c=0.43; $CH_3OH$)

Preparation XIV

N-[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]glycine, 1,1-dimethyl-ethyl ester Working analogously to Example 1, starting from the compound obtained according to Preparation II and 1,1-dimethylethyl glycinate, the expected product is obtained in the form of a white solid (Yield=93%).

M.p.=110° C.

$[\alpha]^{22}_D$=−49° (c=0.3; $CH_3OH$)

EXAMPLE 13

N-[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]glycine, trifluoroacetate A mixture of 0.27 g (0.4×10$^{-3}$ mol) of the compound obtained according to Preparation XIV is prepared in 5 ml of dichloromethane and 43 mg (0.4×10$^{-3}$ mol) of anisole, and then, at 0° C., 1.5 ml of trifluoroacetic acid are added. The solution is stirred at 0° C. for 1 hour and then at ambient temperature for 24 hours. The reaction mixture is then concentrated under reduced pressure and the residue is triturated with ethyl ether. The solvent is removed with the soluble products and the residue is redissolved in distilled water. The solution is filtered, and then lyophilized. 0.285 g of the expected product is thus obtained in the form of a yellowish fine solid (Yield=86%).

M.p.=132° C.

$[\alpha]^{22}_D$=−9° (c=0.64; $CH_3OH$)

EXAMPLE 14

1-[[2,4-Dichloro-3-[[[4-(1H-imidazol-1-yl)-2-methyl-8-quinolinyl]oxy]methyl]-phenyl]sulphonyl]-N-[2-(dimethylamino)ethyl]-2(S)-pyrrolidinecarboxamide Working analogously to Example 1, starting from the compound obtained according to Preparation II and N,N-dimethylethylenediamine, the expected product is obtained in the form of a beige powder (Yield=40%).

M.p.=88° C.

$[\alpha]^{23}_D$=−44° (c=0.37; $CH_3OH$)

EXAMPLE 15

1-[[2,4-Dichloro-3-[[[4-(1H-imidazol-1-yl)-2-methyl-8-quinolinyl]oxy]methyl]-phenyl]sulphonyl]-N-[2-(dimethylamino)ethyl]-2(S)-pyrrolidinecarboxamide, tartrate Working analogously to Example 2, starting from the compound obtained according to Example 14, the expected product is obtained in the form of an off-white fluffy solid (Yield of 93%).

M.p.=132° C.

$[\alpha]^{24}_D$=−41° (c=0.58; $CH_3OH$)

EXAMPLE 16

1-[[2,4-Dichloro-3-[[[4-(1H-imidazol-1-yl)-2-methyl-8-quinolinyl]oxy]methyl]-phenyl]sulphonyl]-N-[3-(dimethylamino)propyl]-2(S)-pyrrolidinecarboxamide Working analogously to Example 1, starting from the compound obtained according to Preparation II and N,N- dimethyl-1,3-propanediamine, the expected product is obtained in the form of a white solid (Yield=40%).

M.p.=80° C.

$[\alpha]^{24}_D$=−47° (c=0.33; $CH_3OH$)

EXAMPLE 17

1-[[2,4-Dichloro-3-[[[4-(1H-imidazol-1-yl)-2-methyl-8-quinolinyl]oxy]methyl]-phenyl]sulphonyl]-N-[3-(dimethylamino)propyl]-2(S)-pyrrolidine-carboxamide, tartrate Working analogously to Example 2, starting from the compound obtained according to Example 16, the expected product is obtained in the form of a white solid (Yield=87%).

M.p.=131° C.

$[\alpha]^{24}_D$=−43° (c=0.42; CH OH)

EXAMPLE 18

1-[[2,4-Dichloro-3-[[[4-(1H-imidazol-1-yl)-2-methyl-8-quinolinyl]oxy]methyl]-phenyl]sulphonyl]-N-[4-(dimethylaminobutyl]-2(S)-pyrrolidinecarboxamide Working analogously to Example 1, starting from the compound obtained according to Preparation II and N,N-dimethyl-1,4-butanediamine, the expected product is obtained in the form of a white solid (Yield=51%).

M.p.=75° C.

$[\alpha]^{22}_D$=−49° (c=0.31; $CH_3OH$)

EXAMPLE 19

1-[[2,4-Dichloro-3-[[[4-(1H-imidazol-1-yl)-2-methyl-8-quinolinyl]oxy]methyl]-phenyl]sulphonyl]-N-[4-(dimethylamino)butyl]-2(S)-pyrrolidinecarboxamide, tartrate Working analogously to Example 2, starting from the compound obtained according to Example 18, the expected product is obtained in the form of a white fluffy solid (Yield=90%).

M.p.=125° C.

$[\alpha]^{24}_D$=−33° (c=0.35; $CH_3OH$)

EXAMPLE 20

1-[[2,4-Dichloro-3-[[[4-(1H-imidazol-1-yl)-2-methyl-8-quinolinyl]oxy]methyl]-phenyl]sulphonyl]-N-[(1-methyl-4-piperidinyl)methyl]-2(S)-pyrrolidine-carboxamide A mixture of 0.6 g (0.677×10$^{-3}$ mol) of the compound obtained according to Example 9 is prepared in 20 ml of dichloromethane and 0.15 g (1.49×10$^{-3}$ mol) of triethylamine is added, and then 0.08 g of paraformaldehyde and 0.37 g (27.1×10$^{-3}$ mol) of zinc chloride. The reaction mixture is kept with stirring for 1 hour, and then 0.1 g (2.64×10$^{-3}$ mol) of sodium borohydride and 2 ml of methanol are added. Stirring at ambient temperature is continued for 15 hours and then the mixture is concentrated under reduced pressure. The residue is taken up with water and the aqueous phase thus obtained is brought to alkaline pH with the aid of an ammonia solution and is extracted with ethyl acetate. The organic phase is dried and then concentrated under reduced pressure. The residue obtained is purified by chromatography on silica gel eluting with a dichloromethane/methanol/ammonia (95/5/0.2; v/v/v) mixture. 0.25 g of the expected product is thus obtained in the form of a white powder (Yield=55%).

M.p.=86° C.

$[\alpha]^{27}_D$=−36° (c=0.33; $CH_3OH$)

EXAMPLE 21

1-[[2,4-Dichloro-3-[[[4-(1H-imidazol-1-yl)-2-methyl-8-quinolinyl]oxy]methyl]-phenyl]sulphonyl]-N-[(1-methyl-4-piperidinyl)methyl]-2(S)-pyrrolidine-carboxamide, tartrate Working analogously to Example 2, starting from the compound obtained according to Example 20, the expected product is obtained in the form of a white solid (Yield=97%).

M.p.=135° C.

$[\alpha]^{27}_D$=−34.3° (c=0.58; $CH_3OH$)

Preparation XV

1-[[2,4-Dichloro-3-[[[4-(1H-imidazol-1-yl)-2-methyl-8-quinolinyl]oxy]methyl]-phenyl]sulphonyl]-N-[[1-[3-(acetoxy)propyl]-4-piperidinyl]methyl]-2(S)-pyrrolidinecarboxamide Working analogously to Preparation XIII, starting from the compound obtained according to Example 9 and 3-iodopropyl acetate, the expected product is obtained (Yield=52%).

M.p.=96° C.

$[\alpha]^{27}_D$=−32.2° (c=0.30; $CH_3OH$)

EXAMPLE 22

1-[[2,4-Dichloro-3-[[[4-(1H-imidazol-1-yl)-2-methyl-8-quinolinyl]oxy]methyl]-phenyl]sulphonyl]-N-[[1-(3-hydroxypropyl)-4-piperidinyl]methyl]-2(S)-pyrrolidinecarboxamide A solution of 0.13 g (0.167×10$^{-3}$ mol) of the compound obtained according to Preparation XV is prepared in 5 ml of methanol. 1 ml of water and 50 mg (0.385×10$^{-3}$ mol) of potassium carbonate are added. The mixture is stirred for 15 hours at ambient temperature and then concentrated under reduced pressure. The residue is taken up again in dichloromethane and the organic phase is washed with water and then dried over magnesium sulphate and concentrated under reduced pressure. The crude product is purified by chromatography on silica gel eluting with the aid of a dichloromethane/methanol (98/2;v/v) mixture. 0.09 g of the expected product is thus obtained in the form of a white fine solid (Yield=74%).

M.p.=90° C.

$[\alpha]^{27hd\ D}$=−35.5° (c=0.35; $CH_3OH$)

EXAMPLE 23

1-[[2,4-Dichloro-3-[[[4-(1H-imidazol-1-yl)-2-methyl-8-quinolinyl]oxy]methyl]-phenyl]sulphonyl]-N-[[1-(3-hydroxypropyl)-4-piperidinyl]methyl]-2(S)-pyrrolidinecarboxamide, tartrate Working analogously to Example 2, starting from the compound obtained according to Example 22, the expected product is obtained in the form of white powder (Yield=95%).

M.p.=145° C.
[α]$^{26}_D$=−10.4° (c=0.32; CH$_3$OH)

Preparation XVI

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidineacetic acid, 1,1-dimethylethyl ester A mixture of 0.45 g (0.684×10$^{-3}$ mol) of the compound obtained according to Example 9 is prepared in 4 ml of dimethylformamide and 30 ml of acetonitrile. 0.11 g (0.752×10$^{-3}$ mol) of potassium carbonate is added, and then 0.133 g (0.684×10$^{-3}$ mol) of t-butyl bromoacetate. The reaction mixture is kept with stirring at ambient temperature for 15 hours and then concentrated under reduced pressure. The residue is taken up again in water and the precipitate formed is extracted with ethyl acetate. The organic phase is washed with water and then dried and concentrated under reduced pressure. The crude product is purified by chromatography on silica gel eluting with the aid of a dichloromethane/methanol (98/2;v/v) mixture. 0.31 g of the expected product is thus obtained in the form of an ecru white solid (Yield=60%).

M.p.=100° C.
[α]$^{23}_D$=−40° (c=0.30; CH$_3$OH)

EXAMPLE 24

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidineacetic acid, bis trifluoroacetate Working analogously to Example 13, starting from the compound obtained according to Preparation XVI, the expected product is obtained in the form of a yellow light solid (Yield=90%).

M.p.=149° C.
[α]$^{21}_D$=−41° (c=0.40; CH$_3$OH)

Preparation XVII

1-[[2,4-Dichloro-3-[[[2-methyl-4-(1H-pyrazol-1-yl)-8-quinolinyl]oxy]methyl]-phenyl]sulphonyl]-L-proline, methyl ester Working analogously to Preparation I, starting from 8-hydroxy-4-(1H-pyrazol-1-yl)-2-methylquinoline, the expected product is obtained in the form of a white solid (Yield=96%).

M.p.=90° C.
[α]$^{25}_D$=−19° (c=0.50; CHCl$_3$)

Preparation XVIII

1-[[2,4-Dichloro-3-[[[2-methyl-4-(1H-pyrazol-1-yl)-8-quinolinyl]oxy]methyl]-phenyl]sulphonyl]-L-proline Working analogously to Preparation II, starting from the compound obtained according to Preparation XVII, the expected product is obtained in the form of an ecru white powder (Yield=91%).

M.p.=148° C.
[α]$^{27}_D$=+1° (c=0.40; DMSO)

Preparation XIX

4-[[[[1-[[2,4-Dichloro-3-[[[2-methyl-4-(1H-pyrazol-1-yl)-8-quinolinyl]oxy]-methyl]phenyl]sulphonyl]-2(S)-pyrrolidinyl]carbonyl]amino]methyl]-1-piperidinecarboxylic acid, 1,1-dimethylethyl ester Working analogously to Example 1, starting from the compound obtained according to Preparation XVIII and the t-butyl ester of 4-(aminomethyl)-1-piperidinecarboxylic acid, the expected product is obtained in the form of a white solid (Yield=52%).

M.p.=109° C.
[α]$^{25}_D$=−45° (c=0.44; CHCl$_3$)

EXAMPLE 25

1-[[2,4-Dichloro-3-[[[2-methyl-4-(1H-pyrazol-1-yl)-8-quinolinyl]oxy]methyl]-phenyl]sulphonyl]-N-(4-piperidinylmethyl)-2(S)-pyrrolidinecarboxamide, bis trifluoroacetate Working analogously to Example 13, starting from the compound obtained according to Preparation XIX, the expected product is obtained in the form of a white solid (Yield=89%).

M.p.=125° C.
[α]$^{26}_D$=−27° (c=0.30; CH$_3$OH)

Preparation XX

4-[[[[1-[[2,4-Dichloro-3-[[[2-methyl-4-(1H-1,2,4-triazol-1-yl)-8-quinolinyl]oxy]-methyl]phenyl]sulphonyl]-2(S)-pyrrolidinyl]carbonyl]amino]methyl]-1-piperidinecarboxylic acid, 1,1-dimethylethyl ester Working analogously to Preparation XI, starting from the compound obtained according to Preparation X and 8-hydroxy-2-methyl-4-(1H-1,2,4-triazol-1-yl)quinoline, the expected product is obtained in the form of a beige powder (Yield=93%).

M.p.=94° C.
[α]$^{24}_D$=−44° (c=0.57; CHCl$_3$)

EXAMPLE 26

1-[[2,4-Dichloro-3-[[[2-methyl-4-(1H-1,2,4-triazol-1-yl)-8-quinolinyl]oxy]-methyl]phenyl]sulphonyl]-N-(4-piperidinylmethyl)-2(S)-pyrrolidine-carboxamide, bis trifluoroacetate Working analogously to Example 25, starting from the compound obtained according to Preparation XX, the expected product is obtained in the form of a white-cream solid (Yield=89%).

M.p.=130° C.
[α]$^{18}_D$=−28° (c=0.63; CH$_3$OH)

Preparation XXI

1-[[2,4-Dichloro-3-[[[2-methyl-4-(1H-pyrazol-1-yl)-8-quinolinyl]oxy]methyl]-phenyl]sulphonyl]-N-[[1-[3-(acetoxy)propyl]-4-piperidinyl]methyl]-2(S)-pyrrolidinecarboxamide Working analogously to Preparation XV, starting from the compound obtained according to Example 25 and 3-iodopropyl acetate, the expected product is obtained in the form of a white solid (Yield=64%).

M.p.=89° C.
[α]$^{24}_D$=−41° (c=0.60; CHCl$_3$)

EXAMPLE 27

1-[[2,4-Dichloro-3-[[[2-methyl-4-(1H-pyrazol-1-yl)-8-quinolinyl]oxy]methyl]-phenyl]sulphonyl]-N-[[1-(3-hydroxypropyl)-4-piperidinyl]methyl]-2(S)-pyrrolidinecarboxamide Working analogously to Example 22, starting from the compound obtained according to Preparation XXI, the expected product is obtained in the form of a white fine powder (Yield=95%).

M.p.=112° C.

$[\alpha]^{24}_D$=−42° (c=0.38; CHCl$_3$)

EXAMPLE 28

1-[[2,4-Dichloro-3-[[[2-methyl-4-(1H-pyrazol-1-yl)-8-quinolinyl]oxy]methyl]-phenyl]sulphonyl]-N-[[1-(3-hydroxypropyl)-4-piperidinyl]methyl]-2(S)-pyrrolidinecarboxamide, tartrate Working analogously to Example 2, starting from the compound obtained according to Example 27, the expected product is obtained in the form of a white solid (Yield=99%).

M.p.=136° C.

$[\alpha]^{22}_D$=−39° (c=0.50; CH$_3$OH)

Preparation XXII

1-[[2,4-Dichloro-3-[[[2-methyl-4-(1H-1,2,4-triazol-1-yl)-8-quinolinyl]oxy]-methyl]phenyl]sulphonyl]-N-[[1-[3-(acetoxy)propyl]-4-piperidinyl]methyl]-2(S)-pyrrolidinecarboxamide Working analogously to Preparation XV, starting from the compound obtained according to Example 26 and 3-iodopropyl acetate, the expected product is obtained in the form of a creamy white solid (Yield=47%).

M.p.=120° C.

$[\alpha]^{26}_D$=−61° (c=0.4; CHCl$_3$)

EXAMPLE 29

1-[[2,4-Dichloro-3-[[[2-methyl-4-(1H-1,2,4-triazol-1-yl)-8-quinolinyl]oxy]-methyl]phenyl]sulphonyl]-N-[[1-(3-hydroxypropyl)-4-piperidinyl]methyl]-2(S)-pyrrolidinecarboxamide Working analogously to Example 22, starting from the compound obtained according to Preparation XXII, the expected product is obtained in the form of a white powder (Yield=83%).

M.p.=136° C.

$[\alpha]^{22}_D$=−48° (c=0.55; CHCl$_3$)

EXAMPLE 30

1-[[2,4-Dichloro-3-[[[2-methyl-4-(1H-1,2,4-triazol-1-yl)-8-quinolinyl]oxy]-methyl]phenyl]sulphonyl]-N-[[1-(3-hydroxypropyl)-4-piperidinyl]methyl]-2(S)-pyrrolidinecarboxamide, tartrate Working analogously to Example 2, starting from the compound obtained according to Example 29, the expected product is obtained in the form of a white powder (Yield=98%).

M.p.=123° C.

$[\alpha]^{23}_D$=−43° (c=0.48; CH$_3$OH)

Preparation XXIII

1-[[2,4-Dichloro-3-[[[4-(1H-imidazol-1-yl)-2-methyl-8-quinolinyl]oxy]methyl]-phenyl]sulphonyl]-N-[[1-[4-(acetoxy)butyl]-4-piperidinyl]methyl]-2(S)-pyrrolidinecarboxamide Working analogously to Preparation XV, starting from the compound obtained according to Example 9 and 4-iodobutyl acetate, the expected product is obtained (Yield=63%).

M.p.=86° C.

$[\alpha]^{22}_D$=−44° (c=0.86; CHCl$_3$)

EXAMPLE 31

1-[[2,4-Dichloro-3-[[[4-(1H-imidazol-1-yl)-2-methyl-8-quinolinyl]oxy]methyl]-phenyl]sulphonyl]-N-[[1-(4-hydroxybutyl)-4-piperidinyl]methyl]-2(S)-pyrrolidinecarboxamide Working analogously to Example 11, starting from the compound obtained according to Preparation XXIII, the expected product is obtained in the form of a white solid (Yield=96%).

M.p.=112° C.

$[\alpha]^{22}_D$=−49° (c=0.78; CHCl$_3$)

EXAMPLE 32

1-[[2,4-Dichloro-3-[[[4-(1H-imidazol-1-yl)-2-methyl-8-quinolinyl]oxy]methyl]-phenyl]sulphonyl]-N-[[1-(4-hydroxybutyl)-4-piperidinyl]methyl]-2(S)-pyrrolidinecarboxamide, tartrate Working analogously to Example 2, starting from the compound obtained according to Example 31, the expected product is obtained in the form of a white solid (Yield=96%).

M.p.=133° C.

$[\alpha]^{22}_D$=−41° (c=0.82; CH$_3$OH)

Preparation XXIV

4-[(3-Bromomethyl-2,4-dichlorophenyl)sulphonyl]morpholine

Working analogously to Preparation VII, starting from morpholine and 3-bromomethyl-2,4-dichlorobenzenesulphonyl chloride, the expected product is obtained in the form of a yellow solid (Yield=85%) (the product contains the chloromethylated analogue in part).

M.p.=128° C.

EXAMPLE 33

8-[[2,6-Dichloro-3-(4-morpholinylsulphonyl)phenyl]methoxy]-4-(1H-imidazol-1-yl)-2-methylquinoline Working analogously to Preparation I, starting from the product obtained according to Preparation XXIV and 8-hydroxy-4-(1H-imidazol-1-yl)-2-methylquinoline, the expected product is obtained in the form of a beige solid (Yield=34%).

M.p.=148° C.

EXAMPLE 34

8-[[2,6-Dichloro-3-(4-morpholinylsulphonyl)phenyl]methoxy]-4-(1H-imidazol-1-yl)-2-methylquinoline, trifluoroacetate Working analogously to Example 1, starting from trifluoroacetic acid and the compound obtained according to Example 33, the expected product is obtained in the form of a cream colour light powder (Yield=98%).

M.p.=93° C.

EXAMPLE 35

8-[[2,6-Dichloro-3-(4-morpholinylsulphonyl)phenyl]methoxy]-2-methyl-4-(1H-pyrazol-1-yl)quinoline Working analogously to Example 33, starting from 8-hydroxy-4-(1H-pyrazol-1-yl)-2-methylquinoline, the expected product is obtained in the form of an off-white solid (Yield=83%).

M.p.=178° C.

EXAMPLE 36

8-[[2,6-Dichloro-3-(4-morpholinylsulphonyl)phenyl]methoxy]-2-methyl-4-(1H-pyrazol-1-yl)quinoline, trifluoroacetate Working analogously to Example 34, starting from Example 35, the expected product is obtained in the form of a white solid (Yield=89%).

M.p.=110° C.

Preparation XXV

1-[(3-Bromomethyl-2,4-dichlorophenyl)sulphonyl]-4-(hydroxymethyl)-piperidine

Working analogously to Preparation XXIV, starting from 4-(hydroxymethyl)piperidine, the expected product is obtained in the form of a white powder (Yield=88%).

M.p.=121° C.

EXAMPLE 37

1-[[2,4-Dichloro-3-[[[4-(1H-imidazol-1-yl)-2-methyl-8-quinolinyl]oxy]methyl]-phenyl]sulphonyl]-4-piperidinemethanol Working analogously to Example 33, starting from the product obtained according to Preparation XXV and 8-hydroxy-4-(1H-imidazol-1-yl)-2-methylquinoline, the expected product is obtained in the form of a white solid (Yield=40%).

M.p.=100° C.

EXAMPLE 38

1-[[2,4-Dichloro-3-[[[4-(1H-imidazol-1-yl)-2-methyl-8-quinolinyl]oxy]methyl]-phenyl]sulphonyl]-4-piperidinemethanol, trifluoroacetate Working analogously to Example 34, starting from the product obtained according to Example 37, the expected product is obtained in the form of a white powder (Yield=98%).

M.p. =109° C.

EXAMPLE 39

1-[[2,4-Dichloro-3-[[[2-methyl-4-(1H-pyrazol-1-yl)-8-quinolinyl]oxy]methyl]-phenyl]sulphonyl]-4-piperidinemethanol Working analogously to Example 37, starting from the product obtained according to Preparation XXV and 8-hydroxy-2-methyl-4-(1H-pyrazol-1-yl)quinoline, the expected product is obtained in the form of a beige solid (Yield=74%).

M.p.=138° C.

EXAMPLE 40

1-[[2,4-Dichloro-3-[[[2-methyl-4-(1H-pyrazol-1-yl)-8-quinolinyl]oxy]methyl]-phenyl]sulphonyl]-4-piperidinemethanol, trifluoroacetate Working analogously to Example 34, starting from the product obtained according to Example 39, the expected product is obtained in the form of a creamy white powder (Yield=98%).

M.p.=90° C.

Preparation XXVI

1-[[2,4-Dichloro-3-[[[4-(1H-imidazol-1-yl)-2-methyl-8-quinolinyl]oxy]methyl]-phenyl]sulphonyl]-4(R)-hydroxy-L-proline, methyl ester Working analogously to Preparation I, starting from the methyl ester of N-[(3-bromomethyl-2,4-dichlorophenyl)sulphonyl]-4-(R)-hydroxy-(L)-proline, the expected product is obtained in the form of an ecru white solid (Yield=69%).

M.p.=78° C.

$[\alpha]^{22}_D$=+1° (c=0.66; $CH_3OH$)

Preparation XXVII

1-[[2,4-Dichloro-3-[[[4-(1H-imidazol-1-yl)-2-methyl-8-quinolinyl]oxy]methyl]-phenyl]sulphonyl]-4(R)-hydroxy-L-proline Working analogously to Preparation II, starting from the product obtained according to Preparation XXVI, the expected product is obtained in the form of a white solid (Yield=51%).

M.p.=140° C.

$[\alpha]^{27}_D$=+13° (c=0.38; $CH_3OH$)

Preparation XXVIII

4-[[[[1-[[2,4-Dichloro-3-[[[4-(1H-imidazol-1-yl)-2-methyl-8-quinolinyl]oxy]-methyl]phenyl]sulphonyl]-4(R)-hydroxy-2(S)-pyrrolidinyl]carbonyl]amino]-methyl]-1-piperidinecarboxylic acid, 1,1-dimethylethyl ester Working analogously to Example 1, starting from the acid obtained according to Preparation XXVII and the t-butyl ester of 4-(aminomethyl)piperidine-carboxylic acid, the expected product is obtained in the form of a white solid (Yield=65%).

M.p.=124° C.

$[\alpha]^{24}_D$=−6° (c=0.51; $CH_3OH$)

EXAMPLE 41

1-[[2,4-Dichloro-3-[[[4-(1H-imidazol-1-yl)-2-methyl-8-quinolinyl]oxy]methyl]-phenyl]sulphonyl]-4(R)-hydroxy-N-(4-piperidinemethyl)-2(S)-pyrrolidine-carboxamide Working analogously to Example 9, starting from the compound obtained according to Preparation XXVIII, the expected product is obtained in the form of a yellowish solid (Yield=80%).

M.p.=140° C.

$[\alpha]^{27}_D$=−3° (c=0.33; $CH_3OH$)

EXAMPLE 42

1-[[2,4-Dichloro-3-[[[4-(1H-imidazol-1-yl)-2-methyl-8-quinolinyl]oxy]methyl]-phenyl]sulphonyl]-4(R)-hydroxy-N-(4-piperidinemethyl)-2(S)-pyrrolidine-carboxamide, ditartrate Working analogously to Example 2, starting from the compound obtained according to Example 41 and two molar equivalents of tartaric acid, the expected product is obtained in the form of a yellow light solid (Yield=50%).

M.p.=156° C.
$[\alpha]^{27}_D$=+30° (c=0.38; DMSO)

EXAMPLE 43

1-[[1,2,4-Dichloro-3-[[[4-(1H-imidazol-1-yl)-2-methyl-8-quinolinyl]oxy]methyl]-phenyl]sulphonyl]-N-(2-hydroxyethyl)-2(S)-pyrrolidinecarboxamide Working analogously to Example 1, starting from the acid obtained according to Preparation II and 2-aminoethanol, the expected product is obtained in the form of a white solid (Yield=93%).
M.p.=120° C.
$[\alpha]^{27}_D$=−31° (c=0.37; CH$_3$OH)

EXAMPLE 44

1-[[2,4-Dichloro-3-[[[4-(1H-imidazol-1-yl)-2-methyl-8-quinolinyl]oxy]methyl]-phenyl]sulphonyl]-N-(2-hydroxyethyl)-2(S)-pyrrolidinecarboxamide, hemisulphate Working analogously to Example 2, starting from the compound obtained according to Example 43 and half a molar equivalent of sulphuric acid, the expected product is obtained in the form of a white powder (Yield=98%).
M.p.=140° C.
$[\alpha]^{27}_D$=−24° (c=0.35; CH$_3$OH)

EXAMPLE 45

1-[[2,4-Dichloro-3-[[[4-(1H-imidazol-1-yl)-2-methyl-8-quinolinyl]oxy]methyl]-phenyl]sulphonyl]-N,N-dimethyl-2(S)-pyrrolidinecarboxamide Working analogously to Example 1, starting from the acid obtained according to Preparation II and dimethylamine dissolved in ethanol, the expected product is obtained in the form of a white solid (Yield=69%).
M.p.=88° C.
$[\alpha]^{27}_D$=−8° (c=0.32; CH$_3$OH)

EXAMPLE 46

1-[[2,4-Dichloro-3-[[[4-(1H-imidazol-1-yl)-2-methyl-8-quinolinyl]oxy]methyl]-phenyl]sulphonyl]-N,N-dimethyl-2(S)-pyrrolidinecarboxamide, tartrate Working analogously to Example 2, starting from the compound obtained according to Example 45, the expected product is obtained in the form of a yellow fine powder (Yield=80%).
M.p.=121° C.
$[\alpha]^{24}_D$=+34° (c=0.37; CH$_3$OH)

EXAMPLE 47

1-[[2,4-Dichloro-3-[[[4-(1H-imidazol-1-yl)-2-methyl-8-quinolinyl]oxy]methyl]-phenyl]sulphonyl]-N-[2-(4-morpholinyl)ethyl]-2(S)-pyrrolidinecarboxamide Working analogously to Example 1, starting from the acid obtained according to Preparation II and 4-(2-aminoethyl)morpholine, the expected product is obtained in the form of white crystals (Yield=73%).
M.p.=100° C.
$[\alpha]^{24}_D$=−30° (c=0.62; CH$_3$OH)

EXAMPLE 48

1-[[2,4-Dichloro-3-[[[4-(1H-imidazol-1-yl)-2-methyl-8-quinolinyl]oxy]methyl]-phenyl]sulphonyl]-N-[2-(4-morpholinyl)ethyl]-2(S)-pyrrolidinecarboxamide, hemisulphate Working analogously to Example 44, starting from the compound obtained according to Example 47, the expected product is obtained in the form of white crystals (Yield=97%).
M.p.=145° C.
$[\alpha]^{25}_D$=−46° (c=0.75; CH$_3$OH)

EXAMPLE 49

1-[[2,4-Dichloro-3-[[[4-(1H-imidazol-1-yl)-2-methyl-8-quinolinyl]oxy]methyl]-phenyl]sulphonyl]-N-[3-(4-morpholinyl)propyl]-2(S)-pyrrolidinecarboxamide Working analogously to Example 1, starting from the acid obtained according to Preparation II and 4-(3-aminopropyl)morpholine, the expected product is obtained in the form of white crystals (Yield=69%).
M.p.=96° C.
$[\alpha]^{25}_D$=−32.5° (c=064; CH$_3$OH)

EXAMPLE 50

1-[[2,4-Dichloro-3-[[[4-(1H-imidazol-1-yl)-2-methyl-8-quinolinyl]oxy]methyl]-phenyl]sulphonyl]-N-[3-(4-morpholinyl)propyl]-2(S)-pyrrolidinecarboxamide, hemisulphate Working analogously to Example 44, starting from the compound obtained according to Example 49, the expected product is obtained in the form of white crystals (Yield=98%).
M.p.=150° C.
$[\alpha]^{25}_D$=−46.5° (c=0.84; CH$_3$OH)

Preparation XXIX

1-[[2,4-Dichloro-3-[[[2-methyl-4-(1H-1,2,4-triazol-1-yl)-8-quinolinyl]oxy]-methyl]phenyl]sulphonyl]-N-[[1-[2-[2-(acetoxy)ethoxy]ethyl]-4-piperidinyl]-methyl]-2(S)-pyrrolidinecarboxamide Working analogously to Preparation XIII, starting from the compound obtained according to Example 26, the expected product is obtained in the form of beige crystals (Yield=60%).
M.p.=86° C.
$[\alpha]^{26}_D$=−37.5° (c=0.78; CH$_3$OH)

EXAMPLE 51

1-[[2,4-Dichloro-3-[[[2-methyl-4-(1H-1,2,4-triazol-1-yl)-8-quinolinyl]oxy]-methyl]phenyl]sulphonyl]-N-[[1-[2-(2-hydroxyethoxy)ethyl]-4-piperidinyl]-methyl]-2(S)-pyrrolidinecarboxamide Working analogously to Example 11, starting from the compound obtained according to Preparation XXIX, the expected product is obtained in the form of white crystals (Yield=89%).

M.p.=82° C.

$[\alpha]^{27}_D$=−33.2° (c=0.76; CH$_3$OH)

EXAMPLE 52

1-[[2,4-Dichloro-3-[[[2-methyl-4-(1H-1,2,4-triazol-1-yl)-8-quinolinyl]oxy]-methyl]phenyl]sulphonyl]-N-[[1-[2-(2-hydroxyethoxy)ethyl]-4-piperidinyl]-methyl]-2(S)-pyrrolidinecarboxamide, methanesulphonate Working analogously to Example 4, starting from the compound obtained according to Example 51, the expected product is obtained in the form of pale yellow crystals (Yield=99%).

M.p.=135° C.

$[\alpha]^{26}_D$=−36° (c=0,70; CH$_3$OH)

Preparation XXX

N-[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]-β-alanine, 1,1-dimethylethyl ester Working analogously to Example 1, starting from the acid obtained according to Preparation II and the t-butyl ester of β-alanine, the expected product is obtained in the form of an ecru white solid (Yield=80%).

M.p.=68° C.

$[\alpha]^{27}_D$=−23° (c=0.41; CH$_3$OH)

EXAMPLE 53

N-[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]-β-alanine, trifluoroacetate Working analogously to Example 13, starting from the compound obtained according to Preparation XXX, the expected product is obtained in the form of a yellow fine solid (Yield=94%).

M.p.=113° C.

$[\alpha]^{27}_D$=−8° (c=0.44; CH$_3$OH)

Preparation XXXI

1-[[3-(Bromomethyl)-2,4-dichlorophenyl]sulphonyl]-2(S)-(methoxymethyl)-pyrrolidine Working analogously to Preparation VII, starting from 2(S)-(methoxy-methyl)pyrrolidine, the expected product is obtained in the form of a colourless oil (Yield=78%).

$[\alpha]^{26}_D$=−5.5° (c=0.73; CH$_3$OH)

EXAMPLE 54

1-[[2,4-Dichloro-3-[[[4-(1H-imidazol-1-yl)-2-methyl-8-quinolinyl)oxy]methyl]-phenyl]sulphonyl]-2(S)-(methoxymethyl)pyrrolidine Working analogously to Preparation I, starting from 8-hydroxy-4-(1H-imidazol-1-yl)-2-methylquinoline and the compound obtained according to Preparation XXXI, the expected product is obtained in the form of white crystals (Yield=44%).

M.p.=66° C.

$[\alpha]^{27}_D$=−31.5° (c=0.80; CH$_3$OH)

EXAMPLE 55

1-[[2,4-Dichloro-3-[[[4-(1H-imidazol-1-yl)-2-methyl-8-quinolinyl)oxy]methyl]-phenyl]sulphonyl]-2(S)-(methoxymethyl)pyrrolidine, methanesulphonate Working analogously to Example 4, starting from the compound obtained according to Example 54, the expected product is obtained in the form of pale yellow crystals (Yield=99%).

M.p.=123° C.

$[\alpha]^{26}_D$=+21° (c=0.85; CH$_3$OH)

EXAMPLE 56

1-[[2,4-Dichloro-3-[[[2-methyl-4-(1H-pyrazol-1-yl)-8-quinolinyl)oxy]methyl]-phenyl]sulphonyl]-2(S)-(methoxymethyl)pyrrolidine Working analogously to Example 54, starting from 8-hydroxy-2-methyl-4-(1H-pyrazol-1-yl)-quinoline, the expected product is obtained in the form of white crystals (Yield=73%).

M.p.=75° C.

$[\alpha]^{24}_D$=+1.6° (c=0.69; CH$_3$OH)

EXAMPLE 57

1-[[2,4-Dichloro-3-[[[2-methyl-4-(1H-pyrazol-1-yl)-8-quinolinyl)oxy]methyl]-phenyl]sulphonyl]-2(S)-(methoxymethyl)pyrrolidine, methanesulphonate Working analogously to Example 4, starting from the compound obtained according to Example 56, the expected product is obtained in the form of yellow crystals (Yield=97%).

M.p.=110° C.

$[\alpha]^{26}_D$=+36° (c=0.80; CH$_3$OH)

Preparation XXXII

1-[[2,4-Dichloro-3-[[[4-(1H-imidazol-1-yl)-2-methyl-8-quinolinyl]oxy]methyl]-phenyl]sulphonyl]-D-proline, methyl ester Working analogously to Preparation I, starting from the methyl ester of N-[[3-(bromomethyl)-2,4-dichlorophenyl]sulphonyl]-D-proline, the expected product is obtained in the form of a yellow solid (Yield=97%).

M.p.=74° C.

$[\alpha]^{22}_D$=+10° (c=0.60; CH$_3$OH)

Preparation XXXIII

1-[[2,4-Dichloro-3-[[[4-(1H-imidazol-1-yl)-2-methyl-8-quinolinyl]oxy]methyl]-phenyl]sulphonyl]-D-proline Working analogously to Preparation II, starting from the compound obtained according to Preparation XXXII, the expected product is obtained in the form of an ecru white solid (Yield=73%).

M.p.=175° C.

EXAMPLE 58

1-[[2,4-Dichloro-3-[[[4-(1H-imidazol-1-yl)-2-methyl-8-quinolyl]oxy]methyl]-phenyl]sulphonyl]-N-methyl-2(R)-pyrrolidinecarboxamide Working analogously to Example 1, starting from the compound obtained according to Preparation XXXIII, the expected product is obtained in the form of a white solid (Yield=83%).

M.p.=128° C.

$[\alpha]^{25}_D$=+25° (c=0.30; CH$_3$OH)

EXAMPLE 59

1-[[2,4-Dichloro-3-[[[4-(1H-imidazol-1-yl)-2-methyl-8-quinolyl]oxy]methyl]-phenyl]sulphonyl]-N-methyl-2(R)-pyrrolidinecarboxamide, tartrate Working analogously to Example 2, starting from the compound obtained according to Example 58, the expected product is obtained in the form of a yellow fine solid (Yield=80%).

M.p.=114° C.

$[\alpha]^{25}_D$=+25° (c=0.80; CH$_3$OH)

EXAMPLE 60

1-[[2,4-Dichloro-3-[[[4-(1H-imidazol-1-yl)-2-methyl-8-quinolinyl]oxy]methyl]-phenyl]sulphonyl]-N-[3-(dimethylamino)propyl]-N-methyl-2(S)-pyrrolidine-carboxamide Working analogously to Example 1, starting from N,N,N'-trimethyl-1,3-propanediamine, the expected product is obtained in the form of a white solid (Yield=64%).

M.p.=80° C.

$[\alpha]^{25}_D$=−16° (c=0.34; CH$_3$OH)

EXAMPLE 61

1-[[2,4-Dichloro-3-[[[4-(1H-imidazol-1-yl)-2-methyl-8-quinolinyl]oxy]methyl]-phenyl]sulphonyl]-N-[3-(dimethylamino)propyl]-N-methyl-2(S)-pyrrolidine-carboxamide, hemisulphate Working analogously to Example 48, starting from the compound obtained according to Example 60, the expected product is obtained in the form of a white fine solid (Yield=98%).

M.p.=133° C.

$[\alpha]^{25}_D$=−34° (c=0.40; CH$_3$OH)

EXAMPLE 62

1-[[2,4-Dichloro-3-[[[4-(1H-imidazol-1-yl)-2-methyl-8-quinolinyl]oxy]methyl]-phenyl]sulphonyl]-N-[[1-[2-(acetoxy)ethyl]-4-piperidinyl]methyl]-2(S)-pyrrolidinecarboxamide Working analogously to Preparation XV, starting from 2-bromoethyl acetate, the expected product is obtained in the form of a beige solid (Yield=38%).

M.p.=93° C.

$[\alpha]^{22}_D$=−48° (c=0.50; CHCl$_3$)

EXAMPLE 63

1-[[2,4-Dichloro-3-[[[4-(1H-imidazol-1-yl)-2-methyl-8-quinolinyl]oxy]methyl]-phenyl]sulphonyl]-N-[[1-(2-hydroxyethyl)-4-piperidinyl]methyl]-2(S)-pyrrolidinecarboxamide Working analogously to Example 11, starting from the compound obtained according to Example 62, the expected product is obtained in the form of an ecru white solid (Yield=88%).

M.p.=104° C.

$[\alpha]^{18}_D$=−53° (c=0.75; CHCl$_3$)

EXAMPLE 64

1-[[2,4-Dichloro-3-[[[4-(1H-imidazol-1-yl)-2-methyl-8-quinolinyl]oxy]methyl]-phenyl]sulphonyl]-N-[[1-(2-hydroxyethyl)-4-piperidinyl]methyl]-2(S)-pyrrolidinecarboxamide, hemisulphate Working analogously to Example 48, starting from the compound obtained according to Example 63, the expected product is obtained in the form, of a white solid (Yield=98%).

M.p.=160° C.

$[\alpha]^{22}_D$=−48° (c=0.54; CH$_3$OH)

EXAMPLE 64 A

1-[[2,4-Dichloro-3-[[[4-(1H-imidazol-1-yl)-2-methyl-8-quinolinyl]oxy]methyl]-phenyl]sulphonyl]-N-[[1-(2-hydroxyethyl)-4-piperidinyl]methyl]-2(S)-pyrrolidinecarboxamide, methanesulphonate Working analogously to Example 4, starting from the compound obtained according to Example 63, the expected product is obtained in the form of a pale yellow solid (Yield=99%).

M.p.=127° C.

$[\alpha]^{29}_D$=−46° (c=0.82; CH$_3$OH)

Preparation XXXIV

4-[[[[1-[[2,4-Dichloro-3-[[[2-methyl-4-(1H-1,2,4-triazol-1-yl)-8-quinolinyl]oxy]-methyl]phenyl]sulphonyl]-2(S)-pyrrolidinyl]carbonyl]amino]methyl]-1-piperidineacetic acid, 1,1-dimethylethyl ester Working analogously to Preparation XVI, starting from the compound obtained according to Example 26, the expected product is obtained in the form of a beige solid (Yield=58%).

M.p.=50° C.

$[\alpha]^{25}_D$=−40° (c=0.50; CHCl$_3$)

EXAMPLE 65

4-[[[[1-[[2,4-Dichloro-3-[[[2-methyl-4-(1H-1,2,4-triazol-1-yl)-8-quinolinyl]oxy]methyl]phenyl]sulphonyl]-2(S)-pyrrolidinyl]carbonyl]amino]methyl]-1-piperidineacetic acid, bis-trifluoroacetate Working analogously to Example 24, starting from the compound obtained according to Preparation XXXIV, the expected product is obtained in the form of an ecru white powder (Yield=96%).

M.p.=142° C.

$[\alpha]^{19}_D$=−37° (c=0.80; CH$_3$OH)

EXAMPLE 66

1-[[2,4-Dichloro-3-[[[4-(1H-imidazol-1-yl)-2-methyl-8-quinolinyl]oxy]methyl]-phenyl]sulphonyl]-2(S)-pyrrolidinecarboxamide Working analogously to Example 1, starting from the acid obtained according to Preparation II and ammonia introduced in gaseous form into the reaction mixture, the expected product is obtained in the form of a beige solid (Yield=98%).

M.p.=110° C.
[α]$^{27}_D$=−22.9° (c=0.31; CH$_3$OH)

EXAMPLE 67

1-[[2,4-Dichloro-3-[[[4-(1H-imidazol-1-yl)-2-methyl-8-quinolinyl]oxy]methyl]-phenyl]sulphonyl]-2(S)-pyrrolidinecarboxamide, tartrate Working analogously to Example 2, starting from the compound obtained according to Example 66, the expected product is obtained in the form of a yellow solid (Yield=97%).
M.p.=124° C.
[α]$^{27}_D$=−12.6° (c=0.41; CH$_3$OH)

EXAMPLE 68

N-Cyclopropyl-1-[[2,4-dichloro-3-[[[4-(1H-imidazol-1-yl)-2-methyl-8-quinolinyl]oxy]methyl]phenyl]sulphonyl]-2(S)-pyrrolidinecarboxamide Working analogously to Example 1, starting from cyclopropylamine, the expected product is obtained in the form of an ecru white solid (Yield=87%).
M.p.=108° C.
[α]$^{24}_D$=−19.2° (c=0.32; CH$_3$OH)

EXAMPLE 69

N-Cyclopropyl-1-[[2,4-dichloro-3-[[[4-(1H-imidazol-1-yl)-2-methyl-8-quinolinyl]oxy]methyl]phenyl]sulphonyl]-2(S)-pyrrolidinecarboxamide, hydrochloride Working analogously to Example 2, starting from the compound obtained according to Example 68 and a solution of hydrogen chloride in methanol, the expected product is obtained in the form of a yellow powder (Yield=100%).
M.p.=160° C.
[α]$^{24}_D$=−10.9° (c=0.36; CH$_3$OH)

EXAMPLE 70

N-(Cyclopropylmethyl)-1-[[2,4-dichloro-3-[[[4-(1H-imidazol-1-yl)-2-methyl-8-quinolinyl]oxy]methyl]phenyl]sulphonyl]-2(S)-pyrrolidinecarboxamide Working analogously to Example 1, starting from (aminomethyl)-cyclopropane, the expected product is obtained in the form of a white solid (Yield=98%).
M.p.=100° C.
[α]$^{24}_D$=−22.4° (c=0.42; CH$_3$OH)

EXAMPLE 71

N-(Cyclopropylmethyl)-1-[[2,4-dichloro-3-[[[4-(1H-imidazol-1-yl)-2-methyl-8-quinolinyl]oxy]methyl]phenyl]sulphonyl]-2(S)-pyrrolidinecarboxamide, hydrochloride Working analogously to Example 69, starting from the compound obtained according to Example 70, the expected product is obtained in the form of a yellow powder (Yield=99%).
M.p.=155° C.
[α]$^{24}_D$=−5.9° (c=0.33; CH$_3$OH)

EXAMPLE 72

1-[[2,4-Dichloro-3-[[[4-(1H-imidazol-1-yl)-2-methyl-8-quinolinyl]oxy]methyl]-phenyl]sulphonyl]-N-[2-(dimethylamino)ethyl]-N-methyl-2(S)-pyrrolidine-carboxamide Working analogously to Example 1, starting from N,N,N'-trimethyl-ethylenediamine, the expected product is obtained in the form of a white solid (Yield=33%).
M.p.=98° C.
[α]$^{24}_D$=−20.2° (c=0.36; CH$_3$OH)

EXAMPLE 73

1-[[2,4-Dichloro-3-[[[4-(1H-imidazol-1-yl)-2-methyl-8-quinolinyl]oxy]methyl]-phenyl]sulphonyl]-N-[2-(dimethylamino)ethyl]-N-methyl-2(S)-pyrrolidine-carboxamide, tartrate Working analogously to Example 1, starting from the compound obtained according to Example 72, the expected product is obtained in the form of an ecru white fluffy solid (Yield=93%).
M.p.=125° C.
[α]$^{24}_D$=−30° (c=0.43; CH$_3$OH)

EXAMPLE 74

1-[[2,4-Dichloro-3-[[[4-(1H-imidazol-1-yl)-2-methyl-8-quinolinyl]oxy]methyl]-phenyl]sulphonyl]-N-[2-(1-pyrrolidinyl)ethyl]-2(S)-pyrrolidinecarboxamide Working analogously to Example 1, starting from 1-(2-aminoethyl)-pyrrolidine, the expected product is obtained in the form of a white solid (Yield=62%).
M.p.=105° C.
[α]$^{24}_D$=−50° (c=0.35; CH$_3$OH)

EXAMPLE 75

1-[[2,4-Dichloro-3-[[[4-(1H-imidazol-1-yl)-2-methyl-8-quinolinyl]oxy]methyl]-phenyl]sulphonyl]-N-[2-(1-pyrrolidinyl)ethyl]-2(S)-pyrrolidinecarboxamide, tartrate Working analogously to Example 2, starting from the compound obtained according to Example 74, the expected product is obtained in the form of a yellow fine solid (Yield=97%).
M.p.=129° C.
[α]$^{24}_D$=−30° (c=0.45; CH$_3$OH)

EXAMPLE 76

1-[[2,4-Dichloro-3-[[[4-(1H-imidazol-1-yl)-2-methyl-8-quinolinyl]oxy]methyl]-phenyl]sulphonyl]-N-[3-(1-pyrrolidinyl)propyl]-2(S)-pyrrolidinecarboxamide Working analogously to Example 1, starting from 1-(3-aminopropyl)-pyrrolidine, the expected product is obtained in the form of an ecru white solid (Yield=51%).
M.p.=120° C.
[α]$^{24}_D$=−51° (c=0.35; CH$_3$OH)

EXAMPLE 77

1-[[2,4-Dichloro-3-[[[4-(1H-imidazol-1-yl)-2-methyl-8-quinolinyl]oxy]methyl]-phenyl]sulphonyl]-N-[3-(1-pyrrolidinyl)propyl]-2(S)-pyrrolidinecarboxamide, tartrate Working analogously to Example 2, starting from the compound obtained according to Example 76, the expected product is obtained in the form of a yellow fine solid (Yield=95%).
M.p.=128° C.

$[\alpha]^{24}_D$=−32° (c=0.35; CH$_3$OH)

EXAMPLE 78

1-[[2,4-Dichloro-3-[[[4-(1H-imidazol-1-yl)-2-methyl-8-quinolinyl]oxy]methyl]-phenyl]sulphonyl]-N-[2-(1-piperidinyl)ethyl]-2(S)-pyrrolidinecarboxamide Working analogously to Example 1, starting from 1-(2-aminoethyl)-piperidine, the expected product is obtained in the form of a white solid (Yield=63%).

M.p.=108° C.

$[\alpha]^{22}_D$=−35.1° (c=0.37; CH$_3$OH)

EXAMPLE 79

1-[[2,4-Dichloro-3-[[[4-(1H-imidazol-1-yl)-2-methyl-8-quinolinyl]oxy]methyl]-phenyl]sulphonyl]-N-[2-(1-piperidinyl)ethyl]-2(S)-pyrrolidinecarboxamide, tartrate Working analogously to Example 2, starting from the compound obtained according to Example 78, the expected product is obtained in the form of a yellowish solid (Yield=98%).

M.p.=125° C.

$[\alpha]^{20}_D$=−43.7° (c=0.42; CH$_3$OH)

EXAMPLE 80

N-Cyclopentyl-1-[[2,4-dichloro-3-[[[4-(1H-imidazol-1-yl)-2-methyl-8-quinolinyl]oxy]methyl]phenyl]sulphonyl]pyrrolidinecarboxamide Working analogously to Example 1, starting from cyclopentylamine, the expected product is obtained in the form of a white solid (Yield=86%).

M.p.=75° C.

$[\alpha]^{25}_D$=−17.5° (c=1.05; CH$_3$OH)

EXAMPLE 81

N-Cyclopentyl-1-[[2,4-dichloro-3-[[[4-(1H-imidazol-1-yl)-2-methyl-8-quinolinyl]oxy]methyl]phenyl]sulphonyl]pyrrolidinecarboxamide, methanesulphonate Working analogously to Example 6, starting from the compound obtained according to Example 80, the expected product is obtained in the form of an off-white solid (Yield=91%).

M.p.=134° C.

$[\alpha]^{25}_D$=+3.8° (c=0.83; DMSO)

Preparation XXXV

1-[[2,4-Dichloro-3-[[[2-methyl-4-(1H-1,2,4-triazol-1-yl)-8-quinolinyl]oxy]-methyl]phenyl]sulphonyl]-L-proline, methyl ester Working analogously to Preparation I, starting from 8-hydroxy-2-methyl-4-(1H-1,2,4-triazol-1-yl)-quinoline, the expected product is obtained in the form of a pale yellow solid (Yield=98%).

M.p.=130° C.

$[\alpha]^{22}_D$=−35° (c=0.68; CHCl$_3$)

Preparation XXXVI

1-[[2,4-Dichloro-3-[[[2-methyl-4-(1H-1,2,4-triazol-1-yl)-8-quinolinyl]oxy]-methyl]phenyl]sulphonyl]-L-proline Working analogously to Preparation II, starting from the compound obtained according to Preparation XXXV, the expected product is obtained in the form of a pale yellow powder (Yield=75%).

M.p.=146° C.

$[\alpha]^{24}_D$=−5° (c=0.65; CH$_3$OH)

EXAMPLE 82

1-[[2,4-Dichloro-3-[[[2-methyl-4-(1H-1,2,4-triazol-1-yl)-8-quinolinyl]oxy]-methyl]phenyl]sulphonyl]-N-[2-(dimethylamino)ethyl]-2(S)-pyrrolidine-carboxamide Working analogously to Example 1, starting from the compound obtained according to Preparation XXXVI and N,N-dimethylethylenediamine, the expected product is obtained in the form of white crystals (Yield=60%).

M.p.=106° C.

$[\alpha]^{25}_D$=−35.2° (c=0.45; CH$_3$OH)

EXAMPLE 83

1-[[2,4-Dichloro-3-[[[2-methyl-4-(1H-1,2,4-triazol-1-yl)-8-quinolinyl]oxy]-methyl]phenyl]sulphonyl]-N-[2-(dimethylamino)ethyl]-2(S)-pyrrolidine-carboxamide, tartrate Working analogously to Example 2, starting from the compound obtained according to Example 82, the expected product is obtained in the form of white crystals (Yield=97%).

M.p.=128° C.

$[\alpha]^{25}_D$=−38.1° (c=1; CH$_3$OH)

EXAMPLE 84

1-[[2,4-Dichloro-3-[[[2-methyl-4-(1H-1,2,4-triazol-1-yl)-8-quinolinyl]oxy]-methyl]phenyl]sulphonyl]-N-[3-(dimethylamino)propyl]-2(S)-pyrrolidine-carboxamide Working analogously to Example 82, starting from N,N-dimethyl-1,3-propylenediamine, the expected product is obtained in the form of a white solid (Yield=74%).

M.p.=105° C.

$[\alpha]^{25}_D$=−51° (c=0.75; CHCl$_3$)

EXAMPLE 85

1-[[2,4-Dichloro-3-[[[2-methyl-4-(1H-1,2,4-triazol-1-yl)-8-quinolinyl]oxy]-methyl]phenyl]sulphonyl]-N-[3-(dimethylamino)propyl]-2(S)-pyrrolidine-carboxamide, tartrate Working analogously to Example 2, starting from the compound obtained according to Example 84, the expected product is obtained in the form of white crystals (Yield=99%).

M.p.=124° C.

$[\alpha]^{25}_D$=−42.4° (c=1; CH$_3$OH)

EXAMPLE 86

1-[[2,4-Dichloro-3-[[[2-methyl-4-(1H-1,2,4-triazol-1-yl)-8-quinolinyl]oxy]-methyl]phenyl]sulphonyl]-N-[3-(1-pyrrolidinyl)propyl]-2(S)-pyrrolidine-carboxamide Working analogously to Example 82, starting from 1-(3-aminopropyl)-pyrrolidine, the expected product is obtained in the form of white crystals (Yield=65%).

M.p.=86° C.
[α]$^{25}_D$=−37.8° (c=0.67; CH$_3$OH)

EXAMPLE 87

1-[[2,4-Dichloro-3-[[[2-methyl-4-(1H-1,2,4-triazol-1-yl)-8-quinolinyl]oxy]-methyl]phenyl]sulphonyl]-N-[3-(1-pyrrolidinyl)propyl]-2(S)-pyrrolidine-carboxamide, methanesulphonate Working analogously to Example 6, starting from the compound obtained according to Example 86, the expected product is obtained in the form of a white fine solid (Yield=99%).
M.p.=110° C.
[α]$^{25}_D$=−54.6° (c=0.63; CH$_3$OH)

EXAMPLE 88

1-[[2,4-Dichloro-3-[[[4-(1H-imidazol-1-yl)-2-methyl-8-quinolinyl]oxy]methyl]-phenyl]sulphonyl]-N-[(2-pyridyl)methyl]-2(S)-pyrrolidinecarboxamide Working analogously to Example 1, starting from 2-(aminomethyl)-pyridine, the expected product is obtained in the form of a white solid (Yield=72%).
M.p.=102° C.
[α]$^{25}_D$=−37.5° (c=0.61; CH$_3$OH)

EXAMPLE 89

1-[[2,4-Dichloro-3-[[[4-(1H-imidazol-1-yl)-2-methyl-8-quinolinyl]oxy]methyl]-phenyl]sulphonyl]-N-[(2-pyridinyl)methyl]-2(S)-pyrrolidinecarboxamide, methanesulphonate Working analogously to Example 6, starting from the compound obtained according to Example 88, the expected product is obtained in the form of off-white flakes (Yield=95%).
M.p.=130° C.
[α]$^{25}_D$=−32.6° (c=0.54; CH$_3$OH)

EXAMPLE 90

1-[[2,4-Dichloro-3-[[[4-(1H-imidazol-1-yl)-2-methyl-8-quinolinyl]oxy]methyl]-phenyl]sulphonyl]-N-[(3-pyridinyl)methyl]-2(S)-pyrrolidinecarboxamide Working analogously to Example 1, starting from 3-(aminomethyl)-pyridine, the expected product is obtained in the form of a white solid (Yield=84%).
M.p.=104° C.
[α]$^{25}_D$=−41.9° (c=0.59; CH$_3$OH)

EXAMPLE 91

1-[[2,4-Dichloro-3-[[[4-(1H-imidazol-1-yl)-2-methyl-8-quinolinyl]oxy]methyl]-phenyl]sulphonyl]-N-[(3-pyridinyl)methyl]-2(S)-pyrrolidinecarboxamide, methanesulphonate Working analogously to Example 6, starting from the compound obtained according to Example 90, the expected product is obtained in the form of white crystals (Yield=99%).
M.p.=126° C.
[α]$^{25}_D$=−35.5° (c=0.56; CH$_3$OH)

EXAMPLE 92

1-[[2,4-Dichloro-3-[[[4-(1H-imidazol-1-yl)-2-methyl-8-quinolinyl]oxy]methyl]phenyl]sulphonyl]-N-[(4-pyridinyl)methyl]-2(S)-pyrrolidinecarboxamide Working analogously to Example 1, starting from 4-(aminomethyl)-pyridine, the expected product is obtained in the form of a white solid (Yield=90%).
M.p.=114° C.
[α]$^{25}_D$=−50.3° (c=0.51; CH$_3$OH)

EXAMPLE 93

1-[[2,4-Dichloro-3-[[[4-(1H-imidazol-1-yl)-2-methyl-8-quinolinyl]oxy]methyl]-phenyl]sulphonyl]-N-[(4-pyridinyl)methyl]-2(S)-pyrrolidinecarboxamide, tartrate Working analogously to Example 2, starting from the compound obtained according to Example 92, the expected product is obtained in the form of a yellow solid (Yield=98%).
M.p.=128° C.
[α]$^{25}_D$=−34.5° (c=0.49; CH$_3$OH)

EXAMPLE 94

8-[[2,6-Dichloro-3-[[2(S)-[[4-(4-pyridinyl)-1-piperazinyl]carbonyl]-1-pyrrolidinyl]sulphonyl]phenyl]methoxy]-4-(1H-imidazol-1-yl)-2-methyl-quinoline Working analogously to Example 1, starting from 1-(4-pyridinyl)-piperazine, the expected product is obtained in the form of a white solid (Yield=45%).
M.p.=136° C.
[α]$^{25}_D$=−32.3° (c=0.46; CH$_3$OH)

EXAMPLE 95

8-[[2,6-Dichloro-3-[[2(S)-[[4-(4-pyridinyl)-1-piperazinyl]carbonyl]-1-pyrrolidinyl]sulphonyl]phenyl]methoxy]-4-(1H-imidazol-1-yl)-2-methyl-quinoline, tartrate Working analogously to Example 2, starting from the compound obtained according to Example 94, the expected product is obtained in the form of pale yellow flakes (Yield=89%).
M.p.=146° C.
[α]$^{25}_D$=−23.2° (c=0.52; CH$_3$OH)

EXAMPLE 96

8-[[2,6-Dichloro-3-[[2(S)-[[4-(2-pyridinyl)-1-piperazinyl]carbonyl]-1-pyrrolidinyl]sulphonyl]phenyl]methoxy]-4-(1H-imidazol-1-yl)-2-methyl-quinoline Working analogously to Example 1, starting from 1-(2-pyridinyl)-piperazine, the expected product is obtained in the form of a white solid (Yield=34%).
M.p.=108° C.
[α]$^{25}_D$=−27.6° (c=0.4; CH$_3$OH)

EXAMPLE 97

8-[[2,6-Dichloro-3-[[2(S)-[[4-(2-pyridinyl)-1-piperazinyl]carbonyl]-1-pyrrolidinyl]sulphonyl]phenyl]methoxy]-4-(1H-imidazol-1-yl)-2-methyl-quinoline, methanesulphonate Working analogously to Example 6, starting from the compound obtained according to Example 96, the expected product is obtained in the form of a white solid (Yield=99%).

M.p.=138° C.

$[\alpha]^{25}_D$=−17.3° (c=0.37; $CH_3OH$)

Preparation XXXVII

2-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl](methyl)amino]ethyl]-(methyl)carbamic acid, 1,1-dimethylethyl ester Working analogously to Example 1, starting from the t-butyl ester of [2-(methylamino)ethyl](methyl)carbamic acid, the expected product is obtained in the form of white crystals (Yield=93%).

M.p.=75° C.

$[\alpha]^{25}_D$=−21.4° (c=0.67; $CH_3OH$)

EXAMPLE 98

1-[[2,4-Dichloro-3-[[[4-(1H-imidazol-1-yl)-2-methyl-8-quinolinyl]oxy]methyl]-phenyl]sulphonyl]-N-methyl-N-[2-(methylamino)ethyl]-2(S)-pyrrolidine-carboxamide Working analogously to Example 9, starting from the compound obtained according to Preparation XXXVII, the expected product is obtained in the form of yellow crystals (Yield=97%).

M.p.=116° C.

$[\alpha]^{25}_D$=−22.6° (c=0.6; $CH_3OH$)

Preparation XXXVIII

[3-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl](methyl)amino]propyl]-(methyl)carbamic acid, 1,1-dimethylethyl ester Working analogously to Example 1, starting from the t-butyl ester of [3-(methylamino)propyl](methyl)carbamic acid, the expected product is obtained in the form of pale yellow crystals (Yield=86%).

M.p.=70° C.

$[\alpha]^{25}_D$=−16.4° (c=0.6; $CH_3OH$)

EXAMPLE 99

1-[[2,4-Dichloro-3-[[[4-(1H-imidazol-1-yl)-2-methyl-8-quinolinyl]oxy]methyl]-phenyl]sulphonyl]-N-methyl-N-[3-(methylamino)propyl]-2(S)-pyrrolidine-carboxamide Working analogously to Example 9, starting from the compound obtained according to Preparation XXXVIII, the expected product is obtained in the form of yellow crystals (Yield=99%).

M.p.=125° C.

$[\alpha]^{25}_D$=−34.5° (c=0.54; $CH_3OH$)

Preparation XXXIX

1-[[2,4-Dichloro-3-[[[4-(1H-imidazol-1-yl)-2-methyl-8-quinolinyl]oxy]methyl]-phenyl]sulphonyl]-N-methyl-N-[2-[[3-(acetoxy)propyl](methyl)amino]ethyl]-2(S)-pyrrolidinecarboxamide Working analogously to Preparation XIII, starting from the compound obtained according to Example 98 and 3-iodopropyl acetate, the expected product is obtained in the form of white crystals (Yield=44%).

M.p.=75° C.

$[\alpha]^{25}_D$=−16.1° (c=0.6; $CH_3OH$)

Preparation XL

1-[[2,4-Dichloro-3-[[[4-(1H-imidazol-1-yl)-2-methyl-8-quinolinyl]oxy]methyl]-phenyl]sulphonyl]-N-methyl-N-[2-[[4-(acetoxy)butyl](methyl)amino]ethyl]-2(S)-pyrrolidinecarboxamide Working analogously to Preparation XXXIX, starting from 4-bromo-butyl acetate, the expected product is obtained in the form of white crystals (Yield=55%).

M.p.=76° C.

$[\alpha]^{25}_D$=−14.2° (c=0.53; $CH_3OH$)

Preparation XLI

1-[[2,4-Dichloro-3-[[[4-(1H-imidazol-1-yl)-2-methyl-8-quinolinyl]oxy]methyl]-phenyl]sulphonyl]-N-methyl-N-[3-[[3-(acetoxy)propyl](methyl)amino]propyl]-2(S)-pyrrolidinecarboxamide Working analogously to Preparation XXXIX, starting from the compound obtained according to Example 99, the expected product is obtained in the form of beige crystals (Yield=73%).

M.p.=90° C.

$[\alpha]^{25}_D$=−28.3° (c=0.68; $CH_3OH$)

Preparation XLII

1-[[2,4-Dichloro-3-[[[4-(1H-imidazol-1-yl)-2-methyl-8-quinolinyl]oxy]methyl]-phenyl]sulphonyl]-N-methyl-N-[3-[[4-(acetoxy)butyl](methyl)amino]propyl]-2(S)-pyrrolidinecarboxamide Working analogously to Preparation XL, starting from the compound obtained according to Example 99, the expected product is obtained in the form of pale yellow crystals (Yield=69%).

M.p.=88° C.

$[\alpha]^{25}_D$=−29.1° (c=0.7; $CH_3OH$)

EXAMPLE 100

1-[[2,4-Dichloro-3-[[[4-(1H-imidazol-1-yl)-2-methyl-8-quinolinyl]oxy]methyl]-phenyl]sulphonyl]-N-methyl-N-[2-[[3-(hydroxy)propyl](methyl)amino]ethyl]-2(S)-pyrrolidinecarboxamide Working analogously to Example 11, starting from the compound obtained according to Preparation XXXIX, the expected product is obtained in the form of white crystals (Yield=92%).

M.p.=98° C.

$[\alpha]^{25}_D$=−15.9° (c=0.6; $CH_3OH$)

EXAMPLE 101

1-[[2,4-Dichloro-3-[[[4-(1H-imidazol-1-yl)-2-methyl-8-quinolinyl]oxy]methyl]-phenyl]sulphonyl]-N-methyl-N-[2-[[3-(hydroxy)propyl](methyl)amino]ethyl]-2(S)-pyrrolidinecarboxamide, methanesulphonate Working analogously to Example 4, starting from the compound obtained according to Example 100, the expected product is obtained in the form of white flakes (Yield=99%).

M.p.=118° C.

$[\alpha]^{25}_D$=−37.1° (c=0.6; CH$_3$OH)

EXAMPLE 102

1-[[2,4-Dichloro-3-[[[4-(1H-imidazol-1-yl)-2-methyl-8-quinolinyl]oxy]methyl]-phenyl]sulphonyl]-N-methyl-N-[2-[[4-(hydroxy)butyl](methyl)amino]ethyl]-2(S)-pyrrolidinecarboxamide Working analogously to Example 11, starting from the compound obtained according to Preparation XL, the expected product is obtained in the form of white crystals (Yield=74%).

M.p.=84° C.

$[\alpha]^{25}_D$=−18.1° (c=0.62; CH$_3$OH)

EXAMPLE 103

1-[[2,4-Dichloro-3-[[[4-(1H-imidazol-1-yl)-2-methyl-8-quinolinyl]oxy]methyl]-phenyl]sulphonyl]-N-methyl-N-[2-[[4-(hydroxy)butyl](methyl)amino]ethyl]-2(S)-pyrrolidinecarboxamide, methanesulphonate Working analogously to Example 6, starting from the compound obtained according to Example 102, the expected product is obtained in the form of white flakes (Yield=99%).

M.p.=120° C.

$[\alpha]^{25}_D$=−43.2° (c=0.65; CH$_3$OH)

EXAMPLE 104

1-[[2,4-Dichloro-3-[[[4-(1H-imidazol-1-yl)-2-methyl-8-quinolinyl]oxy]methyl]-phenyl]sulphonyl]-N-methyl-N-[3-[[3-(hydroxy)propyl](methyl)amino]-propyl]-2(S)-pyrrolidinecarboxamide Working analogously to Example 11, starting from the compound obtained according to Preparation XLI, the expected product is obtained in the form of white crystals (Yield=84%).

M.p.=92° C.

$[\alpha]^{25}_D$=−18.1° (c=0.56; CH$_3$OH)

EXAMPLE 105

1-[[2,4-Dichloro-3-[[2(L)-[[4-(2-pyridinyl)-1-piperazinyl]carbonyl]-1-pyrrolidinyl]sulphonyl]-N-methyl-N-[3-[[3-(hydroxy)propyl]-(methyl)amino]propyl]-2(S)-pyrrolidinecarboxamide, methanesulphonate Working analogously to Example 6, starting from the compound obtained according to Example 104, the expected product is obtained in the form of white flakes (Yield=99%).

M.p.=116° C.

$[\alpha]^{25}_D$=−49.1° (c=0.69; CH$_3$OH)

EXAMPLE 106

1-[[2,4-Dichloro-3-[[[4-(1H-imidazol-1-yl)-2-methyl-8-quinolinyl]oxy]methyl]-phenyl]sulphonyl]-N-methyl-N-[3-[[4-(hydroxy)butyl](methyl)amino]propyl]-2(S)-pyrrolidinecarboxamide Working analogously to Example 11, starting from the compound obtained according to Preparation XLII, the expected product is obtained in the form of white crystals (Yield=77%).

M.p.=82° C.

$[\alpha]^{25}_D$=−22.1° (c=0.62; CH$_3$OH)

EXAMPLE 107

1-[[2,4-Dichloro-3-[[[4-(1H-imidazol-1-yl)-2-methyl-8-quinolinyl]oxy]methyl]-phenyl]sulphonyl]-N-methyl-N-[3-[[4-(hydroxy)butyl](methyl)amino]propyl]-2(S)-pyrrolidinecarboxamide, methanesulphonate Working analogously to Example 6, starting from the compound obtained according to Example 106, the expected product is obtained in the form of white flakes (Yield=98%).

M.p.=100° C.

$[\alpha]^{25}_D$=−49.5° (c=0.58; CH$_3$OH)

EXAMPLE 108

1-[[2,4-Dichloro-3-[[[4-(1H-imidazol-1-yl)-2-methyl-8-quinolinyl]oxy]methyl]-phenyl]sulphonyl]-N-[[1-(2-pyridinylmethyl)-4-piperidinyl]methyl]-2(S)-pyrrolidinecarboxamide Working analogously to Preparation XIII, starting from 2-(chloromethyl)pyridine hydrochloride, the expected product is obtained in the form of a white solid (Yield=31%).

M.p.=100° C.

$[\alpha]^{25}_D$=−43.2° (c=0.4; CH$_3$OH)

EXAMPLE 109

1-[[2,4-Dichloro-3-[[[4-(1H-imidazol-1-yl)-2-methyl-8-quinolinyl]oxy]methyl]-phenyl]sulphonyl]-N-[[1-(2-pyridinylmethyl)-4-piperidinyl]methyl]-2(S)-pyrrolidinecarboxamide, methanesulphonate Working analogously to Example 6, starting from the compound obtained according to Example 108, the expected product is obtained in the form of a white solid (Yield=90%).

M.p.=130° C.

$[\alpha]^{25}_D$=−44.8° (c=0.3; CH$_3$OH)

EXAMPLE 110

1-[[2,4-Dichloro-3-[[[4-(1H-imidazol-1-yl)-2-methyl-8-quinolinyl]oxy]methyl]-phenyl]sulphonyl]-N-[[1-(3-pyridinylmethyl)-4-piperidinyl]methyl]-2(S)-pyrrolidinecarboxamide Working analogously to Preparation XIII, starting from 3-(chloromethyl)pyridine hydrochloride, the expected product is obtained in the form of a white powder (Yield=80%).

M.p.=107° C.

$[\alpha]^{25}_D$=−30.7° (c=0.35; CH$_3$OH)

EXAMPLE 111

1-[[2,4-Dichloro-3-[[[4-(1H-imidazol-1-yl)-2-methyl-8-quinolinyl]oxy]methyl]-phenyl]sulphonyl]-N-[[1-(3-pyridinylmethyl)-4-piperidinyl]methyl]-2(S)-pyrrolidinecarboxamide, methanesulphonate Working analogously to Example 6, starting from the compound obtained according to Example 110, the expected product is obtained in the form of white flakes (Yield=99%).

M.p.=141° C.
$[\alpha]^{25}_D$=−44.4° (c=0.36; CH$_3$OH)

EXAMPLE 112

1-[[2,4-Dichloro-3-[[[4-(1H-imidazol-1-yl)-2-methyl-8-quinolinyl]oxy]methyl]-phenyl]sulphonyl]-N-[[1-(4-pyridinylmethyl)-4-piperidinyl]methyl]-2(S)-pyrrolidinecarboxamide Working analogously to Preparation XIII, starting from 4-(chloromethyl)pyridine hydrochloride, the expected product is obtained in the form of a yellow solid (Yield=83%).

M.p.=113° C.
$[\alpha]^{25}_D$=−27.7° (c=0.39; CH$_3$OH)

EXAMPLE 113

1-[[2,4-Dichloro-3-[[[4-(1H-imidazol-1-yl)-2-methyl-8-quinolinyl]oxy]methyl]-phenyl]sulphonyl]-N-[[1-(4-pyridinylmethyl)-4-piperidinyl]methyl]-2(S)-pyrrolidinecarboxamide, methanesulphonate Working analogously to Example 6, starting from the compound obtained according to Example 112, the expected product is obtained in the form of a white solid (Yield=92%).

M.p.=96° C.
$[\alpha]^{25}_D$=−39.8° (c=0.34; CH$_3$OH)

Preparation XLIII

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl-]-1-piperidinepropanoic acid, 1,1-dimethylethyl ester A suspension of 0.7 g (1.06×10$^{-3}$ mol) of the compound obtained according to Example 9 is prepared in 20 ml de tetrahydrofuran. 0.66 g (5.1×10$^{-3}$ mol) of t-butyl acrylate is added at 50° C. and the mixture is kept at 50° C. with stirring for 100 hours. The solvent is driven off under reduced pressure and the residue is purified by chromatography on silica gel eluting with the aid of a dichloromethane/methanol/ammonia (97/3/0.1; v/v/v) mixture. 0.5 g of the expected product is thus obtained in the form of a white solid (Yield=61%).

M.p.=92° C.
$[\alpha]^{23}_D$=−41° (c=0.31; CH$_3$OH)

EXAMPLE 114

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidinepropanoic acid A solution of 0.48 g (0.61×10$^{-3}$ mol) of the compound obtained according to Preparation XLIII is prepared in 30 ml of dichloromethane and, at 0° C., 66 mg (0.61×10$^{-3}$ mol) of anisole are added and, dropwise, 10 ml of trifluoroacetic acid. The reaction mixture is then kept with stirring at ambient temperature for 20 hours, and then concentrated under reduced pressure. The residue is triturated in 10 ml of diethyl ether and the solid product obtained is separated by filtration and then purified by chromatography on silica gel eluting with the aid of a dichloromethane/methanol/ammonia (80/20/2; v/v/v) mixture. 0.2 g of the expected product is thus obtained in the form of a white solid (Yield=45%).

M.p.=140° C.
$[\alpha]^{22}_D$=−52° (c=0.35; CH$_3$OH)

EXAMPLE 115

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidinepropanoic acid, tartrate Working analogously to Example 2, starting from the compound obtained according to Example 114, the expected product is obtained in the form of a white solid (Yield=86%).

M.p.=138° C.
$[\alpha]^{23}_D$=−32° (c=0.39; CH$_3$OH)

Preparation XLIV

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidinebutanoic acid, methyl ester Working analogously to Preparation XIII, starting from the compound obtained according to Example 9 and methyl 4-bromobutanoate, the expected product is obtained in the form of an ecru white solid (Yield=58%).

M.p.=98° C.
$[\alpha]^{22}_D$=−40° (c=0.43; CH$_3$OH)

EXAMPLE 116

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidinebutanoic acid A solution of 0.49 g (0.65×10$^{-3}$ mol) of the ester obtained according to Preparation XLIV is prepared in 10 ml of dioxane and 1.3 ml of a solution of N sodium hydroxide are added. The reaction mixture is heated at reflux for 10 hours and then concentrated under reduced pressure. The residue is taken up again in water and acidified to pH 4.5 with the aid of a dilute hydrochloric acid solution. The water is removed by lyophilization and the solid obtained is purified by chromatography on RP18-grafted silica gel eluting with the aid of an acetonitrile/water (2/1; v/v) mixture. 0.24 g of the expected product is thus obtained in the form of a white solid (Yield=50%).

M.p.=178° C.
$[\alpha]^{20}_D$=−16° (c=0.5; CH$_3$OH)

EXAMPLE 117

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-1-piperidinebutanoic acid, tartrate Working analogously to Example 2, starting from the compound obtained according to Example 116, the expected product is obtained in the form of a white solid (Yield=87%).

M.p.=158° C.
$[\alpha]^{24}_D$=−7° (c=0.34; CH$_3$OH)

Preparation XLV

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-β-oxo-1-piperidinepropanoic acid, 1,1-dimethylethyl ester Working analogously to Example 1, starting from the compound obtained according to Example 9 and mono-t- butyl malonate, the expected product is obtained in the form of a white solid (Yield=59%).

M.p.=101° C.

$[\alpha]^{29}_D$=−34° (c=0.33; $CH_3OH$)

EXAMPLE 118

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonylamino]methyl]-β-oxo-1-piperidinepropanoic acid, trifluororacetate Working analogously to Example 114, starting from the compound obtained according to Preparation XLV, the expected product is obtained in the form of a yellow solid (Yield=87%).

M.p.=130° C.

$[\alpha]^{22}_D$=−22° (c=0.56; $CH_3OH$)

EXAMPLE 119

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-β-oxo-1-piperidinebutanoic acid A suspension of 0.5 g (0.76×10⁻³ mol) of the compound obtained according to Example 9 is prepared in 15 ml of acetone and 76 mg (0.76×10⁻³ mol) of succinic anhydride are added. The reaction mixture is heated at reflux for 8 hours and the solvent is eliminated under reduced pressure. The residue is purified by chromatography on silica gel eluting with the aid of a dichloromethane/methanol/ammonia (90/10/1; v/v/v) mixture. 0.26 g of the expected product is thus obtained in the form of a white solid (Yield=45%).

M.p.=125° C.

$[\alpha]^{22}_D$=−33° (c=0.38; $CH_3OH$)

EXAMPLE 120

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-β-oxo-1-piperidinebutanoic acid, tartrate Working analogously to Example 2, starting from the compound obtained according to Example 119, the expected product is obtained in the form of a yellow solid (Yield=75%).

M.p.=130° C.

$[\alpha]^{19}_D$=−22° (c=0.50; $CH_3OH$)

Preparation XLVI

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-δ-oxo-1-piperidinepentanoic acid, 1,1-dimethylethyl ester Working analogously to Example 1, starting from the compound obtained according to Example 9 and mono t-butyl glutarate, the expected product is obtained in the form of a white solid (Yield=44%).

M.p.=112° C.

$[\alpha]^{22}_D$=−41° (c=0.30; $CH_3OH$)

EXAMPLE 121

4-[[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]methyl]-δ-oxo-1-piperidinepentanoic acid, trifluoroacetate Working analogously to Example 13, starting from the compound obtained according to Preparation XLVI, the expected product is obtained in the form of a yellow fine solid (Yield=77%).

M.p.=131° C.

$[\alpha]^{23}_D$=−15° (c=0.37; $CH_3OH$)

Preparation XLVII

N-[2-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl](methyl)amino]ethyl]-N-methylglycine, 1,1-dimethylethyl ester Working analogously to Preparation XVI, starting from the compound obtained according to Example 98, the expected product is obtained in the form of a white solid (Yield=67%).

M.p.=71° C.

$[\alpha]^{25}_D$=−20° (c=0.37; $CH_3OH$)

EXAMPLE 122

N-[2-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl](methyl)amino]ethyl]-N-methylglycine, trifluoroacetate Working analogously to Example 13, starting from the compound obtained according to Preparation XLVII, the expected product is obtained in the form of a yellow solid (Yield=84%).

M.p.=120° C.

$[\alpha]^{22}_D$=−29° (c=0.49; $CH_3OH$)

Preparation XLVIII

[3-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]propyl](methyl)-carbamic acid, 1,1-dimethylethyl ester Working analogously to Example 1, starting from t-butyl (3-aminopropyl)(methyl)carbamate, the expected product is obtained in the form of a white solid (Yield=69%).

M.p.=75° C.

$[\alpha]^{25}_D$=−26.5° (c=0.35; $CH_3OH$)

EXAMPLE 123

1-[[2,4-Dichloro-3-[[[4-(1H-imidazol-1-yl)-2-methyl-8-quinolinyl]oxy]methyl]-phenyl]sulphonyl]-N-[3-(methylamino)propyl]-2(S)-pyrrolidinecarboxamide, trifluoroacetate Working analogously to Example 13, starting from the compound obtained according to Preparation XLVIII, the expected product is obtained in the form of a yellow solid (Yield=99%).

M.p.=120° C.

$[\alpha]^{24}_D$=−49° (c=0.48; $CH_3OH$)

Preparation IL

N-[3-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl](methyl)amino]propyl]-N-methylglycine, 1,1-dimethylethyl ester Working analogously to Preparation XVI, starting from the compound obtained according to Example 99, the expected product is obtained in the form of a white solid (Yield=73%).

M.p.=72° C.

$[\alpha]^{25}_D$=−12° (c=0.45; CH$_3$OH)

EXAMPLE 124

N-[3-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl](methyl)amino]propyl]-N-methylglycine, bis-trifluoroacetate Working analogously to Example 13, starting from the compound obtained according to Preparation IL, the expected product is obtained in the form of a yellow solid (Yield=92%).

M.p.=110° C.

$[\alpha]^{22}_D$=−34° (c=0.34; CH$_3$OH)

EXAMPLE 125

1-[[2,4-Dichloro-3-[[[2-methyl-4-(1H-1,2,4-triazol-1-yl)-8-quinolinyl]-oxy]methyl]phenyl]sulphonyl]-N-[[1-(2-pyridinylmethyl)-4-piperidinyl]-methyl]-2(S)-pyrrolidinecarboxamide A mixture of 0.5 g (0.563×10$^{-3}$ mol) of the compound obtained according to Example 26 is prepared in 10 ml of acetonitrile. 0.39 g (2.81×10$^{-3}$ mol) of potassium carbonate and then 0.111 g (0.676×10$^{-3}$ mol) of 2-picolyl chloride (in hydrochloride form) are added. The reaction mixture is stirred at 80° C. for 45 min and then cooled and filtered. The inorganic salts are rinsed with dichloromethane which is united with the filtrate. This solution is concentrated under reduced pressure and the residue is purified by chromatography on silica gel eluting with the aid of a dichloromethane/methanol (9/1; v/v) mixture. The expected product is thus obtained in the form of a white powder (Yield=71%).

M.p.=118° C.

$[\alpha]^{28}_D$=−46° (c=0.36; CHCl$_3$)

EXAMPLE 126

1-[[2,4-Dichloro-3-[[[2-methyl-4-(1H-1,2,4-triazol-1-yl)-8-quinolinyl]oxy]-methyl]phenyl]sulphonyl]-N-[[1-(2-pyridinylmethyl)-4-piperidinyl]methyl]-2(S)-pyrrolidinecarboxamide, methanesulphonate Working analogously to Example 6, starting from the compound obtained according to Example 125, the expected product is obtained in the form of a beige solid (Yield=91%).

M.p.=139° C.

$[\alpha]^{28}_D$=−76° (c=0.59; CH$_3$OH)

EXAMPLE 127

1-[[2,4-Dichloro-3-[[[4-(1H-imidazol-1-yl)-2-methyl-8-quinolinyl]oxy]methyl]-phenyl]sulphonyl]-N-[[1-(phenylmethyl)-4-piperidinyl]methyl]-2(S)-pyrrolidinecarboxamide A mixture of 1 g (1.12×10$^{-3}$ mol) of the compound obtained according to Example 9 is prepared in 4 ml of dimethylformamide and 100 ml of dichloromethane. 0.787 ml (5.64×10$^{-3}$ mol) of triethylamine is added, and then, after having cooled the mixture to 0° C., 0.148 ml (1.24×10$^{-3}$ mol) of benzyl bromide. The reaction mixture is kept at ambient temperature for 24 hours with stirring and then concentrated under reduced pressure. The residue is redissolved in ethyl acetate in the presence of water; the mixture is brought to alkaline pH (pH 9–10) with the aid of a solution of sodium hydroxide. The aqueous phase is extracted with ethyl acetate and the combined organic phases are washed with water, dried over magnesium sulphate and then concentrated under reduced pressure. Purification of the crude product by chromatography on silica gel eluting with the aid of a dichloromethane/methanol (95/5; v/v) mixture allows the expected product to be obtained in the form of a white fine solid (Yield=56%).

M.p.=123° C.

$[\alpha]^{28}_D$=−43° (c=0.73; CH$_3$OH)

EXAMPLE 128

1-[[2,4-Dichloro-3-[[[4-(1H-imidazol-1-yl)-2-methyl-8-quinolinyl]oxy]methyl]-phenyl]sulphonyl]-N-[[1-(phenylmethyl)-4-piperidinyl]methyl]-2(S)-pyrrolidinecarboxamide, methanesulphonate Working analogously to Example 6, starting from the compound obtained according to Example 127, the expected product is obtained in the form of a white solid (Yield=95%).

M.p.=161° C.

$[\alpha]^{26}_D$=−44° (c=0.63; CH$_3$OH)

EXAMPLE 129

N-[(1-Benzoyl-4-piperidinyl)methyl]-1-[[2,4-dichloro-3-[[[4-(1H-imidazol-1-yl)-2-methyl-8-quinolinyl]oxy]methyl]phenyl]sulphonyl]-2(S)-pyrrolidine-carboxamide Working analogously to Example 127, starting from benzoyl chloride, the expected product is obtained in the form of a white solid (Yield=67%).

M.p.=102° C.

$[\alpha]^{28}_D$=−48° (c=0.66; CHCl$_3$)

EXAMPLE 130

N-[(1-benzoyl-4-piperidinyl)methyl]-1-[[2,4-dichloro-3-[[[4-(1H-imidazol-1-yl)-2-methyl-8-quinolinyl]oxy]methyl]phenyl]sulphonyl]-2(S)-pyrrolidine-carboxamide, methanesulphonate Working analogously to Example 6, starting from the compound obtained according to Example 129, the expected product is obtained in the form of a pale yellow solid (Yield=95%).

M.p.=153° C.

$[\alpha]^{26}_D$=−24° (c=0.55; CH$_3$OH)

EXAMPLE 131

1-[[2,4-Dichloro-3-[[[4-(1H-imidazol-1-yl)-2-methyl-8-quinolinyl]oxy]methyl]-phenyl]sulphonyl]-N-[[1-(4-pyridinylcarbonyl)-4-piperidinyl]methyl]-2(S)-pyrrolidinecarboxamide Working analogously to Example 127, starting from isonicotinoyl chloride hydrochloride, the expected product is obtained in the form of a white fine solid (Yield=34%).

M.p.=134° C.

$[\alpha]^{28}_D$=−56° (c=0.64; CHCl$_3$)

EXAMPLE 132

1-[[2,4-Dichloro-3-[[[4-(1H-imidazol-1-yl)-2-methyl-8-quinolinyl]oxy]methyl]-phenyl]sulphonyl]-N-[[1-(4-pyridinylcarbonyl)-4-piperidinyl]methyl]-2(S)-pyrrolidinecarboxamide, methanesulphonate Working analogously to Example 6, starting from the compound obtained according to Example 131, the expected product is obtained in the form of a white solid (Yield=90%).

M.p.=165° C.
[α]$^{26}_D$=−29° (c=0.48; CH$_3$OH)

EXAMPLE 133

1-[[2,4-Dichloro-3-[[[4-(1H-imidazol-1-yl)-2-methyl-8-quinolinyl]oxy]methyl]-phenyl]sulphonyl]-N-[[1-(3-pyridinylcarbonyl)-4-piperidinyl]methyl]-2(S)-pyrrolidinecarboxamide Working analogously to Example 127, starting from nicotinoyl chloride, the expected product is obtained in the form of a white fine solid (Yield=79%).
M.p.=109° C.
[α]$^{24}_D$=−45° (c=0.88; CHCl$_3$)

EXAMPLE 134

1-[[2,4-Dichloro-3-[[[4-(1H-imidazol-1-yl)-2-methyl-8-quinolinyl]oxy]methyl]-phenyl]sulphonyl]-N-[[[1-(3-pyridinylcarbonyl)-4-piperidinyl]methyl]-2(S)-pyrrolidinecarboxamide, methanesulphonate Working analogously to Example 6, starting from the compound obtained according to Example 133, the expected product is obtained in the form of a white solid (Yield=82%).
M.p.=150° C.
[α]$^{24}_D$=−38° (c=0.59; CH$_3$OH)

EXAMPLE 135

1-[[2,4-Dichloro-3-[[[4-(1H-imidazol-1-yl)-2-methyl-8-quinolinyl]oxy]methyl]-phenyl]sulphonyl]-N-[[1-(2-pyridinylcarbonyl)-4-piperidinyl]methyl]-2(S)-pyrrolidinecarboxamide Working analogously to Example 1, starting from picolinic acid, the expected product is obtained in the form of a white solid (Yield=52%).
M.p.=103° C.
[α]$^{24}_D$=−58° (c=0.90; CHCl$_3$)

EXAMPLE 136

1-[[2,4-Dichloro-3-[[[4-(1H-imidazol-1-yl)-2-methyl-8-quinolinyl]oxy]methyl]-phenyl]sulphonyl]-N-[[1-(2-pyridinylcarbonyl)-4-piperidinyl]methyl]-2(S)-pyrrolidinecarboxamide, methanesulphonate Working analogously to Example 6, starting from the compound obtained according to Example 135, the expected product is obtained in the form of a pale yellow solid (Yield=89%).
M.p.=152° C.
[α]$^{24}_D$=−25° (c=0.76; CH$_3$OH)

Preparation L

1-[[2,4-Dichloro-3-[[[2-methyl-4-(1H-1,2,4-triazol-1-yl)-2-methyl-8-quinolinyl]oxy]methyl]phenyl]sulphonyl]-L-proline, methyl ester Working analogously to Preparation I, starting from 8-hydroxy-2-methyl-4-(1H-1,2,4-triazol-1-yl)quinoline, the expected product is obtained in the form of a pale yellow solid (Yield=98%).
M.p.=130° C.
[α]$^{22}_D$=−35° (c=0.68; CHCl$_3$)

Preparation LI

1-[[2,4-Dichloro-3-[[[2-methyl-4-(1H-1,2,4-triazol-1-yl)-2-methyl-8-quinolinyl]oxy]methyl]phenyl]sulphonyl]-L-proline Working analogously to Preparation II, starting from the compound obtained according to Preparation L, the expected product is obtained in the form of a pale yellow solid (Yield=72%).
M.p.=146° C.
[α]$^{24}_D$=−5° (c=0.68; CH$_3$OH)

EXAMPLE 137

1-[[2,4-Dichloro-3-[[[2-methyl-4-(1H-1,2,4-triazol-1-yl)-2-methyl-8-quinolinyl]oxy]methyl]phenyl]sulphonyl]-N-[3-(dimethylamino)propyl]-2(S)-pyrrolidinecarboxamide Working analogously to Example 1, starting from the acid obtained according to Preparation LI and N,N-dimethylpropanediamine, the expected product is obtained in the form of a beige amorphous solid (Yield=74%).
M.p.=105° C.
[α]$^{24}_D$=−51° (c=0.75; CHCl$_3$)

EXAMPLE 138

1-[[2,4-Dichloro-3-[[[2-methyl-4-(1H-1,2,4-triazol-1-yl)-2-methyl-8-quinolinyl]oxy]methyl]phenyl]sulphonyl]-N-[3-(dimethylamino)propyl]-2(S)-pyrrolidinecarboxamide, hemisulphate Working analogously to Example 44, starting from the compound obtained according to Example 137, the expected product is obtained in the form of a pale yellow solid (Yield=98%).
M.p.=154° C.
[α]$^{23}_D$=−26° (c=0.77; CH$_3$OH)

EXAMPLE 139

1-[[2,4-Dichloro-3-[[[2-methyl-4-(1H-1,2,4-triazol-1-yl)-2-methyl-8-quinolinyl]oxy]methyl]phenyl]sulphonyl]-N-methyl-2(S)-pyrrolidine-carboxamide Working analogously to Example 137, starting from methylamine hydrochloride, the expected product is obtained in the form of a white solid (Yield=60%).
M.p.=131° C.
[α]$^{28}_D$=−37° (c=0.94; CHCl$_3$)

EXAMPLE 140

1-[[2,4-Dichloro-3-[[[2-methyl-4-(1H-1,2,4-triazol-1-yl)-2-methyl-8-quinolinyl]oxy]methyl]phenyl]sulphonyl]-N-[[(2-pyridinyl)methyl]-2(S)-pyrrolidinecarboxamide Working analogously to Example 137, starting from 2-(aminomethyl)-pyridine, the expected product is obtained in the form of a white fine solid (Yield=85%).
M.p.=95° C.
[α]$^{28}_D$=−31° (c=0.53; CHCl$_3$)

EXAMPLE 141

1-[[2,4-Dichloro-3-[[[2-methyl-4-(1H-1,2,4-triazol-1-yl)-2-methyl-8-quinolinyl]oxy]methyl]phenyl]sulphonyl]-N-[(2-pyridinyl)methyl]-2(S)-pyrrolidinecarboxamide, methanesulphonate Working analogously to Example 4, starting from the compound obtained according to Example 140, the expected product is obtained in the form of a pale yellow solid (Yield=85%).

M.p.=108° C.
$[\alpha]^{28}_D$=−33° (c=0.52; $CH_3OH$)

EXAMPLE 142

8-[[2,6-Dichloro-3-[[2(S)-[[4-(2-pyridinyl)-1-piperazinyl]carbonyl]-1-pyrrolidinyl]sulphonyl]phenyl]methoxy]-2-methyl-4-(1H-1,2,4-triazol-1-yl)quinoline Working analogously to Example 137, starting from 1-(2-pyridyl)-piperazine, the expected product is obtained in the form of a white powder (Yield=75%).

M.p.=108° C.
$[\alpha]^{26}_D$=+9° (c=0.47; $CHCl_3$)

EXAMPLE 143

8-[[2,6-Dichloro-3-[[2(S)-[[4-(2-pyridinyl)-1-piperazinyl]carbonyl]-1-pyrrolidinyl]sulphonyl]phenyl]methoxy]-2-methyl-4-(1H-1,2,4-triazol-1-yl)-quinoline, methanesulphonate Working analogously to Example 6, starting from the compound obtained according to Example 142, the expected product is obtained in the form of a yellow solid (Yield=88%).

M.p.=160° C.
$[\alpha]^{26}_D$=−12° (c=0.65; $CH_3OH$)

EXAMPLE 144

8-[[2,6-Dichloro-3-[[2(S)-(4-morpholinylcarbonyl)-1-pyrrolidinyl]sulphonyl]-phenyl]methoxy]-4-(1H-imidazol-1-yl)-2-methylquinoline Working analogously to Example 1, starting from morpholine, the 25 expected product is obtained in the form of a white solid (Yield=76%).

M.p.=50° C.
$[\alpha]^{27}_D$=+15° (c=0.54; $CHCl_3$)

EXAMPLE 145

8-[[2,6-Dichloro-3-[[2(S)-(4-morpholinylcarbonyl)-1-pyrrolidinyl]sulphonyl]-phenyl]methoxy]-4-(1H-imidazol-1-yl)-2-methylquinoline, tartrate Working analogously to Example 2, starting from the compound obtained according to Example 144, the expected product is obtained in the form of a pale yellow solid (Yield=95%).

M.p.=138° C.
$[\alpha]^{27}_D$=−10° (c=0.72; $CH_3OH$)

EXAMPLE 146

8-[[2,6-Dichloro-3-[[2(S)-[(4-methyl-1-piperazinyl)carbonyl]-1-pyrrolidinyl]-sulphonyl]phenyl]methoxy]-4-(1H-imidazol-1-yl)-2-methylquinoline Working analogously to Example 1, starting from 1-methylpiperazine, the expected product is obtained in the form of a colourless oil (Yield=34%).

$[\alpha]^{27}_D$=+11° (c=0.62; $CHCl_3$)
$^1$H NMR (300 MHz; DMSOd6) 8.13 (t, J=8.6 Hz, 1H); 8.09 (s, 1H); 7.80 (d, J=8.6 Hz, 1H); 7.67 (s, 1H); 7.6–7.50 (m, 3H); 7.35–7.20 (m, 2H); 5.56 (s, 2H); 5.0–4.95 (m, 1H); 3.6–3.3 (m, 6H); 2.67 (s, 3H); 2.3–2.1 (m, 5H); 2.16 (s, 3H); 2.0–1.80 (m, 3H).

EXAMPLE 147

8-[[2,6-Dichloro-3-[[2(S)-[(4-methyl-1-piperazinyl)carbonyl]-1-pyrrolidinyl]-sulphonyl]phenyl]methoxy]-4-(1H-imidazol-1-yl)-2-methylquinoline, tartrate Working analogously to Example 2 starting from the compound obtained according to Example 146, the expected product is obtained in the form of a pale yellow solid (Yield=94%).

M.p.=138° C.
$[\alpha]^{27}_D$=−13° (c=0.60; $CH_3OH$)

EXAMPLE 148

8-[[2,6-Dichloro-3-[[2(S)-[(4-phenyl-1-piperazinyl)carbonyl]-1-pyrrolidinyl]-sulphonyl]phenyl]methoxy]-4-(1H-imidazol-1-yl)-2-methylquinoline Working analogously to Example 1, starting from 1-phenylpiperazine, the expected product is obtained in the form of a white solid (Yield=77%).

M.p.=88° C.
$[\alpha]^{28}_D$=+15° (c=0.58; $CHCl_3$)

EXAMPLE 149

8-[[2,6-Dichloro-3-[[2(S)-[(4-phenyl-1-piperazinyl)carbonyl]-1-pyrrolidinyl]-sulphonyl]phenyl]methoxy]-4-(1H-imidazol-1-yl)-2-methylquinoline, methanesulphonate Working analogously to Example 2, starting from the compound obtained according to Example 148, the expected product is obtained in the form of a pale yellow solid (Yield=93%).

M.p.=147° C.
$[\alpha]^{28}_D$=−3° (c=0.50; $CH_3OH$)

EXAMPLE 150

1-[[2,4-Dichloro-3-[[[4-(1H-imidazol-1-yl)-2-methyl-8-quinolinyl]oxy]methyl]-phenyl]sulphonyl]-N-[2-(2-pyridinyl)ethyl]-2(S)-pyrrolidinecarboxamide Working analogously to Example 1, starting from 2-(2-pyridyl)-ethylamine, the expected product is obtained in the form of a white solid (Yield=87%).

M.p.=82° C.
$[\alpha]^{25}_D$=−29° (c=1.13; $CHCl_3$)

EXAMPLE 151

1-[[2,4-Dichloro-3-[[[4-(1H-imidazol-1-yl)-2-methyl-8-quinolinyl]oxy]methyl]-phenyl]sulphonyl]-N-[2-(2-pyridinyl)ethyl]-2(S)-pyrrolidinecarboxamide, methanesulphonate Working analogously to Example 6, starting from the compound obtained according to Example 150, the expected product is obtained in the form of a pale yellow solid (Yield=85%).

M.p.=110° C.
$[\alpha]^{26}_D$=−31° (c=0.61; $CH_3OH$)

EXAMPLE 152

1-[[2,4-Dichloro-3-[[[4-(1H-imidazol-1-yl)-2-methyl-8-quinolinyl]oxy]methyl]-phenyl]sulphonyl]-N-[2-(3-pyridinyl)ethyl]-2(S)-pyrrolidinecarboxamide Working analogously to Example 1, starting from 2-(3-pyridinyl)-ethylamine, the expected product is obtained in the form of a white solid (Yield=87%).

M.p.=117° C.

$[\alpha]^{29}_D = -41°$ (c=0.59; CHCl$_3$)

EXAMPLE 153

1-[[2,4-Dichloro-3-[[[4-(1H-imidazol-1-yl)-2-methyl-8-quinolinyl]oxy]methyl]-phenyl]sulphonyl]-N-[2-(3-pyridinyl)ethyl]-2(S)-pyrrolidinecarboxamide, methanesulphonate Working analogously to Example 6, starting from the compound obtained according to Example 152, the expected product is obtained in the form of a pale yellow solid (Yield=92%).

M.p.=128° C.

$[\alpha]^{29}_D = -23°$ (c=0.74; CH$_3$OH)

EXAMPLE 154

1-[[2,4-Dichloro-3-[[[4-(1H-imidazol-1-yl)-2-methyl-8-quinolinyl]oxy]methyl]-phenyl]sulphonyl]-N-[2-(4-pyridinyl)ethyl]-2(S)-pyrrolidinecarboxamide Working analogously to Example 1, starting from 2-(4-pyridinyl)-ethylamine, the expected product is obtained in the form of a beige solid (Yield=94%).

M.p.=120° C.

$[\alpha]^{27}_D = -45°$ (c=0.56; CHCl$_3$)

EXAMPLE 155

1-[[2,4-Dichloro-3-[[[4-(1H-imidazol-1-yl)-2-methyl-8-quinolinyl]oxy]methyl]-phenyl]sulphonyl]-N-[2-(4-pyridinyl)ethyl]-2(S)-pyrrolidinecarboxamide, methanesulphonate Working analogously to Example 6, starting from the compound obtained according to Example 154, the expected product is obtained in the form of a white solid (Yield=93%).

M.p.=136° C.

$[\alpha]^{27}_D = -18°$ (c=0.76; CH$_3$OH)

EXAMPLE 156

1-[[2,4-Dichloro-3-[[[4-(1H-imidazol-1-yl)-2-methyl-8-quinolinyl]oxy]methyl]-phenyl]sulphonyl]-N-(phenylmethyl)-2(S)-pyrrolidinecarboxamide Working analogously to Example 1, starting from benzylamine, the expected product is obtained in the form of a white solid (Yield=97%).

M.p.=116° C.

$[\alpha]^{27}_D = -31°$ (c=0.77; CHCl$_3$)

EXAMPLE 157

1-[[2,4-Dichloro-3-[[[4-(1H-imidazol-1-yl)-2-methyl-8-quinolinyl]oxy]methyl]-phenyl]sulphonyl]-N-(phenylmethyl)-2(S)-pyrrolidinecarboxamide, methane-sulphonate Working analogously to Example 6, starting from the compound obtained according to Example 156, the expected product is obtained in the form of a pale yellow solid (Yield=91%).

M.p.=135° C.

$[\alpha]^{25}_D = -103°$ (c=0.83; CH$_3$OH)

Preparation LII

4-[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]-1-piperazinecarboxylic acid, 1,1-dimethylethyl ester Working analogously to Example 1, starting from t-butyl ester of 1-piperazinecarboxylic acid (N-boc-piperazine), the expected product is obtained in the form of a white solid (Yield=33%).

M.p.=98° C.

$[\alpha]^{25}_D = +4°$ (c=0.79; CHCl$_3$)

EXAMPLE 158

8-[[2,6-Dichloro-3-[[2(S)-(1-piperazinylcarbonyl)-1-pyrrolidinyl]sulphonyl]-phenyl]methoxy]-4-(1H-imidazol-1-yl)-2-methyl-quinoline, bis trifluoroacetate Working analogously to Example 13, starting from the compound obtained according to Preparation LII, the expected product is obtained in the form of a pale yellow solid (Yield=99%).

M.p.=143° C.

$[\alpha]^{19}_D = +22°$ (c=0.47; CH$_3$OH)

EXAMPLE 159

8-[[2,6-Dichloro-3-[[2(S)-[[4-(2-pyridinylmethyl)-1-piperazinyl]carbonyl]-1-pyrrolidinyl]sulphonyl] phenyl]methoxy]-4-(1H-imidazol-1-yl)-2-methyl-quinoline Working analogously to Example 127, starting from the compound obtained according to Example 158 and 2-picolyl chloride, the expected product is obtained in the form of a yellow oil (Yield=54%).

$[\alpha]^{20}_D = +11°$ (c=0.54; CHCl$_3$)

$^1$H NMR (250 MHz; DMSOd6) 8.5–8.45 (m, 1H); 8.2–8.05 (m, 2H); 7.85–7.70 (m, 2H); 7.68–7.64 (m, 1H); 7.6–7.5 (m, 3H); 7.42 (d, J=7.8 Hz, 1H); 7.35–7.20 (m, 3H); 5.56 (s, 2H); 5–4.95 (m, 1H); 3.60 (s, 2H); 3.55–3.30 (m, 6H); 2.66 (s, 3H); 2.45–2.15 (m, 5H); 2–1.8 (m, 3H).

EXAMPLE 160

8-[[2,6-Dichloro-3-[[2(S)-[[4-(2-pyridinylmethyl)-1-piperazinyl]carbonyl]-1-pyrrolidinyl]sulphonyl] phenyl]methoxy]-4-(1H-imidazol-1-yl)-2-methyl-quinoline, methanesulphonate Working analogously to Example 6, starting from the compound obtained according to Example 159, the expected product is obtained in the form of a pale yellow solid (Yield=91%).

M.p.=143° C.

$[\alpha]^{26}_D = -12°$ (c=0.56; CH$_3$OH)

EXAMPLE 161

8-[[2,6-Dichloro-3-[[2(S)-[[4-(3-pyridinylmethyl)-1-piperazinyl]carbonyl]-1-pyrrolidinyl]sulphonyl] phenyl]methoxy]-4-(1H-imidazol-1-yl)-2-methyl-quinoline Working analogously to Example 159, starting from 3-picolyl chloride, the expected product is obtained in the form of a white solid (Yield=26%).

M.p.=102° C.
[α]$^{22}_D$=+12° (c=0.40; CHCl$_3$)

EXAMPLE 162

8-[[2,6-Dichloro-3-[[2(S)-[[4-(3-pyridinylmethyl)-1-piperazinyl]carbonyl]-1-pyrrolidinyl]sulphonyl]phenyl]methoxy]-4-(1H-imidazol-1-yl)-2-methyl-quinoline, methanesulphonate Working analogously to Example 6, starting from the compound obtained according to Example 161, the expected product is obtained in the form of a pale yellow solid (Yield=95%).
M.p.=154° C.
[α]$^{26}_D$=−8° (c=0.72; CH$_3$OH)

EXAMPLE 163

8-[[2,6-Dichloro-3-[[2(S)-[[4-(4-pyridinylmethyl)-1-piperazinyl]carbonyl]-1-pyrrolidinyl]sulphonyl]phenyl]methoxy]-4-(1H-imidazol-1-yl)-2-methyl-quinoline Working analogously to Example 159, starting from 4-picolyl chloride, the expected product is obtained in the form of a beige fine solid (Yield=52%).
M.p.=108° C.
[α]$^{22}_D$=+12° (c=0.40; CHCl$_3$)

EXAMPLE 164

8-[[2,6-Dichloro-3-[[2(S)-[[4-(4-pyridinylmethyl)-1-piperazinyl]carbonyl]-1-pyrrolidinyl]sulphonyl]phenyl]methoxy]-4-(1H-imidazol-1-yl)-2-methyl-quinoline, methanesulphonate Working analogously to Example 6, starting from the compound obtained according to Example 163, the expected product is obtained in the form of a yellow solid (Yield=97%).
M.p.=156° C.
[α]$^{23}_D$=−14° (c=0.77; CH$_3$OH)

Preparation LIII

1-[[2,4-Dichloro-3-[[[2-methyl-4-(1H-1,2,4-triazol-1-yl)-2-methyl-8-quinolinyl]oxy]methyl]phenyl]sulphonyl]-N-[[1-[2-(acetoxy)ethyl]-4-piperidinyl]methyl]-2(S)-pyrrolidinecarboxamide Working analogously to Preparation XIII, starting from the compound obtained according to Example 26 and 2-bromoethyl acetate, the expected product is obtained in the form of a colourless oil (Yield=31%).
[α]$^{29}_D$=−47° (c=0.55; CHCl$_3$)
$^1$H NMR (250 MHz; DMSOd6) 9.18 (s, 1H); 8.44 (s, 1H); 8.10 (d, J=8.6 Hz, 1H); 7.93 (t, J=5.4 Hz, NH); 7.81 (d, J=8.7 Hz, 1H); 7.73 (s, 1H); 7.6–7.5 (m, 3H); 5.58 (s, 2H); 4.4–4.3 (m, 1H); 4.06 (t, J=6 Hz, 2H); 3.6–3.5 (m, 1H); 3.45–3.30 (m, 1H); 2.95–2.75 (m, 4H); 2.69 (s, 3H); 2.50–2.45 (m, 2H); 2.25–1.75 (6H); 1.99 (s, 3H); 1.55–1.45 (m, 2H); 1.35–1.20 (m, 1H); 1.15–0.95 (m, 2H).

EXAMPLE 165

1-[[2,4-Dichloro-3-[[[2-methyl-4-(1H-1,2,4-triazol-1-yl)-2-methyl-8-quinolinyl]oxy]methyl]phenyl]sulphonyl]-N-[[1-[(2-hydroxyethyl)-4-piperidinyl]methyl]-2(S)-pyrrolidinecarboxamide Working analogously to Example 11, starting from the compound obtained according to Preparation LIII, the expected product is obtained in the form of a white solid (Yield=90%).
M.p.=115° C.
[α]$^{29}_D$=−43° (c=0.58; CHCl$_3$)

EXAMPLE 166

1-[[2,4-Dichloro-3-[[[2-methyl-4-(1H-1,2,4-triazol-1-yl)-2-methyl-8-quinolinyl]oxy]methyl]phenyl]sulphonyl]-N-[[1-(2-hydroxyethyl)-4-piperidinyl]methyl]-2(S)-pyrrolidinecarboxamide, methanesulphonate Working analogously to Example 6, starting from the compound obtained according to Example 165, the expected product is obtained in the form of a white solid (Yield=82%).
M.p.=137° C.
[α]$^{26}_D$=−60° (c=0.14; CH$_3$OH)

EXAMPLE 167

1-[[2,4-Dichloro-3-[[[4-(1H-imidazol-1-yl)-2-methyl-8-quinolinyl]oxy]methyl-phenyl]sulphonyl]-N-[5-(dimethylamino)pentyl]-2(S)-pyrrolidinecarboxamide Working analogously to Example 1, starting from N,N-dimethyl-1,5-pentanediamine, the expected product is obtained in the form of a white solid (Yield=53%).
M.p.=85° C.
[α]$^{28}_D$=−31° (c=0.37; CH$_3$OH)

EXAMPLE 168

1-[[2,4-Dichloro-3-[[[4-(1H-imidazol-1-yl)-2-methyl-8-quinolinyl]oxy]methyl-phenyl]sulphonyl]-N-[5-(dimethylamino)pentyl]-2(S)-pyrrolidinecarboxamide, tartrate Working analogously to Example 2, starting from the compound obtained according to Example 167, the expected product is obtained in the form of a white solid (Yield=97%).
M.p.=126° C.
[α]$^{28}_D$=−31,6° (c=0.38; CH$_3$OH)

Preparation LIV

1-[[3-(Bromomethyl)-2,4-dichlorophenyl]sulphonyl]-3(R)-pyrrolidinol

Working analogously to Preparation VII, starting from 3(R)-pyrrolidinol, the expected product is obtained in the form of white crystals (Yield=63%).
M.p.=121° C.
[α]$^{25}_D$=+7.9° (c=0.51; CH$_3$OH)

EXAMPLE 169

1-[[2,4-Dichloro-3-[[[4-(1H-imidazol-1-yl)-2-methyl-8-quinolinyl]oxy]methyl-phenyl]sulphonyl]-3(R)-pyrrolidinol Working analogously to Preparation I, starting from the compound obtained according to Preparation LIV, the expected product is obtained in the form of white crystals (Yield=28%).
M.p.=166° C.
[α]$^{25}_D$=−2.1° (c=0.66; CH$_3$OH)

EXAMPLE 170

1-[[2,4-Dichloro-3-[[[4-(1H-imidazol-1-yl)-2-methyl-8-quinolinyl]oxy]methyl]-phenyl]sulphonyl]-3(R)-pyrrolidinol, tartrate Working analogously to Example 2, starting from the compound obtained according to Example 169, the expected product is obtained in the form of a pale yellow fine solid (Yield=97%).

M.p.=162° C.

$[\alpha]^{25}_D$=+1.65° (c=0.59; $CH_3OH$)

Preparation LV

1-[[3-(Bromomethyl)-2,4-dichlorophenyl]sulphonyl]-3(S)-pyrrolidinol

Working analogously to Preparation VII, starting from 3(S)-pyrrolidinol, the expected product is obtained in the form of white crystals (Yield=49%).

M.p.=120° C.

$[\alpha]^{25}_D$=−6° (c=0.61; $CH_3OH$)

EXAMPLE 171

1-[[2,4-Dichloro-3-[[[4-(1H-imidazol-1-yl)-2-methyl-8-quinolinyl]oxy]methyl]-phenyl]sulphonyl]-3(S)-pyrrolidinol Working analogously to Preparation I, starting from the compound obtained according to Preparation LV, the expected product is obtained in the form of white crystals (Yield=31%).

M.p.=166° C.

$[\alpha]^{25}_D$=+2.3° (c=0.54; $CH_3OH$)

EXAMPLE 172

1-[[2,4-Dichloro-3-[[4-(1H-imidazol-1-yl)-2-methyl-8-quinolinyl]oxy]methyl]-phenyl]sulphonyl]-3(S)-pyrrolidinol, tartrate Working analogously to Example 2, starting from the compound obtained according to Example 171, the expected product is obtained in the form of a beige fine solid (Yield=99%).

M.p.=163° C.

$[\alpha]^{25}_D$=+3.45° (c=0.67; $CH_3OH$)

Preparation LVI

N-[1-[[3-(Bromomethyl)-2,4-dichlorophenyl]sulphonyl]-3(R)-pyrrolidinyl]-acetamide Working analogously to Preparation VII, starting from N-[3(R)-pyrrolidinyl]acetamide, the expected product is obtained in the form of a white solid (Yield=81%).

M.p.=222° C.

$[\alpha]^{25}_D$=−1.3° (c=1.12; $CHCl_3$)

EXAMPLE 173

N-[1-[[2,4-Dichloro-3-[[[4-(1H-imidazol-1-yl)-2-methyl-8-quinolinyl]oxy]-methyl]phenyl]sulphonyl]-3(R)-pyrrolidinyl]acetamide Working analogously to Preparation I, starting from the compound obtained according to Preparation LVI, the expected product is obtained in the form of a white solid (Yield=69%).

M.p.=246° C.

$[\alpha]^{25}_D$=+26.2° (c=0.80; $CH_3OH$)

Preparation LVII

N-[1-[[3-(Bromomethyl)-2,4-dichlorophenyl]sulphonyl]-3(S)-pyrrolidinyl]-acetamide Working analogously to Preparation VIII, starting from N-[3(S)-pyrrolidinyl]acetamide, the expected product is obtained in the form of a white solid (Yield=86%).

M.p.=221° C.

$[\alpha]^{25}_D$=+1.7° (c=0.98; $CHCl_3$)

EXAMPLE 174

N-[1-[[2,4-Dichloro-3-[[[4-(1H-imidazol-1-yl)-2-methyl-8-quinolinyl]oxy]-methyl]phenyl]sulphonyl]-3(S)-pyrrolidinyl]acetamide Working analogously to Preparation I, starting from the compound obtained according to Preparation LVII, the expected product is obtained in the form of a white solid (Yield=69%).

M.p.=246° C.

$[\alpha]^{25}_D$=−26.6° (c=1.2; $CH_3OH$)

Preparation LVIII

N-[3-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]propyl]-N-methylglycine, 1-1dimethylethyl ester Working analogously to Preparation XVI, starting from the compound obtained according to Example 123, the expected product is obtained in the form of a white solid (Yield=67%).

M.p.=74° C.

$[\alpha]^{24}_D$=−33° (c=0.36; $CH_3OH$)

EXAMPLE 175

N-[3-[[[1-[[2,4-Dichloro-3-[[[4-(1H-imidazol-1-yl)-2-methyl-8-quinolinyl]oxy]-methyl]phenyl]sulphonyl]-2(S)-pyrrolidinyl]carbonyl]amino]propyl]-N-methylglycine, bis trifluoroacetate Working analogously to Example 13, starting from the compound obtained according to Preparation LVIII, the expected product is obtained in the form of a yellow powder (Yield=78%).

M.p.=115° C.

$[\alpha]^{25}_D$=−31° (c=0.40; $CH_3OH$)

Preparation LIX

1[[3-(Bromomethyl)-2,4-dichlorophenyl]sulphonyl]-2(S)-piperidinecarboxylic acid, methyl ester A solution of 0.68 g ($3.78 \times 10^{-3}$ mol) of the hydrochloride of the methyl ester of 2(S)-piperidinecarboxylic acid is prepared in 30 ml of acetonitrile and 1.14 g ($11.4 \times 10^{-3}$ mol) of potassium bicarbonate dissolved in 10 ml of water are added, and then 1.28 g ($3.78 \times 10^{-3}$ mol) of 3-(bromomethyl)-2,4-dichloro-benzenesulphonyl chloride. The reaction mixture is kept for 20 hours at ambient temperature with stirring and then concentrated under reduced pressure. The residue is taken up again with dichloromethane and this organic phase is washed with water, dried over magnesium sulphate and concentrated under reduced pressure. The crude product is purified by chromatography on silica gel eluting with the aid of a toluene/ethyl acetate (95/5; v/v) mixture. 1.02 g of the expected product are thus obtained in the form of a white solid (Yield=61%).

M.p.=91° C.

$[\alpha]^{25}_D$=+4° (c=0.56; $CH_3OH$)

Note: the expected product contains a proportion of analogue chloromethylated in position 3 which can react like the expected product during the following step and has not been separated.

Preparation LX

1[[2,4-Dichloro-3-[[[4-(1H-imidazol-1-yl)-2-methyl-8-quinolinyl]oxy]methyl]-phenyl]sulphonyl]-2(S)-piperidinecarboxylic acid, methyl ester Working analogously to Preparation I, starting from the compound obtained according to Preparation LIX, the expected product is obtained in the form of an ecru white solid (Yield=72%).

M.p.=81° C.

$[\alpha]^{25}_D$=+13° (c=0.380; $CH_3OH$)

Preparation LXI

1-[[2,4-Dichloro-3-[[[4-(1H-imidazol-1-yl)-2-methyl-8-quinolinyl]oxy]methyl]-phenyl]sulphonyl]-2(S)-piperidinecarboxylic acid Working analogously to Preparation II, starting from the compound obtained according to Preparation LX, the expected product is obtained in the form of a white solid (Yield=73%).

M.p.=208° C.

$[\alpha]^{26}_D$=−5° (c=0.30; DMSO)

EXAMPLE 176

1-[[2,4-Dichloro-3-[[[4-(1H-imidazol-1-yl)-2-methyl-8-quinolinyl]oxy]methyl]-phenyl]sulphonyl]-N-methyl-2(S)-piperidinecarboxamide Working analogously to Example 1, starting from the compound obtained according to Preparation LXI, the expected product is obtained in the form of a white solid (Yield=49%).

M.p.=74° C.

$[\alpha]^{24}_D$=+3° (c=0.30; $CH_3OH$)

EXAMPLE 177

1-[[2,4-Dichloro-3-[[[4-(1H-imidazol-1-yl)-2-methyl-8-quinolinyl]oxy]methyl]-phenyl]sulphonyl]-N-methyl-2(S)-piperidinecarboxamide, methanesulphonate Working analogously to Example 6, starting from the compound obtained according to Example 176, the expected product is obtained in the form of a yellow fine solid (Yield=77%).

M.p.=153° C.

$[\alpha]^{24}_D$=+5.2° (c=0.32; $CH_3OH$)

Preparation LXII

3-[[3-(Bromomethyl)-2,4-dichlorophenyl]sulphonyl]-4(R)-thiazolidine-carboxylic acid, methyl ester Working analogously to Preparation LIX, starting from the methyl ester of 4(R)-thiazolidinecarboxylic acid, the expected product is obtained in the form of a beige solid (Yield=15%).

M.p.=48–50° C.

$[\alpha]^{24}_D$=−40.2° (c=1.48; $CH_3OH$)

Preparation LXIII

3-[[2,4-Dichloro-3-[[[4-(1H-imidazol-1-yl)-2-methyl-8-quinolinyl]oxy]methyl]-phenyl]sulphonyl]-4(R)-thiazolidinecarboxylic acid, methyl ester Working analogously to Preparation I, starting from the compound obtained according to Preparation LXII, the expected product is obtained in the form of an off-white solid (Yield=50%).

M.p.=60° C.

$[\alpha]^{27}_D$=−31.4° (c=0.28; $CH_3OH$)

Preparation LXIV

3-[[2,4-Dichloro-3-[[[4-(1H-imidazol-1-yl)-2-methyl-8-quinolinyl]oxy]methyl]-phenyl]sulphonyl]-4(R)-thiazolidinecarboxylic acid Working analogously to Preparation II, starting from the compound obtained according to Preparation LXIII, the expected product is obtained in the form of a beige solid (Yield=60%).

M.p.=130° C.

$[\alpha]^{27}_D$=−31.8° (c=0.33; DMSO)

EXAMPLE 178

3-[[2,4-Dichloro-3-[[[4-(1H-imidazol-1-yl)-2-methyl-8-quinolinyl]oxy]methyl]-phenyl]sulphonyl]-N-methyl-4(R)-thiazolidinecarboxamide Working analogously to Example 1, starting from the compound obtained according to Preparation LXIV, the expected product is obtained in the form of a white solid (Yield=80%).

M.p.=120° C.

$[\alpha]^{27}_D$=−65.5° (c=0.36; $CH_3OH$)

EXAMPLE 179

3-[[2,4-Dichloro-3-[[[4-(1H-imidazol-1-yl)-2-methyl-8-quinolinyl]oxy]methyl]-phenyl]sulphonyl]-N-methyl-4(R)-thiazolidinecarboxamide, methanesulphonate Working analogously to Example 6, starting from the compound obtained according to Example 178, the expected product is obtained in the form of a yellow solid (Yield=99%).

M.p.=143° C.

$[\alpha]^{27}_D$=−56° (c=0.33; $CH_3OH$)

Preparation LXV

1-[3-(Bromomethyl)-2,4-dichlorophenyl]-3-pyrrolidinecarboxylic acid, methyl ester Working analogously to Preparation LIX, starting from the methyl ester of 3-pyrrolidinecarboxylic acid, the expected product is obtained in the form of a beige powder (Yield=76%).

M.p.=94° C.

Preparation LXVI

1-[[2,4-Dichloro-3-[[[4-(1H-imidazol-1-yl)-2-methyl-8-quinolinyl]oxy]methyl]-phenyl]sulphonyl]-3-pyrrolidinecarboxylic acid, methyl ester Working analogously to Preparation LX, starting from the compound obtained according to Preparation LXV, the expected product is obtained in the form of an ecru white solid (Yield=84%).

M.p.=180° C.

Preparation LXVII

1-[[2,4-Dichloro-3-[[[4-(1H-imidazol-1-yl)-2-methyl-8-quinolinyl]oxy]methyl]-phenyl]sulphonyl]-3-pyrrolidinecarboxylic acid Working analogously to Preparation LXI, starting from the compound obtained according to Preparation LXVI, the expected product is obtained in the form of a white solid (Yield=99%).

M.p.=145° C.

EXAMPLE 180

1-[[2,4-Dichloro-3-[[[4-(1H-imidazol-1-yl)-2-methyl-8-quinolinyl]oxy]methyl]-phenyl]sulphonyl]-N-methyl-3-pyrrolidinecarboxamide Working analogously to Example 1, starting from the compound obtained according to Preparation LXVII, the expected product is obtained in the form of a white solid (Yield=80%).

M.p.=108° C.

EXAMPLE 181

1-[[2,4-Dichloro-3-[[[4-(1H-imidazol-1-yl)-2-methyl-8-quinolinyl]oxy]methyl]-phenyl]sulphonyl]-N-methyl-3-pyrrolidinecarboxamide, methanesulphonate Working analogously to Example 6, starting from the compound obtained according to Example 180, the expected product is obtained in the form of a yellow solid (Yield=92%).

M.p.=137° C.

Preparation LXVIII

1-[[3-(Bromomethyl)-2,4-dichlorophenyl]sulphonyl]pyrrolidine

Working analogously to Preparation LIX, starting from pyrrolidine, the expected product is obtained in the form of a white powder (Yield=94%).

M.p.=115° C.

EXAMPLE 182

8-[[2,6-Dichloro-3-(1-pyrrolidinylsulphonyl)phenyl]methoxy]-4-(1H-imidazol-1-yl)-2-methylquinoline Working analogously to Preparation I, starting from the compound obtained according to Preparation LXVIII, the expected product is obtained in the form of a white solid (Yield=67%).

M.p.=193° C.

EXAMPLE 183

8-[[2,6-Dichloro-3-(1-pyrrolidinylsulphonyl)phenyl]methoxy]-4-(1H-imidazol-1-yl)-2-methylquinoline, hydrochloride Working analogously to Example 69, starting from the compound obtained according to Example 182, the expected product is obtained in the form of a yellow powder (Yield=99%).

M.p.=142° C.

EXAMPLE 184

1-[[2,4-Dichloro-3-[[[4-(1H-imidazol-1-yl)-2-methyl-8-quinolinyl]oxy]methyl]-phenyl]sulphonyl]-4(R)-hydroxy-N-methyl-2(S)-pyrrolidinecarboxamide Working analogously to Example 1, starting from the compound obtained according to Preparation XXVII, the expected product is obtained in the form of a white solid (Yield=49%).

M.p.=134° C.

$[\alpha]^{24}_D = +5°$ (c=0.32; CH$_3$OH)

EXAMPLE 185

1-[[2,4-Dichloro-3-[[[4-(1H-imidazol-1-yl)-2-methyl-8-quinolinyl]oxy]methyl]-phenyl]sulphonyl]-4(R)-hydroxy-N-methyl-2(S)-pyrrolidinecarboxamide, tartrate Working analogously to Example 2, starting from the compound obtained according to Example 184, the expected product is obtained in the form of a pale yellow fine solid (Yield=82%).

M.p.=125° C.

$[\alpha]^{25}_D = +10°$ (c=0.40; CH$_3$OH)

Preparation LXIX

4(R)-Methoxy-2(S)-[(methylamino)carbonyl]-1-pyrrolidinecarboxylic acid, phenylmethyl ester Working analogously to Example 1, starting from 1-(phenyl-methoxycarbonyl)-4(R)-methoxy-L-proline, the expected product is obtained in the form of a yellow solid (Yield=65%).

M.p.=45–47° C.

Preparation LXX

4(R)-Methoxy-N-methyl-2(S)-pyrrolidinecarboxamide

A solution of 1.27 g (4.34×10$^{-3}$ mol) of the compound obtained according to Preparation LXIX is prepared in 100 ml of methanol and 0.13 g of 10% palladium on carbon is added. The mixture is stirred under a hydrogen atmosphere for 2 hours at atmospheric pressure, and then filtered in order to remove the catalyst. The removal of the solvent under reduced pressure allows 0.64 g of the expected product to be obtained in the form of an oil which is used without additional purification in the following step (Yield=93%)

Preparation LXXI

1-[[3-(Bromomethyl)-2,4-dichlorophenyl]sulphonyl]-4(R)-methoxy-N-methyl-2(S)-pyrrolidinecarboxamide Working analogously to Preparation VII, starting from the compound obtained according to Preparation LXX, the expected product is obtained in the form of a white solid (Yield=80%).

M.p.=75° C.

$[\alpha]^{27}_D = +16°$ (c=0.31; CH$_3$OH)

EXAMPLE 186

1-[[2,4-Dichloro-3-[[[4-(1H-imidazol-1-yl)-2-methyl-8-quinolinyl]oxy]methyl]-phenyl]sulphonyl]-4(R)-methoxy-N-methyl-2(S)-pyrrolidinecarboxamide Working analogously to Preparation I, starting from the compound obtained according to Preparation LXXI, the expected product is obtained in the form of a white solid (Yield=40%).

M.p.=93° C.

$[\alpha]^{27}_D$=+19° (c=0.45; $CH_3OH$)

EXAMPLE 187

1-[[2,4-Dichloro-3-[[[4-(1H-imidazol-1-yl)-2-methyl-8-quinolinyl]oxy]methyl]-phenyl]sulphonyl]-4(R)-methoxy-N-methyl)-2(S)-pyrrolidinecarboxamide, methanesulphonate Working analogously to Example 6, starting from the compound obtained according to Example 186, the expected product is obtained in the form of a yellowish solid (Yield=86%).

M.p.=143° C.

$[\alpha]^{27}_D$=+17° (c=0.36; $CH_3OH$)

Preparation LXXII

4(E)-Ethoxy-1-(phenylmethoxycarbonyl)-L-proline, ethyl ester

A solution of 3 g (11.3×10⁻³ mol) of 4(E)-hydroxy-1-(phenylmethoxy-carbonyl)-L-proline is prepared in 15 ml of dimethylformamide and 1.12 g (28.2×10⁻³ mol) of sodium hydride (60% in oil) are added. After 30 min with stirring at ambient temperature, 2.10 ml (26×10⁻³ mol) of iodoethane are added. The mixture is kept for 24 hours at ambient temperature with stirring, and then poured onto 250 ml of water and extracted with ethyl acetate. The organic phase is dried over magnesium sulphate and then concentrated under reduced pressure. The residue is purified by chromatography on silica gel eluting with the aid of a toluene/ethyl acetate (95/5; v/v) mixture. 2.3 g of the expected product are thus obtained in the form of a yellow oil (Yield=63%).

$[\alpha]^{25}_D$=−42.1° (c=0.42; $CH_3OH$)

Preparation LXXIII

4(E)-Ethoxy-1-(phenylmethoxycarbonyl)-L-proline

Working analogously to Preparation II, starting from the compound obtained according to Preparation LXXII, the expected product is obtained in the form of a colourless oil (Yield=99%).

$[\alpha]^{25}_D$=−41.9° (c=0.52; $CH_3OH$)

Preparation LXXIII

4(R)-Ethoxy-1-(phenylmethoxycarbonyl)-N-methyl-2(S)-pyrrolidine-carboxamide

Working analogously to Example 1, starting from the compound obtained according to Preparation LXXII, the expected product is obtained in the form of a colourless oil (Yield=64%).

$[\alpha]^{25}_D$=−31.7° (c=0.35; $CH_3OH$)

Preparation LXXIV

4(R)-Ethoxy-N-methyl-2(S)-pyrrolidinecarboxamide

Working analogously to Preparation LXX, starting from the compound obtained according to Preparation LXXIII, the expected product is obtained in the form of a colourless oil (Yield=97%).

$[\alpha]^{25}_D$=−44.2° (c=0.29; $CH_3OH$)

Preparation LXXV

1-[[3-(Bromomethyl)-2,4-dichlorophenyl]sulphonyl]-4(R)-ethoxy-N-methyl-2(S)-pyrrolidinecarboxamide Working analogously to Preparation VII, starting from the compound obtained according to Preparation LXXIV, the expected product is obtained in the form of a beige solid (Yield=89%).

M.p.=122° C.

$[\alpha]^{25}_D$=−5.1° (c=0.25; $CH_3OH$)

EXAMPLE 188

1-[[2,4-Dichloro-3-[[[4-(1H-imidazol-1-yl)-2-methyl-8-quinolinyl]oxy]methyl]-phenyl]sulphonyl]-4(R)-ethoxy-N-methyl-2-(S)-pyrrolidinecarboxamide Working analogously to Preparation I, starting from the compound obtained according to Preparation LXXV, the expected product is obtained in the form of a white solid (Yield=34%).

M.p.=80° C.

$[\alpha]^{25}_D$=+19.2° (c=0.22; $CH_3OH$)

EXAMPLE 189

1-[[2,4-Dichloro-3-[[[4-(1H-imidazol-1-yl)-2-methyl-8-quinolyl]oxy]methyl]-phenyl]sulphonyl]-4(R)-ethoxy-N-methyl-2-(S)-pyrrolidinecarboxamide, methanesulphonate Working analogously to Example 6, starting from the compound obtained according to Example 188, the expected product is obtained in the form of a pale yellow solid (Yield=92%).

M.p.=138° C.

$[\alpha]^{25}_D$=+21.9° (c=0.30; $CH_3OH$)

Preparation LXXVI

4(E)-Propoxy-1-(phenylmethoxycarbonyl)-L-proline, propyl ester

Working analogously to Preparation LXXII, starting from iodopropane, the expected product is obtained in the form of a yellow oil (Yield=35%).

$[\alpha]^{25}_D$=−52.4° (c=0.56; $CH_3OH$)

Preparation LXXVII

4(E)-Propoxy-1-(phenylmethoxycarbonyl)-L-proline

Working analogously to Preparation II, starting from the compound obtained according to Preparation LXXVI, the expected product is obtained in the form of a yellow oil (Yield=99%).

$[\alpha]^{25}_D$=−38.3° (c=0.29; $CH_3OH$)

Preparation LXXVIII

4(R)-Propoxy-1-(phenylmethoxycarbonyl)-N-methyl-2(S)-pyrrolidine-carboxamide

Working analogously to Example 1, starting from the compound obtained according to Preparation LXXVII, the expected product is obtained in the form of a yellow oil (Yield=75%).

$[\alpha]^{25}_D$=−33° (c=0.28; $CH_3OH$)

Preparation LXXIX

4(R)-Propoxy-N-methyl-2(S)-pyrrolidinecarboxamide

Working analogously to Preparation LXX, starting from the compound obtained according to Preparation LXXVIII, the expected product is obtained in the form of a colourless oil (Yield=90%).

$[\alpha]^{25}_D=-45.4°$ (c=0.37; CH$_3$OH)

Preparation LXXX

1-[[3-(Bromomethyl)-2,4-dichlorophenyl]sulphonyl]-4(R)-propoxy-N-methyl-2(S)-pyrrolidinecarboxamide Working analogously to Preparation VII, starting from the compound obtained according to Preparation LXXIX, the expected product is obtained in the form of a beige solid (Yield=93%).

M.p.=62° C.

$[\alpha]^{25}_D=-6.9°$ (c=0.27; CH$_3$OH)

EXAMPLE 190

1-[[2,4-Dichloro-3-[[[4-(1H-imidazol-1-yl)-2-methyl-8-quinolyl]oxy]methyl]-phenyl]sulphonyl]-4(R)-propoxy-N-methyl-2-(S)-pyrrolidinecarboxamide Working analogously to Preparation I, starting from the compound obtained according to Preparation LXXX, the expected product is obtained in the form of a white solid (Yield=31%).

M.p.=84° C.

$[\alpha]^{25}_D=+25.3°$ (c=0.22; CH$_3$OH)

EXAMPLE 191

1-[[2,4-Dichloro-3-[[[4-(1H-imidazol-1-yl)-2-methyl-8-quinolyl]oxy]methyl]-phenyl]sulphonyl]-4(R)-propoxy-N-methyl-2-(S)-pyrrolidinecarboxamide, methanesulphonate Working analogously to Example 6, starting from the compound obtained according to Example 190, the expected product is obtained in the form of a pale yellow solid (Yield=94%).

M.p.=141° C.

$[\alpha]^{25}_D=+13.7°$ (c=0.30; CH$_3$OH)

Preparation LXXXI

4(E)-(Cyclopropylmethoxy)-1-(phenylmethoxycarbonyl)-L-proline, cyclopropylmethyl ester Working analogously to Preparation LXXII, starting from bromomethylcyclopropane, the expected product is obtained in the form of a yellow oil (Yield=27%).

$[\alpha]^{25}_D=-28.7°$ (c=0.33; CH$_3$OH)

Preparation LXXXII

4(E)-(Cyclopropylmethoxy)-1-(phenylmethoxycarbonyl)-L-proline,

Working analogously to Preparation II, starting from the compound obtained according to Preparation LXXXI, the expected product is obtained in the form of a colourless oil (Yield=98%).

$[\alpha]^{25}_D=-31.1°$ (c=0.25; CH$_3$OH)

Preparation LXXXIII

4(R)-(Cyclopropylmethoxy)-1-(phenylmethoxycarbonyl)-N-methyl-2(S)-pyrrolidinecarboxamide Working analogously to Example 1, starting from the compound obtained according to Preparation LXXXII, the expected product is obtained in the form of a colourless oil (Yield=74%).

$[\alpha]^{25}_D=-28.8°$ (c=0.28; CH$_3$OH)

Preparation LXXXIV

4(R)-(Cyclopropylmethoxy)-N-methyl-2(S)-pyrrolidinecarboxamide

Working analogously to Preparation LXX, starting from the compound obtained according to Preparation LXXXIII, the expected product is obtained in the form of a colourless oil (Yield=82%).

$[\alpha]^{25}_D=-34.2°$ (c=0.24; CH$_3$OH)

Preparation LXXXV

1-[[3-(Bromomethyl)-2,4-dichlorophenyl]sulphonyl]-4(R)-(cyclopropyl-methoxy)-N-methyl-2(S)-pyrrolidinecarboxamide Working analogously to Preparation VII, starting from the compound obtained according to Preparation LXXXIV, the expected product is obtained in the form of a white solid (Yield=90%).

M.p.=161° C.

$[\alpha]^{25}_D=-3.9°$ (c=0.27; CH$_3$OH)

EXAMPLE 192

1-[[2,4-Dichloro-3-[[[4-(1H-imidazol-1-yl)-2-methyl-8-quinolyl]oxy]methyl]-phenyl]sulphonyl]-4(R)-(cyclopropylmethoxy)-N-methyl-2-(S)-pyrrolidine-carboxamide.

Working analogously to Preparation I, starting from the compound obtained according to Preparation LXXXV, the expected product is obtained in the form of a white solid (Yield=59%).

M.p.=98° C.

$[\alpha]^{25}_D=+21.2°$ (c=0.23; CH$_3$OH)

EXAMPLE 193

1-[[2,4-Dichloro-3-[[[4-(1H-imidazol-1-yl)-2-methyl-8-quinolyl]oxy]methyl]-phenyl]sulphonyl]-4(R)-(cyclopropylmethoxy)-N-methyl-2-(S)-pyrrolidine-carboxamide, methanesulphonate Working analogously to Example 6, starting from the compound obtained according to Example 192, the expected product is obtained in the form of a pale yellow solid (Yield=87%).

M.p.=149° C.

$[\alpha]^{25}_D=+22.9°$ (c=0.29; CH$_3$OH)

Preparation LXXXVI

4(R)-(1,1-Dimethylethoxy)-1-(phenylmethoxycarbonyl)-N-methyl-2(S)-pyrrolidinecarboxamide Working analogously to Example 1, starting from 4(E)-(1,1-dimethyl-ethoxy)-1-(phenylmethoxycarbonyl)-L-proline, the expected product is obtained in the form of a colourless oil (Yield=86%).

$[\alpha]^{25}_D=-6.2°$ (c=0.43; CH$_3$OH)

Preparation LXXXVII

4(R)-(1,1-Dimethylethoxy)-N-methyl-2(S)-pyrrolidinecarboxamide

Working analogously to Preparation LXX, starting from the compound obtained according to Preparation LXXXVI,

Preparation LXXXVIII

1-[[3-(Bromomethyl)-2,4-dichlorophenyl]
sulphonyl]-4(R)-(1,1-dimethyl-ethoxy)-N-methyl-2
(S)-pyrrolidinecarboxamide Working analogously to Preparation VII, starting from the compound obtained according to Preparation LXXVII, the expected product is obtained in the form of a white solid (Yield=91%).

M.p.=73° C.

$[\alpha]^{25}_D = -6.4°$ (c=0.44; CH$_3$OH)

EXAMPLE 194

1-[[2,4-Dichloro-3-[[[4-(1H-imidazol-1-yl)-2-
methyl-8-quinolyl]oxy]methyl]-phenyl]sulphonyl]-4
(R)-(1,1-dimethylethoxy)-N-methyl-2-(S)-
pyrrolidine-carboxamide Working analogously to Preparation I, starting from the compound obtained according to Preparation LXXXVIII, the expected product is obtained in the form of a white solid (Yield=65%).

M.p.=84° C.

$[\alpha]^{25}_D = +19.4°$ (c=0.26; CH$_3$OH)

EXAMPLE 195

1-[[2,4-Dichloro-3-[[[4-(1H-imidazol-1-yl)-2-
methyl-8-quinolyl]oxy]methyl]-phenyl]sulphonyl]-4
(R)-(1,1-dimethylethoxy)-N-methyl-2-(S)-
pyrrolidine-carboxamide, methanesulphonate Working analogously to Example 6, starting from the compound obtained according to Example 194, the expected product is obtained in the form of a pale yellow solid (Yield=96%).

M.p.=150° C.

$[\alpha]^{25}_D = +21.6°$ (c=0.26; CH$_3$OH)

Preparation LXXXIX

1-[(1,1-Dimethylethoxy)carbonyl]-4(R)-
(phenylmethoxy)-N-methyl-2(S)-
pyrrolidinecarboxamide Working analogously to Example 1, starting from 1-[(1, 1-dimethyl-ethoxy)carbonyl]-4(E)-(phenylmethoxy)-L-proline, the expected product is obtained in the form of a colourless oil (Yield=82%).

$[\alpha]^{25}_D = -13.4°$ (c=0.14; CH$_3$OH)

Preparation XC

4(R)-(Phenylmethoxy)-N-methyl-2(S)-
pyrrolidinecarboxamide, trifluoroacetate

Working analogously to Example 9, starting from the compound obtained according to Preparation LXXXIX, the expected product is obtained in the form of a yellow solid (Yield=98%).

M.p.=54° C.

$[\alpha]^{25}_D = -3.1°$ (c=0.37; CH$_3$OH)

Preparation XCI

1-[[3-(Bromomethyl)-2,4-dichlorophenyl]
sulphonyl]-4(R)-(phenylmethoxy)-N-methyl-2(S)-
pyrrolidinecarboxamide Working analogously to Preparation VII, starting from the compound obtained according to Preparation XC, the expected product is obtained in the form of a white solid (Yield=73%).

M.p.=62–64° C.

$[\alpha]^{25}_D = -14.2°$ (c=0.37; CH$_3$OH)

EXAMPLE 196

1-[[2,4-Dichloro-3-[[[4-(1H-imidazol-1-yl)-2-
methyl-8-quinolyl]oxy]methyl]-phenyl]sulphonyl]-4
(R)-(phenylmethoxy)-N-methyl-2-(S)-pyrrolidine-
carboxamide Working analogously to Preparation I, starting from the compound obtained according to Preparation XCI, the expected product is obtained in the form of a white solid (Yield=29%).

M.p.=100° C.

$[\alpha]^{25}_D = +6.1°$ (c=0.29; CH$_3$OH)

EXAMPLE 197

1-[[2,4-Dichloro-3-[[[4-(1H-imidazol-1-yl)-2-
methyl-8-quinolyl]oxy]methyl]-phenyl]sulphonyl]-4
(R)-(phenylmethoxy)-N-methyl-2-(S)-pyrrolidine-
carboxamide, methanesulphonate Working analogously to Example 6, starting from the compound obtained according to Example 196, the expected product is obtained in the form of a white solid (Yield=96%).

M.p.=140–142° C.

$[\alpha]^{25}_D = +20.1°$ (c=0.32; CH$_3$OH)

Preparation XCII 2,5-Dihydro-1-[(1,1-dimethylethoxy)carbonyl]-N-
methyl-1H-pyrrole-2-(S)-carboxamide Working analogously to Example 1, starting from 2,5-dihydro-1-[(1,1-dimethylethoxy)carbonyl]-1H-pyrrole-2 (S)-carboxylic acid, the expected product is obtained in the form of a white solid (Yield=77%).

M.p.=47–48° C.

$[\alpha]^{19}_D = -166°$ (c=0.4; CH3OH)

Preparation XCIII 2,5-Dihydro-N-methyl-1H-pyrrole-2-(S)-
carboxamide, trifluoroacetate Working analogously to Example 9, starting from the compound obtained according to Preparation XCII, the expected product is obtained in the form of an oil (Yield=98%).

$[\alpha]^{19}_D = -67°$ (c=0.50; CH$_3$OH)

Preparation XCIV

1-[[3-(Bromomethyl)-2,4-dichlorophenyl]
sulphonyl]-2,5-dihydro-N-methyl-1H-pyrrole-2(S)-
carboxamide Working analogously to Preparation VII, starting from the compound obtained according to Preparation XCIII, the expected product is obtained in the form of a white solid (Yield=86%).

M.p.=66° C.
[α]$^{25}_D$=−111° (c=0.43; CH$_3$OH)

EXAMPLE 198

1-[[2,4-Dichloro-3-[[[4-(1H-imidazol-1-yl)-2-methyl-8-quinolinyl]oxy]methyl]-phenyl]sulphonyl]-2,5-dihydro-N-methyl-1H-pyrrole-2(S)-carboxamide Working analogously to Preparation I, starting from the compound obtained according to Preparation XCIV, the expected product is obtained in the form of a white solid (Yield=54%).
M.p.=132° C.
[α]$^{25}_D$=−92° (c=0.33; CH$_3$OH)

EXAMPLE 199

1-[[2,4-Dichloro-3-[[[4-(1H-imidazol-1-yl)-2-methyl-8-quinolinyl]oxy]methyl]-phenyl]sulphonyl]-2,5-dihydro-N-methyl-1H-pyrrole-2(S)-carboxamide, methanesulphonate Working analogously to Example 6, starting from the compound obtained according to Example 198, the expected product is obtained in the form of a yellow fine solid (Yield=99%).
M.p.=139° C.
[α]$^{25}_D$=−76° (c=0.44; CH$_3$OH)

Preparation XCV

1-[[3-(Bromomethyl)-2,4-dichlorophenyl]sulphonyl]-2(S)-azetidinecarboxylic acid, methyl ester Working analogously to Preparation VII, starting from methyl 2(S)-azetidinecarboxylate, the expected product is obtained in the form of a white solid (Yield=33%).
M.p.=150° C.
[α]$^{28}_D$=+6° (c=0.38; CH$_3$OH)

Preparation XCVI

1-[[2,4-Dichloro-3-[[[4-(1H-imidazol-1-yl)-2-methyl-8-quinolinyl]oxy]methyl]-phenyl]sulphonyl]-2(S)-azetidinecarboxylic acid, methyl ester Working analogously to Preparation I, starting from the compound obtained according to Preparation XCV, the expected product is obtained in the form of a white solid (Yield=77%).
M.p.=80° C.
[α]$^{28}_D$=+73° (c=0.32; CH$_3$OH)

Preparation XCVII

1-[[2,4-Dichloro-3-[[[4-(1H-imidazol-1-yl)-2-methyl-8-quinolinyl]oxy]methyl]-phenyl]sulphonyl]-2(S)-azetidinecarboxylic acid Working analogously to Preparation II, starting from the compound obtained according to Preparation XCVI, the expected product is obtained in the form of an ecru white solid (Yield=68%).
M.p.=160° C.
[α]$^{28}_D$=+11.6° (c=0.32; CH$_3$OH)

EXAMPLE 200

1-[[2,4-Dichloro-3-[[[4-(1H-imidazol-1-yl)-2-methyl-8-quinolinyl]oxy]methyl]-phenyl]sulphonyl]-N-methyl-2(S)-azetidinecarboxamide Working analogously to Example 1, starting from the compound obtained according to Preparation CXVII, the expected product is obtained in the form of a beige solid (Yield=98%).
M.p.=118° C.
[α]$^{28}_D$=−37.8° (c=0.33; CH$_3$OH)

EXAMPLE 201

1-[[2,4-Dichloro-3-[[[4-(1H-imidazol-1-yl)-2-methyl-8-quinolinyl]oxy]methyl]-phenyl]sulphonyl]-N-methyl-2(S)-azetidinecarboxamide, methanesulphonate Working analogously to Example 6, starting from the compound obtained according to Example 200, the expected product is obtained in the form of a yellowish solid (Yield=81%).
M.p.=135° C.
[α]$^{28}_D$=−21.1° (c=0.35; CH$_3$OH)

Preparation XCVIII

1-[[3-(Bromomethyl)-2,4-dichlorophenyl]sulphonyl]-4(E)-phenoxy-L-proline, methyl ester Working analogously to Example 127, starting from 3-(bromomethyl)-2,4-dichlorobenzenesulphonyl chloride and the methyl ester of 4(trans)-phenoxy-L-proline, the expected product is obtained in the form of a yellow oil (Yield=75%).
[α]$^{24}_D$=−16° (c=0.55; CHCl$_3$)

Preparation IC

1-[[2,4-Dichloro-3-[[[4-(1H-imidazol-1-yl)-2-methyl-8-quinolinyl]oxy]methyl]-phenyl]sulphonyl]-4(E)-phenoxy-L-proline, methyl ester Working analogously to Preparation I, starting from the compound obtained according to Preparation XCVIII, the expected product is obtained in the form of a yellow solid (Yield=75%).
M.p.=88° C.
[α]$^{23}_D$=−1.36° (c=0.5; CHCl$_3$)

Preparation C

1-[[2,4-Dichloro-3-[[[4-(1H-imidazol-1-yl)-2-methyl-8-quinolinyl]oxy]methyl]-phenyl]sulphonyl]-4(E)-phenoxy-L-proline Working analogously to Preparation II, starting from the compound obtained according to Preparation IC, the expected product is obtained in the form of a beige solid (Yield=77%).
M.p.=150° C.
[α]$^{27}_D$=+20.9° (c=0.58; DMSO)

EXAMPLE 202

1-[[2,4-Dichloro-3-[[[4-(1H-imidazol-1-yl)-2-methyl-8-quinolinyl]oxy]methyl]-phenyl]sulphonyl]-N-methyl-4(R)-phenoxy-2(S)-pyrrolidinecarboxamide Working analogously to Example 1, starting from the compound obtained according to Preparation C, the expected product is obtained in the form of a white solid (Yield=37%).
M.p.=97° C.
[α]$^{27}_D$=−2.9° (c=0.55; CH$_3$OH)

EXAMPLE 203

1-[[2,4-Dichloro-3-[[[4-(1H-imidazol-1-yl)-2-methyl-8-quinolinyl]oxy]methyl]-phenyl]sulphonyl]-N-methyl-4(R)-phenoxy-2(S)-pyrrolidinecarboxamide, methanesulphonate Working analogously to Example 6, starting from the compound obtained according to Example 202, the expected product is obtained in the form of a white solid (Yield=92%).

M.p.=147° C.

$[\alpha]^{23}_D$=−4.8° (c=0.47; CH$_3$OH)

Preparation CI

4(S)-Methoxy-N-methyl-1-[(phenylmethoxy)carbonyl]-2(S)-pyrrolidine-carboxamide

Working analogously to Example 1, starting from 4(cis)-methoxy-1-[(phenylmethoxy)-carbonyl]-L-proline, the expected product is obtained in the form of a colourless oil (Yield=76%).

$[\alpha]^{27}_D$=−38° (c=0.81; CH$_3$OH)

Preparation CII

4(S)-Methoxy-N-methyl-2(S)-pyrrolidinecarboxamide

Working analogously to Preparation LXX, starting from the compound obtained according to Preparation CI, the expected product is obtained in the form of a colourless oil (Yield=95%).

Preparation CIII

1-[[3-(Bromomethyl)-2,4-dichlorophenyl]sulphonyl]-4(S)-methoxy-N-methyl-2(S)-pyrrolidinecarboxamide Working analogously to Preparation XCVIII, starting from the compound obtained according to Preparation CII, the expected product is obtained in the form of a yellowish solid (Yield=90%).

M.p.=64° C.

$[\alpha]^{27}_D$=−17° (c=0.69; CHCl$_3$)

EXAMPLE 204

1-[[2,4-Dichloro-3-[[[4-(1H-imidazol-1-yl)-2-methyl-8-quinolinyl]oxy]methyl]-phenyl]sulphonyl]-4(S)-methoxy-N-methyl-2(S)-pyrrolidinecarboxamide Working analogously to Preparation I, starting from the compound obtained according to Preparation CIII, the expected product is obtained in the form of a white solid (Yield=72%).

M.p.=64° C.

$[\alpha]^{23}_D$=−22.7° (c=0.51; CHCl$_3$)

EXAMPLE 205

1-[[2,4-Dichloro-3-[[[4-(1H-imidazol-1-yl)-2-methyl-8-quinolinyl]oxy]methyl]-phenyl]sulphonyl]-4(S)-methoxy-N-methyl-2(S)-pyrrolidinecarboxamide, methanesulphonate Working analogously to Example 6, starting from the compound obtained according to Example 204, the expected product is obtained in the form of a yellow solid (Yield=90%).

M.p.=135° C.

$[\alpha]^{27}_D$=−5.3° (c=0.4; CH$_3$OH)

EXAMPLE 206

1-[[2,4-Dichloro-3-[[[2-methyl-4-(1H-1,2,4-triazol-1-yl)-2-methyl-8-quinolinyl]oxy]methyl]phenyl]sulphonyl]-4(R)-methoxy-N-methyl-2(S)-pyrrolidinecarboxamide Working analogously to Example 186, starting from 8-hydroxy-2-methyl-4-(1H-1,2,4-triazol-1-yl)quinoline, the expected product is obtained in the form of a white solid (Yield=62%).

M.p.=73° C.

$[\alpha]^{27}_D$=+17.2° (c=0.68; CH$_3$OH)

EXAMPLE 207

1-[[2,4-Dichloro-3-[[[2-methyl-4-(1H-1,2,4-triazol-1-yl)-2-methyl-8-quinolinyl]oxy]methyl]phenyl]sulphonyl]-4(R)-methoxy-N-methyl-2(S)-pyrrolidinecarboxamide, methanesulphonate Working analogously to Example 6, starting from the compound obtained according to Example 206, the expected product is obtained in the form of a yellow solid (Yield=87%).

M.p.=134° C.

$[\alpha]^{23}_D$=+38° (c=0.52; CH$_3$OH)

The activity of the products according to the invention was evaluated, according to a first aspect, as a function of their aptitude to bind to the bradykinin B$_2$ receptors. It is known that the kinins, of which one of the principal representatives is bradykinin, form a group of small peptides which contribute significantly to the inflammatory response and therefore appear to be involved in the pathology of inflammatory diseases. It is likewise known that bradykinin is amongst one of the most powerful algesic agents known. The mode of action of kinins and more particularly of bradykinin makes a coupling of the peptides to the two types of receptors called B$_1$ and B$_2$ respectively take place. The B$_2$ receptor belongs to the large family of receptors with seven transmembrane domains coupled to the G proteins and seems to be more particularly involved in the field of the pathologies mentioned above. This is the reason why the products of the invention, which have the property of being able to bind to the B$_2$ receptor, inhibit the binding of bradykinin and, consequently, suppress its harmful activity. The test employed in order to measure this property is a competitive binding test on CHO cell membranes expressing the human B$_2$ receptor using bradykinin labelled with tritium ([$^3$H]-bradykinin) as ligand.

The results are expressed by the K$_i$ value, as calculated according to the recommended method with the description of the test employed and described according to D. Pruneau et al., in Br. J. Pharmacol. 1998, 125 p 365–372.

According to a second aspect of the control of the activity, it was important to verify that the products of the invention indeed have a bradykinin-antagonist character towards the B$_2$ receptor, that is to say that the compound, after binding to the B$_2$ receptor, does not cause the symptoms analogous to those caused by the binding of bradykinin to the said B$_2$ receptor. This antagonist character is expressed by the value pA$_2$, calculated according to a biological test employed in order to measure the inhibition of the contraction of the isolated human umbilical vein by the compounds according to the invention in the presence of bradykinin. The test procedure and the method of calculation of $pA_2$ are described in the articles of D. Pruneau et al. published in Br. J. Pharmacol. 1998, 125, p 365–372 and J L. Paquet et al. Br. J. Pharmacol. 1999, 126 (in print).

The values obtained with certain compounds of the invention are collected in Table I below. The values found for the $K_i$ show values lower than 1 nM, testifying to an excellent affinity of the compounds for the bradykinin $B_2$ receptor. The values found for $pA_2$ are representative of the antagonist character of the compounds towards the bradykinin $B_2$ receptor.

The compounds of the present invention, because of their bradykinin-antagonist property towards its $B_2$ receptor, are useful in the treatment of pain, and in the treatment of numerous pathologies involving bradykinin or its homologues. Among these pathologies are included septic and haemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angiooedema, migraine, encephalomyelitis, meningitis, cerebrovascular accidents (especially those caused by a traumatic cerebral shock), certain neurological disorders, inflammatory vascular conditions (for example: atherosclerosis and arthritis of the lower members), painful conditions (for example cephalagia, dental pain, menstrual pain), premature uterine contractions, cystitis and burns. The compounds according to the invention can likewise be useful for potentiating antiviral agents.

The compounds of the present invention, which can be used in the form of free base or of their non-toxic addition salts, in combination with a physiologically acceptable excipient, are in general prescribed in human therapeutics at doses of approximately 1 to 1000 mg/day, in a form administrable by the oral route, by intravenous, intramuscular or subcutaneous injection, by the transdermal route, by means of aerosols or by means of suppositories. These compounds are likewise administrable by the topical route, especially in gel or ointment form.

The compounds of the present invention likewise find their use in the cosmetics field for treating pathologies of the skin or of the scalp.

TABLE I

| | Biological activity | |
|---|---|---|
| Examples | $K_i$ (nM) | $pA_2$ |
| 4 | 0.24 | 10 |
| 10 | 1.0 | 8.5 |
| 12 | 0.47 | 8.7 |
| 23 | 0.45 | 9.1 |
| 30 | 0.73 | 8.7 |
| 32 | 1.4 | 9.1 |
| 42 | 77 | 8.3 |
| 48 | 32 | 8.5 |
| 50 | 30 | 8.3 |
| 61 | 21 | 8.1 |
| 64 A | 0.034 | 9.3 |
| 73 | 10 | 8.4 |
| 75 | 2.8 | 8.3 |
| 77 | 6.1 | 8.6 |
| 83 | 14 | 7.9 |
| 87 | 15 | 8.2 |
| 89 | 55 | 8.0 |
| 101 | 50 | 8.4 |
| 103 | 21 | 7.9 |
| 105 | 7.7 | 8.3 |

TABLE I-continued

| | Biological activity | |
|---|---|---|
| Examples | $K_i$ (nM) | $pA_2$ |
| 109 | 15 | 8.3 |
| 115 | 35 | 8.5 |
| 123 | 8.1 | 8.4 |
| 166 | 5.8 | 8.2 |
| 170 | 7.8 | 8.0 |
| 174 | 8.8 | 8.1 |

What is claimed is:

1. A heterocyclic benzenesulphonamide compound of formula (I):

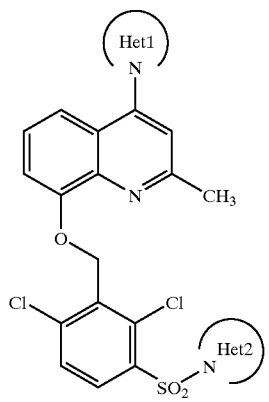

wherein, Het1 is a 5-membered nitrogen-containing heterocycle,

Het2 is

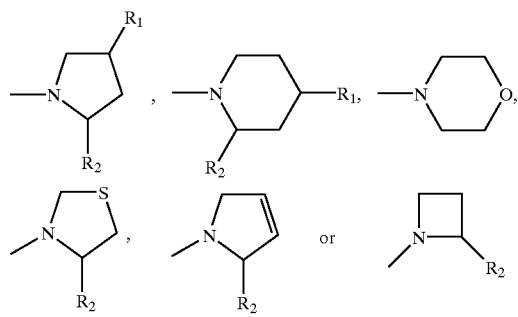

wherein $R_1$ is hydrogen, hydroxyl, $C_1$–$C_4$ alkoxy, phenoxy, phenylmethoxy, —$CH_2OH$, cycloalkyloxy, cycloalkylalkoxy (where each cycloalkyl fragment is $C_3$–$C_8$ and the alkoxy fragment is $C_1$–$C_4$), —NH—CO—$CH_3$, —CO—$NH_2$ or —CO—NH—$CH_3$, $R_2$ is hydrogen, —$CH_2OH$, —$CH_2$—O—$CH_3$, —$CONR_3R_4$,

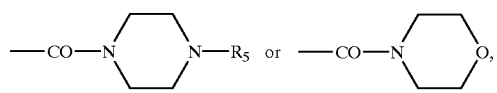

wherein $R_3$ is hydrogen, $C_1$–$C_3$ alkyl, $C_3$–$C_8$ cycloalkyl, ($C_3$–$C_8$) cycloakyl ($C_1$–$C_3$) alkyl, phenyl, or phenylmethyl, R$_4$ is hydrogen, C$_1$–C$_3$ alkyl, —(CH$_2$)n—CH$_2$OH, —(CH$_2$)n—COOH, —(CH$_2$)n—CH$_2$—NR$_5$R$_6$,

R$_5$ is hydrogen, C$_1$–C$_3$ alkyl, phenyl, phenylmethyl, pyridinyl, pyridinylmethyl, pyridinylethyl, benzoyl, 4-(aminoiminomethyl)benzoyl, —(CH$_2$)$_m$—CH$_2$OH, —(CH$_2$)$_m$—COOH, —(CH$_2$)$_m$CH$_2$—O—(CH$_2$)$_m$—CH$_2$OH, —CO—(CH$_2$)$_m$—COOH, or

R$_6$ is hydrogen, C$_1$–C$_3$ alkyl group, or R$_5$ and R$_6$ together form, with the nitrogen atom to which they are attached, a 5- or 6-membered N heterocycle;
n=1, 2, 3 or 4; and
m=1, 2 or 3;
and the addition salts thereof.

2. A compound of formula (I) according to claim 1, wherein Het1 is 1-(1H)-imidazolyl.

3. A compound of formula (I) according to claim 1, wherein Het2 is

wherein R$_3$ is hydrogen or C$_1$–C$_3$ alkyl, and
R$_4$ is C$_1$–C$_3$ alkyl, —(CH$_2$)n—CH$_2$—NR$_5$R$_6$, pyridinylmethyl, or

wherein R$_5$ is (CH$_2$)$_m$—CH$_2$OH, pyridinylmethyl, or 4-(aminoiminomethyl)benzoyl and
R$_6$ is methyl, or along with R$_5$ and the nitrogen to which they are bonded, forms a 5- or 6-membered saturated heterocycle.

4. A compound of formula (I) according to claim 1, wherein Het2 is

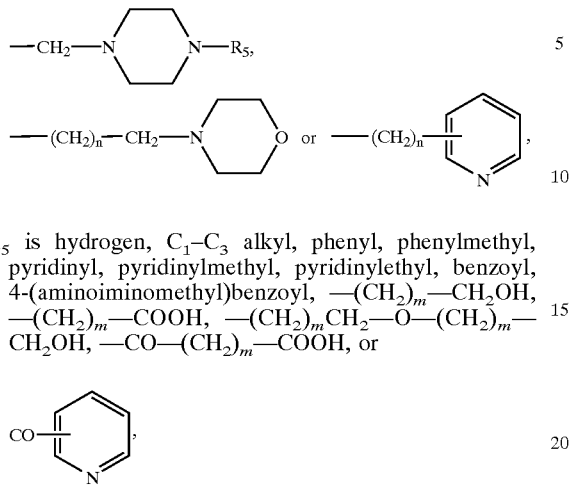

wherein R$_5$ is a pyridinyl group or a pyridinylmethyl group.

5. A method of preparing a compound of formula (I),

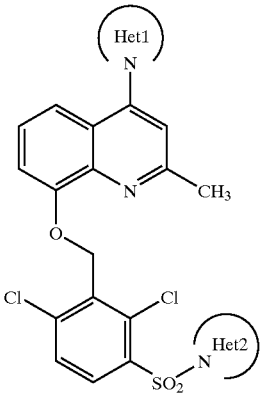

(I)

wherein, Het1 is a 5-membered nitrogen-containing heterocycle,
Het2 is

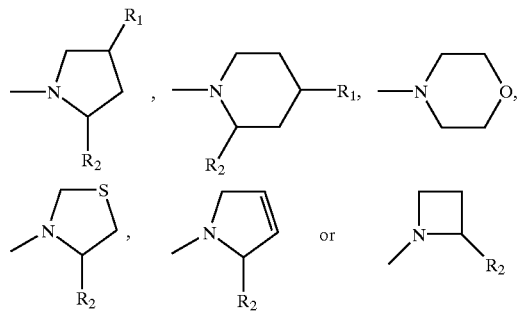

wherein R$_1$ is hydrogen, hydroxyl, C$_1$–C$_4$ alkoxy, phenoxy, phenylmethoxy, —CH$_2$OH, cycloalkyloxy, cycloalkylalkoxy (where each cycloalkyl fragment is C$_3$–C$_8$ and the alkoxy fragment is C$_1$–C$_4$), —NH—CO—CH$_3$, —CO—NH$_2$ or —CO—NH—CH$_3$,
R$_2$ is hydrogen, —CH$_2$OH, —CH$_2$—O—CH$_3$, —CONR$_3$R$_4$,

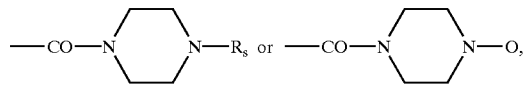

wherein R$_3$ is hydrogen, C$_1$–C$_3$ alkyl, C$_3$–C$_8$ cycloalkyl, (C$_3$–C$_8$) cycloalkyl (C$_1$–C$_3$) alkyl, phenyl, or phenylmethyl,
R$_4$ is hydrogen, C$_1$–C$_3$ alkyl, —(CH$_2$)n—CH$_2$OH, —(CH$_2$)n—COOH, —(CH$_2$)n—CH$_2$—NR$_5$R$_6$,

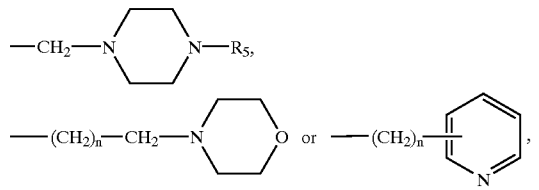

R$_5$ is hydrogen, C$_1$–C$_3$ alkyl, phenyl, phenylmethyl, pyridinyl, pyridinylmethyl, pyridinylethyl, benzoyl, 4-(aminoiminomethyl)benzoyl, —(CH$_2$)$_m$—CH$_2$OH, —$(CH_2)_m$—COOH, —$(CH_2)_m CH_2$—O—$(CH_2)_m$—$CH_2OH$, —CO—$(CH_2)_m$—COOH, or

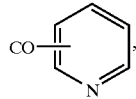

$R_6$ is hydrogen, $C_1$–$C_3$ alkyl, or, $R_5$ and $R_6$ together form, with the nitrogen to which they are attached, a 5- or 6-membered N heterocycle;

n=1, 2, 3 or 4; and m=1, 2 or 3; comprising the steps of:

(a) reacting an 8-hydroxyquinoline derivative of formula (II):

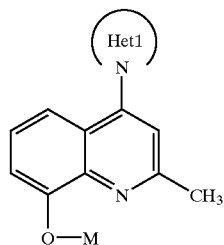

(II)

wherein Het1 is a five-membered nitrogen-containing heterocycle comprising 1, 2, 3 or 4 nitrogen atoms, and wherein M is an alkali metal, with a compound of formula (III):

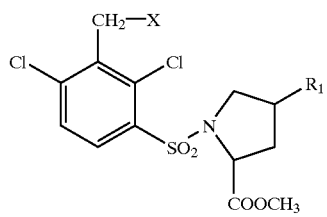

(III)

wherein X is a halogen atom, and $R_1$ is hydrogen, OH, an alkoxy or a phenoxy, in an anhydrous solvent, at a temperature of between 0 and 50° C. for 0.5 to 10 hours, in order to obtain a compound of formula (IV):

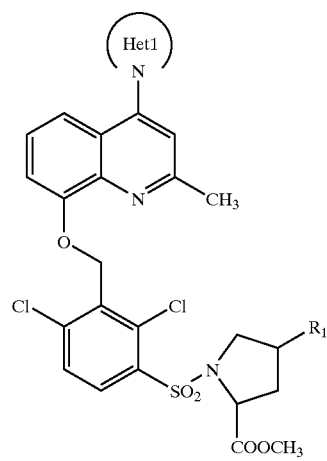

(IV)

wherein Het1 and $R_1$ are as defined above;

(b) hydrolysing the ester of the compound of formula (IV) in order to obtain a compound of formula (V):

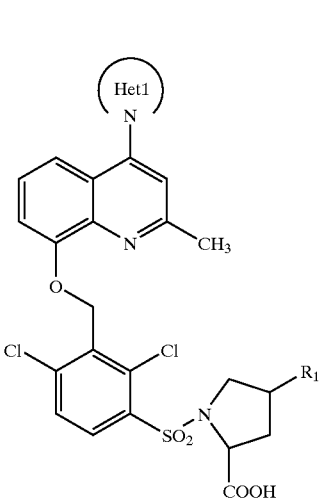

(V)

wherein Het1 and $R_1$ are as defined above;

(c) reacting the compound of formula (V) with an amine of formula (VI):

$HNR_3R_4$     (VI)

wherein $R_3$ is hydrogen, or $C_1$–$C_3$ alkyl, and $R_4$ is hydrogen, $C_1$–$C_3$ alkyl, —$(CH_2)_n$—$CH_2OH$, —$(CH_2)_n$—$COOR_{11}$, —$(CH_2)_n$—$CH_2$—$NR_5R_6$,

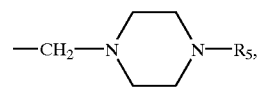

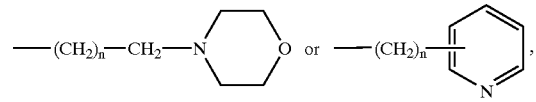

wherein $R_5$ is $C_1$–$C_3$ alkyl —$(CH_2)_m$—$CH_2OH$, —$(CH_2)_m$—$COOR_{11}$, —$(CH_2)_m$—$CH_2$—O—$(CH_2)_m$—$CH_2OH$, or an amino-protecting group, $R_6$ is $C_1$–$C_3$ alkyl or an amino-protecting group, with the proviso that $R_5$ and $R_6$ are not simultaneously an amino protecting group $R_{11}$ is an easily hydrolysable protecting group for the acid functionality, n=1, 2, 3 or 4, and m=1, 2 or 3, in a solvent, in the presence of activators, at a temperature close to ambient temperature for 2 to 50 hours, in order to obtain a compound of formula (VII):

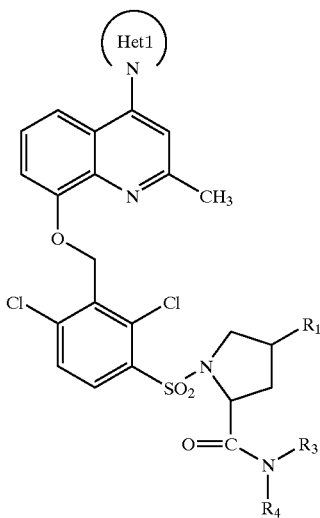

(VII)

wherein Het1, $R_1$, $R_3$, and $R_4$ are as defined above; and (d) if necessary, reacting the compound of formula (VII) in order to replace each amino- or acid protecting group by a hydrogen atom, so as to obtain a compound of formula (I):

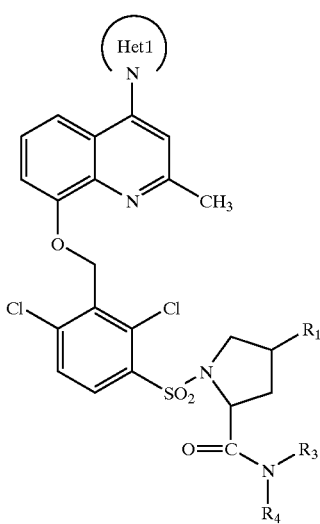

(I)

wherein Het1, $R_1$, $R_3$ and $R_4$ are as defined above, with the proviso that the protecting groups, if present, are replaced by hydrogen atoms;

(e) if necessary, reacting the compound of formula (I) thus obtained with an acid in order to obtain the corresponding acid addition salt.

6. A method of preparing a heterocyclic benzenesulphonamide compound of formula (I)

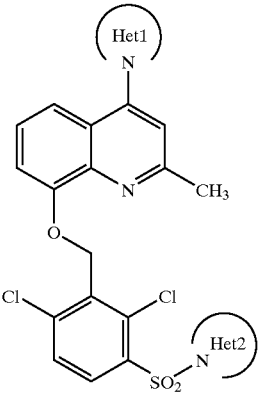

(I)

wherein Het1 is a 5-membered nitrogen-containing heterocycle,

Het2 is

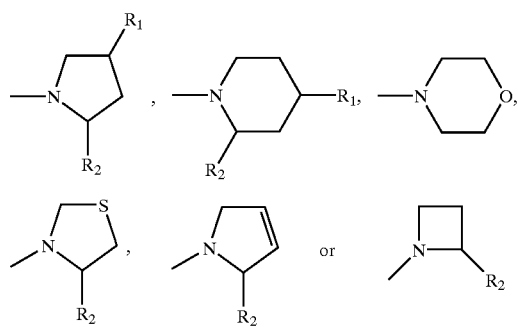

wherein $R_1$ is hydrogen, hydroxyl, $C_1$–$C_4$ alkoxy, phenoxy, phenylmethoxy, —$CH_2OH$, cycloalkyloxy, cycloalkylalkoxy (where each cycloalkyl fragment is $C_3$–$C_8$ and the alkoxy fragment is $C_1$–$C_4$), —NH—CO—$CH_3$, —CO—$NH_2$ or —CO—NH—$CH_3$, $R_2$ is hydrogen, —$CH_2OH$, —$CH_2$—O—$CH_3$, —$CONR_3R_4$,

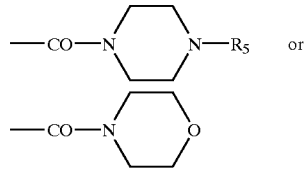

or

—CO—N◯N—O wherein $R_3$ is hydrogen, $C_1$–$C_3$ alkyl, $C_3$–$C_8$ cycloalkyl, ($C_3$–$C_8$) cycloalkyl ($C_1$–$C_3$) alkyl, phenyl, or phenylmethyl, $R_4$ is hydrogen, $C_1$–$C_3$ alkyl, —$(CH_2)n$—$CH_2OH$, —$(CH_2)n$—COOH, —$(CH_2)n$—$CH_2$—$NR_5R_6$, —CH₂—N(piperazine)N—R₅, —(CH₂)ₙ—CH₂—N(morpholine)O   or   —(CH₂)ₙ—(pyridine), R₅ is hydrogen, $C_1$–$C_3$ alkyl, phenyl, phenylmethyl, pyridinyl, pyridinylmethyl, pyridinylethyl, benzoyl, 4-(aminoiminomethyl)benzoyl, —(CH₂)$_m$—CH₂OH, —(CH₂)$_m$—COOH, —(CH₂)$_m$CH₂—O—(CH₂)$_m$—CH₂OH, —CO—(CH₂)$_m$—COOH, or CO—(pyridine)

R₆ is hydrogen $C_1$–$C_3$ alkyl, or, R₅ and R₆ together form, with the nitrogen to which they are attached, a 5- or 6-membered N heterocycle;

n=1, 2, 3 or 4; and m=1, 2 or 3; and the addition salts thereof comprising the steps of:

(a) reacting a compound of formula (I),

[Structure of compound (I): quinoline with Het1, CH₃, O-linker to dichlorobenzene with SO₂-pyrrolidine-C(=O)-NR₃R₄]

wherein Het1 is 1-imidazolyl, 1-pyrazolyl, or 1-(1,2,4-triazolyl),

R₃ is H, or $C_1$–$C_3$ alkyl,

R₄ is a group which carries a primary or secondary amine functionality chosen from: —(CH₂)ₙ—CH₂—NHR₆ or —CH₂—(piperidine)N—H wherein R₆ is H or an alkyl and n is 1, 2, 3 or 4, with a halogenated compound chosen from the group consisting of: Y—(CH₂)$_m$—CH₂OR₁₃, Y—(CH₂)$_m$—COOR₁₁, and Y—(CH₂)$_m$—CH₂—O—(CH₂)$_m$—CH₂OR₁₃, wherein Y is a halogen, m is 1, 2 or 3

R₁₁ is an acido-protecting group,

R₁₃ is a protecting group of the alcohol functionality in a solvent, in the presence of an alkaline agent, at a temperature close to ambient temperature, for 5 to 20 hours, in order to obtain a compound of formula (VII):

(VII)

[Structure of compound (VII): same quinoline core with SO₂-pyrrolidine-C(=O)-NR₃R₄]

wherein R₃ is H or $C_1$–$C_3$ alkyl,

R₄ is —(CH₂)ₙ—CH₂—NR₅R₆ or

—CH₂—(piperidine)N—R₅, wherein R₅ is —(CH₂)$_m$—CH₂OR₁₃, —(CH₂)$_m$—COOR₁₁, or —(CH₂)$_m$—CH₂—O—(CH₂)$_m$—CH₂OR₁₃, and Het1, R₆, R₁₁ and R₁₃ are as defined above;

(b) carrying out a deprotection reaction of each alcohol or acid functionality in order to replace R₁₃ and R₁₁ by a hydrogen atom to obtain the corresponding compounds of formula (I); and (c) if necessary, reacting the compound of formula (I) with an inorganic or organic acid in order to obtain the corresponding salt.

7. A method of preparing a compound of formula (I),

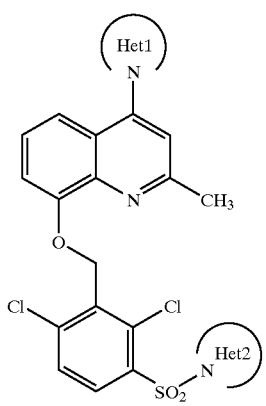
(I)

wherein, Het1 is a 5-membered nitrogen-containing heterocycle,
Het2 is

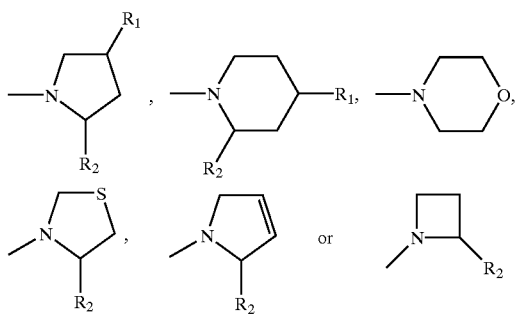

wherein $R_1$ is hydrogen, hydroxyl, $C_1$–$C_4$ alkoxy, phenoxy, phenylmethoxy, —$CH_2OH$, cycloalkyloxy, cycloalkylalkoxy (where each cycloalkyl fragment is $C_3$–$C_8$ and the alkoxy fragment is $C_1$–$C_4$), —NH—CO—$CH_3$, —CO—$NH_2$ or —CO—NH—$CH_3$,
$R_2$ is hydrogen, —$CH_2OH$, —$CH_2$—O—$CH_3$, —$CONR_3R_4$,

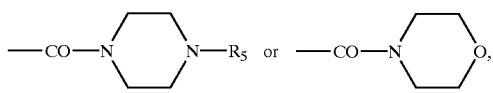

wherein $R_3$ is hydrogen, $C_1$–$C_3$ alkyl, $C_3$–$C_8$ cycloalkyl, ($C_3$–$C_8$) cycloalkyl ($C_1$–$C_3$) alkyl, phenyl, or phenylmethyl,
$R_4$ is hydrogen, $C_1$–$C_3$ alkyl, —$(CH_2)n$—$CH_2OH$, —$(CH_2)n$—COOH, —$(CH_2)n$—$CH_2$—$NR_5R_6$,

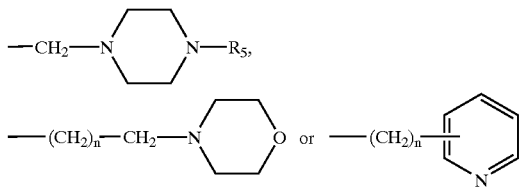

$R_5$ is hydrogen, $C_1$–$C_3$ alkyl, phenyl, phenylmethyl, pyridinyl, pyridinylmethyl, pyridinylethyl, benzoyl, 4-(aminoiminomethyl)benzoyl, —$(CH_2)_m$—$CH_2OH$, —$(CH_2)_m$—COOH, —$(CH_2)_m CH_2$—O—$(CH_2)_m$—$CH_2OH$, —CO—$(CH_2)_m$—COOH, or

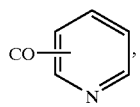

$R_6$ is hydrogen $C_1$–$C_3$ alkyl, or, $R_5$ and $R_6$ together form, with the nitrogen to which they are attached, a 5- or 6-membered N heterocycle;
n=1, 2, 3 or 4; and
m=1, 2 or 3; comprising the steps of:
(a) reacting the acid chloride of formula (VIII):

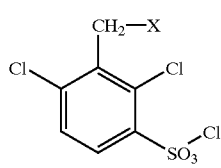
(VIII)

wherein X is a halogen, with

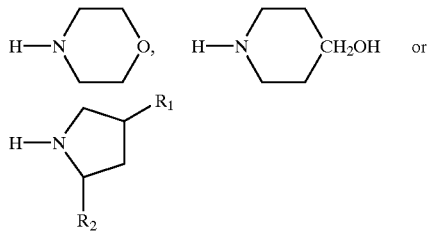

wherein $R_1$ is H, OH, alkoxy, phenoxy, phenylmethoxy, $CH_2OH$, $C_3$–$C_8$ cycloalkyloxy or cycloalkylalkoxy where the cycloalkyl fragment is $C_1$–$C_8$ and the alkoxy fragment is $C_1$–$C_4$, and
$R_2$ is —$CH_2OH$, —$CH_2OCH_3$, —CONH($CH_2$)$_n CH_2 NR_5 R_{12}$, —CONH($CH_2$)$_n CH_2OH$, —CONH($CH_2$)$_n COOR_{11}$ or

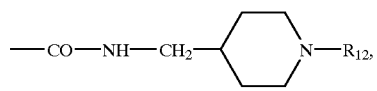

wherein n=1, 2, 3 or 4,
$R_5$ is H or alkyl,
$R_{11}$ is an acido-protecting group, and
$R_{12}$ is an amino-protecting group,
in a solvent, in the presence of a base, at a temperature close to ambient temperature, for 10 to 30 hours, in order to obtain a compound of formula (IX):

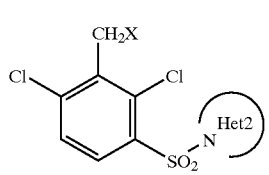
(IX)

wherein

Het2 is

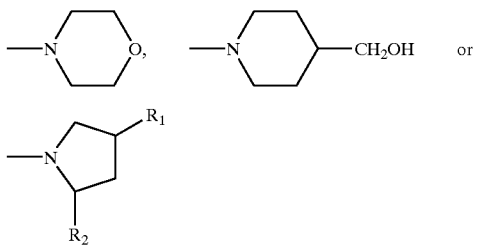

and X, $R_1$, $R_2$, $R_{11}$, $R_{12}$ and n are as defined above;

(b) reacting the compound of formula (IX) with an 8-hydroxyquinoline derivative of formula (II):

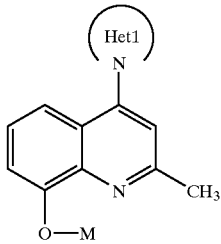

(II)

wherein Het1 is a 5-membered nitrogen-containing heterocycle comprising 1, 2, 3 or 4 nitrogen atoms, and M is an alkali metal, in an anhydrous solvent, at a temperature of between 0 and 50° C., for 0.5 to 10 hours, in order to obtain a compound of formula (X):

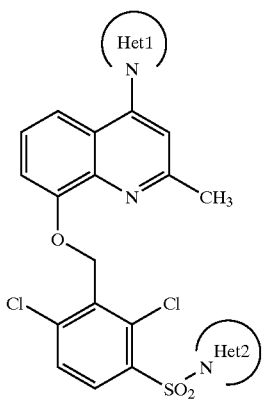

(X)

wherein Het1 and Het2 are as defined above;

(c) if necessary, carrying out a deprotection reaction to replace $R_{11}$ and $R_{12}$ by a hydrogen atom, in order to obtain a compound of formula (I):

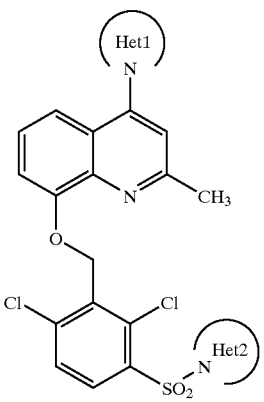

wherein Het1 and Het2 are as defined above, and

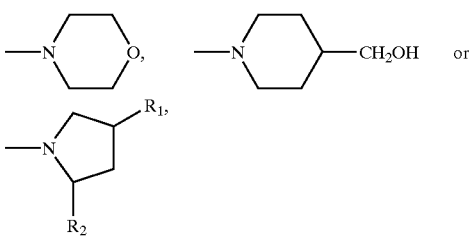

$R_1$ is as defined above,
$R_2$ is —$CH_2OH$, —$CH_2OCH_3$, $CONH(CH_2)_nCH_2NHR_5$, —$CONH(CH_2)_nCH_2OH$, —$CONH(CH_2)_nCOOH$ or

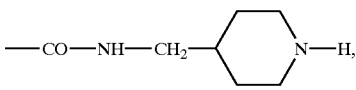

n=1, 2, 3 or 4, and
$R_5$ is H or an alkyl group; and (d) if necessary, reacting the compound of formula (I) with an acid in order to obtain the corresponding salt.

8. A pharmaceutical composition, comprising a physiologically acceptable excipient and at least one compound of formula (I):

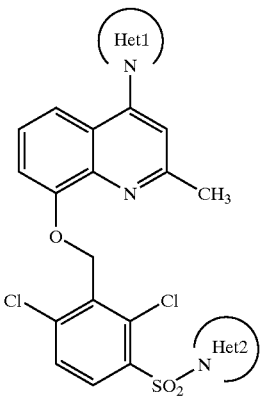

(I)

wherein, Het1 is a 5-membered nitrogen-containing heterocycle,

Het2 is

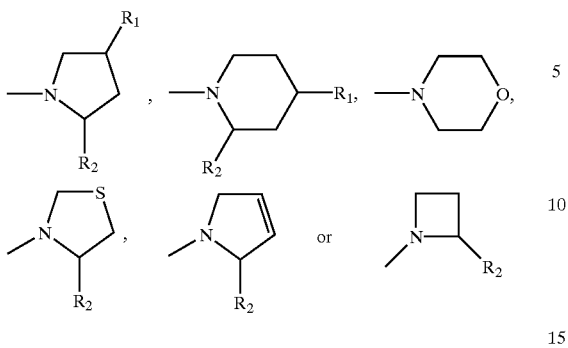

wherein R₁ is hydrogen, hydroxyl, $C_1$–$C_4$ alkoxy, phenoxy, phenylmethoxy, —$CH_2OH$, cycloalkyloxy, cycloalkylalkoxy (where each cycloalkyl fragment is $C_3$–$C_8$ and the alkoxy fragment is $C_1$–$C_4$), —NH—CO—$CH_3$, —CO—$NH_2$ or —CO—NH—$CH_3$, $R_2$ is hydrogen, —$CH_2OH$, —$CH_2$—O—$CH_3$, —$CONR_3R_4$,

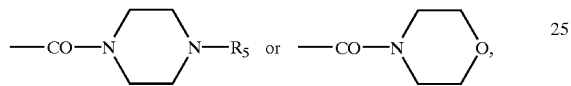

wherein $R_3$ is hydrogen, $C_1$–$C_3$ alkyl, $C_3$–$C_8$ cycloalkyl, ($C_3$–$C_8$) cycloalkyl ($C_1$–$C_3$) alkyl, phenyl, or phenylmethyl, $R_4$ is hydrogen, $C_1$–$C_3$ alkyl, —($CH_2$)n—$CH_2OH$, —($CH_2$)n—COOH, —($CH_2$)n—$CH_2$—$NR_5R_6$,

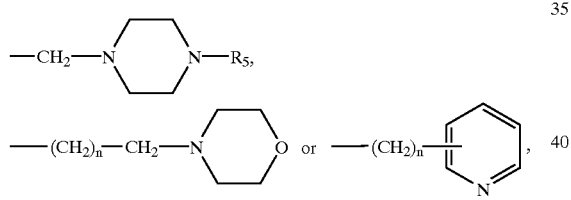

wherein $R_5$ is hydrogen, $C_1$–$C_3$ alkyl, phenyl, phenylmethyl, pyridinyl, pyridinylmethyl, pyridinylethyl, benzoyl, 4-(aminoiminomethyl) benzoyl, —($CH_2$)ₘ—$CH_2OH$, —($CH_2$)ₘ—COOH, —($CH_2$)ₘ$CH_2$—O—($CH_2$)ₘ—$CH_2OH$, —CO—($CH_2$)ₘ—COOH, or

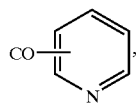

$R_6$ is hydrogen or a $C_1$–$C_3$ alkyl group, or, $R_5$ and $R_6$ together form, with the nitrogen to which they are attached, a 5- or 6-membered N heterocycle;

n=1, 2, 3 or 4; and m=1, 2 or 3;

and the addition salts thereof.

9. A method of treating a pathological state in a mammal involving bradykinin or its homologues comprising administration of a therapeutically effective amount of a compound which is an antagonist of a bradykinin receptor and of analogous hormones, wherein said compound is a heterocyclic benzenesulphonamide compound of formula (I):

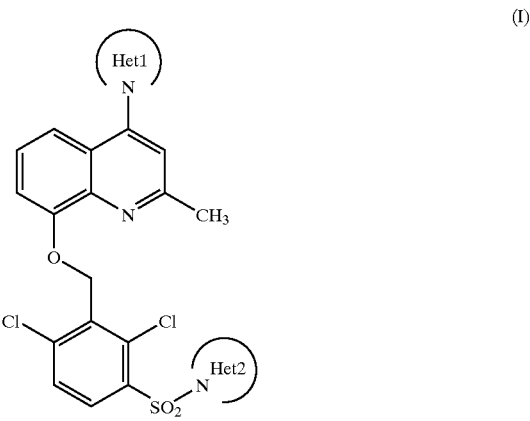

(I)

wherein Het1 is a 5-membered nitrogen-containing heterocycle,

Het2 is

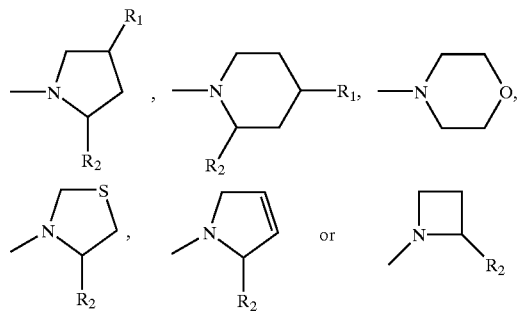

wherein R₁ is hydrogen, hydroxyl, $C_1$–$C_4$ alkoxy, phenoxy, phenylmethoxy, —$CH_2OH$, cycloalkyloxy, cycloalkylalkoxy (where each cycloalkyl fragment is $C_3$–$C_8$ and the alkoxy fragment is $C_1$–$C_4$), —NH—CO—$CH_3$, —CO—$NH_2$ or —CO—NH—$CH_3$, $R_2$ is hydrogen, —$CH_2OH$, —$CH_2$—O—$CH_3$, —$CONR_3R_4$,

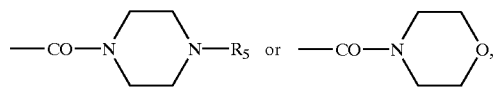

wherein $R_3$ is hydrogen, $C_1$–$C_3$ alkyl, $C_3$–$C_8$ cycloalkyl group, ($C_3$–$C_8$) cycloalkyl ($C_1$–$C_3$) alkyl, phenyl, or phenylmethyl, $R_4$ is hydrogen, $C_1$–$C_3$ alkyl, —($CH_2$)n—$CH_2OH$, —($CH_2$)n—COOH, —($CH_2$)n—$CH_2$—$NR_5R_6$,

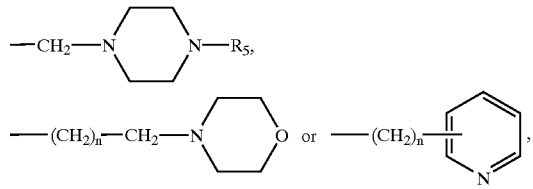

wherein $R_5$ is hydrogen, $C_1$–$C_3$ alkyl, phenyl, phenylmethyl, pyridinyl, pyridinylmethyl, pyridinylethyl, benzoyl, 4-(aminoiminomethyl) benzoyl, —(CH$_2$)$_m$—CH$_2$OH, —(CH$_2$)$_m$—COOH, —(CH$_2$)$_m$CH$_2$—O—(CH$_2$)$_m$—CH$_2$OH, —CO—(CH$_2$)$_m$—COOH, or

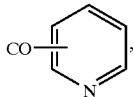, $R_6$ is hydrogen $C_1$–$C_3$ alkyl, or, $R_5$ and $R_6$ together form, with the nitrogen to which they are attached, a 5- or 6-membered N heterocycle;

n=1, 2, 3 or 4; and m=1, 2 or 3; and the addition salts thereof.

10. A method according to claim 9, wherein said pathological state is a painful condition.

11. A method according to claim 9, wherein said pathological state is an inflammatory condition.

12. A method according to claim 9, wherein said pathological state is traumatism caused by a severe shock.

13. A compound of claim 1, wherein Het1 is imidazole, pyrazole, or triazole.

14. The method of claim 5, wherein M is sodium or potassium.

15. The method of claim 5, wherein X is bromine.

16. The method of claim 5, wherein said ester functionality is hydrolysed at a temperature of between about 0° and 40° C.

17. The method of claim 16, wherein said temperature is between about 10° and 35° C.

18. The method of claim 6, wherein Y is bromine or iodine.

19. The method of claim 6, wherein $R_{11}$ is t-butyl.

20. The method of claim 7, wherein X is bromine.

* * * * *

UNITED STATES PATENT AND TRADEMARK OFFICE
CERTIFICATE OF CORRECTION

PATENT NO. : 6,479,515 B1  Page 1 of 2
DATED : November 12, 2002
INVENTOR(S) : Dodey et al.

It is certified that error appears in the above-identified patent and that said Letters Patent is hereby corrected as shown below:

Column 5,
Line 42, "C.," should read -- C, --

Column 6,
Line 30, "C.," should read -- C, --

Column 7,
Line 66, "C.," should read -- C, --
Line 66, "C.)," should read -- C), --

Column 14,
Line 29, "(EDC1)" should read -- (EDCI) --

Column 18,
Line 3, "C.," should read -- C, --

Column 22,
Line 56, "$[\alpha]^{27hd\,D}$" should read -- $[\alpha]^{27}_D$ --

Column 49,
Line 29, "C." should read -- C --

Column 77,
Line 5, should read --

Column 78,
Line 59,

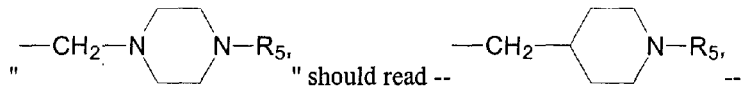 should read --

Column 83,
Line 5,

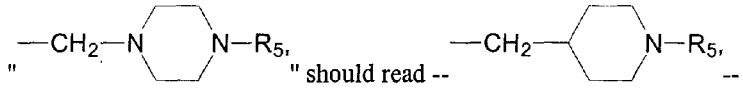 should read --

UNITED STATES PATENT AND TRADEMARK OFFICE
CERTIFICATE OF CORRECTION

PATENT NO. : 6,479,515 B1
DATED : November 12, 2002
INVENTOR(S) : Dodey et al.

It is certified that error appears in the above-identified patent and that said Letters Patent is hereby corrected as shown below:

<u>Column 85,</u>
Line 59,

<u>Column 89,</u>
Line 37,

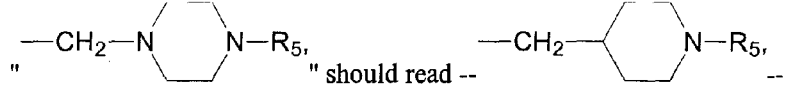

<u>Column 90,</u>
Line 59,

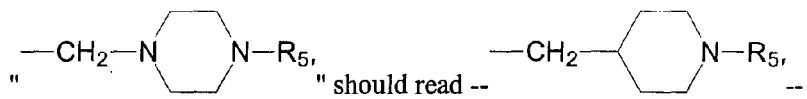

Signed and Sealed this

Twelfth Day of August, 2003

JAMES E. ROGAN
*Director of the United States Patent and Trademark Office*